United States Patent
Min et al.

(10) Patent No.: US 9,893,290 B2
(45) Date of Patent: Feb. 13, 2018

(54) COMPOSITION AND ORGANIC OPTOELECTRIC DEVICE AND DISPLAY DEVICE

(71) Applicants: Soo-Hyun Min, Uiwang-si (KR);
Gi-Wook Kang, Uiwang-si (KR);
Dong-Min Kang, Uiwang-si (KR);
Eui-Su Kang, Uiwang-si (KR);
Youn-Hwan Kim, Uiwang-si (KR);
Yong-Tak Yang, Uiwang-si (KR);
Jae-Jin Oh, Uiwang-si (KR);
Nam-Heon Lee, Uiwang-si (KR);
Jin-Hyun Lui, Uiwang-si (KR);
Eun-Sun Yu, Uiwang-si (KR); Ho-Kuk Jung, Uiwang-si (KR); Young-Kyoung Jo, Uiwang-si (KR)

(72) Inventors: Soo-Hyun Min, Uiwang-si (KR);
Gi-Wook Kang, Uiwang-si (KR);
Dong-Min Kang, Uiwang-si (KR);
Eui-Su Kang, Uiwang-si (KR);
Youn-Hwan Kim, Uiwang-si (KR);
Yong-Tak Yang, Uiwang-si (KR);
Jae-Jin Oh, Uiwang-si (KR);
Nam-Heon Lee, Uiwang-si (KR);
Jin-Hyun Lui, Uiwang-si (KR);
Eun-Sun Yu, Uiwang-si (KR); Ho-Kuk Jung, Uiwang-si (KR); Young-Kyoung Jo, Uiwang-si (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 997 days.

(21) Appl. No.: 14/106,931

(22) Filed: Dec. 16, 2013

(65) Prior Publication Data
US 2015/0001488 A1 Jan. 1, 2015

(30) Foreign Application Priority Data
Jul. 1, 2013 (KR) .......................... 10-2013-0076669

(51) Int. Cl.
| H01L 51/54 | (2006.01) |
| H01L 51/00 | (2006.01) |
| C09K 11/06 | (2006.01) |
| C07D 405/04 | (2006.01) |
| C07D 409/04 | (2006.01) |
| C07D 487/04 | (2006.01) |
| C07D 209/86 | (2006.01) |
| H01L 51/50 | (2006.01) |

(52) U.S. Cl.
CPC ........ *H01L 51/0054* (2013.01); *C07D 209/86* (2013.01); *C07D 405/04* (2013.01); *C07D 409/04* (2013.01); *C07D 487/04* (2013.01); *C09K 11/06* (2013.01); *H01L 51/0072* (2013.01); *C09K 2211/1007* (2013.01); *C09K 2211/1029* (2013.01); *C09K 2211/185* (2013.01); *H01L 51/0052* (2013.01); *H01L 51/0067* (2013.01); *H01L 51/0073* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| 2010/0187977 A1 | 7/2010 | Kai et al. |
| 2011/0062862 A1 | 3/2011 | Yamamoto et al. |
(Continued)

FOREIGN PATENT DOCUMENTS

| CN | 102318101 A | 1/2012 |
| CN | 102326273 A | 1/2012 |
(Continued)

OTHER PUBLICATIONS

Search Report dated Jan. 8, 2015 in corresponding European Patent Application No. 13196046.0.
(Continued)

*Primary Examiner* — Marie R. Yamnitzky
(74) *Attorney, Agent, or Firm* — Lee & Morse, P.C.

(57) ABSTRACT

A composition includes a first host compound including moieties represented by Chemical Formulae 1 to 3 that are sequentially bonded with each other, and a second host compound including at least one carbazole group with a substituent having hole characteristics,

[Chemical Formula 1]

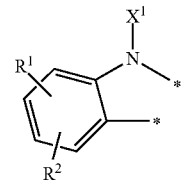

[Chemical Formula 2]

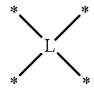

[Chemical Formula 3]

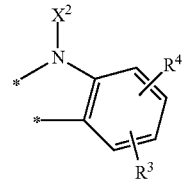

18 Claims, 1 Drawing Sheet

(56) References Cited

U.S. PATENT DOCUMENTS

| | | | |
|---|---|---|---|
| 2012/0001158 A1 | 1/2012 | Asari et al. | |
| 2012/0001165 A1 | 1/2012 | Komori et al. | |
| 2012/0138915 A1 † | 6/2012 | Nishimura et al. | |
| 2012/0223295 A1 | 9/2012 | Inoue et al. | |
| 2012/0273764 A1 | 11/2012 | Yu et al. | |
| 2013/0150576 A1 | 6/2013 | Hotta et al. | |
| 2014/0070204 A1 † | 3/2014 | Nagao et al. | |
| 2014/0151647 A1 * | 6/2014 | Mizuki et al. | H05B 33/20 257/40 |
| 2014/0306207 A1 † | 10/2014 | Nishimura et al. | |
| 2015/0325796 A1 * | 11/2015 | Tada et al. | H01L 51/5278 257/40 |

FOREIGN PATENT DOCUMENTS

| | | | |
|---|---|---|---|
| CN | 102473859 A | 5/2012 | |
| CN | 103108875 A | 5/2013 | |
| EP | 2 403 028 A1 | 1/2012 | |
| JP | 3139321 B2 | 2/2001 | |
| JP | 4388590 B2 | 12/2009 | |
| KR | 10-1247626 B1 | 3/2010 | |
| KR | 10 2010-0131745 A | 12/2010 | |
| KR | 10 2012-0130074 A | 11/2012 | |
| KR | 10 2012-0140140 A | 12/2012 | |
| KR | 10-1212670 B1 | 12/2012 | |
| WO | WO 2009/136596 A1 | 11/2009 | |
| WO | WO 2010/098246 A1 | 9/2010 | |
| WO | WO 2011/152596 A1 | 12/2011 | |
| WO | WO 2012/035853 A1 | 3/2012 | |
| WO | WO 2012/087955 A1 | 6/2012 | |
| WO | WO 2012/153725 A1 | 11/2012 | |
| WO | WO 2013/062075 A1 | 5/2013 | |

OTHER PUBLICATIONS

Search Report dated Aug. 18, 2015 in corresponding Chinese Patent Application No. 2014100420493.

\* cited by examiner
† cited by third party

【FIG. 1】
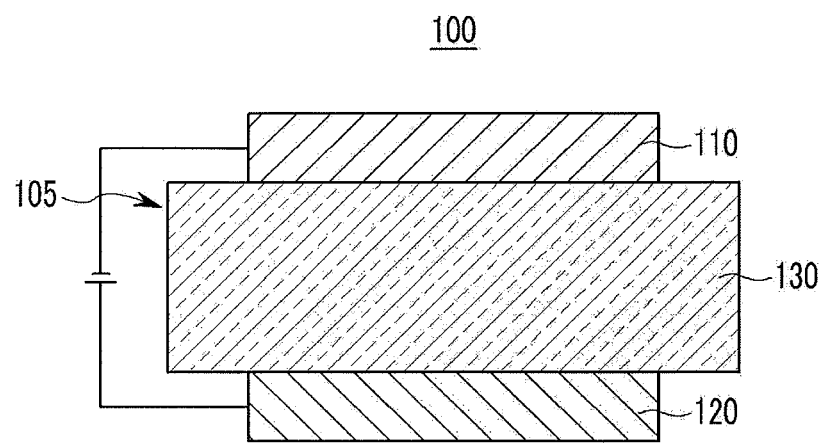
【FIG. 2】
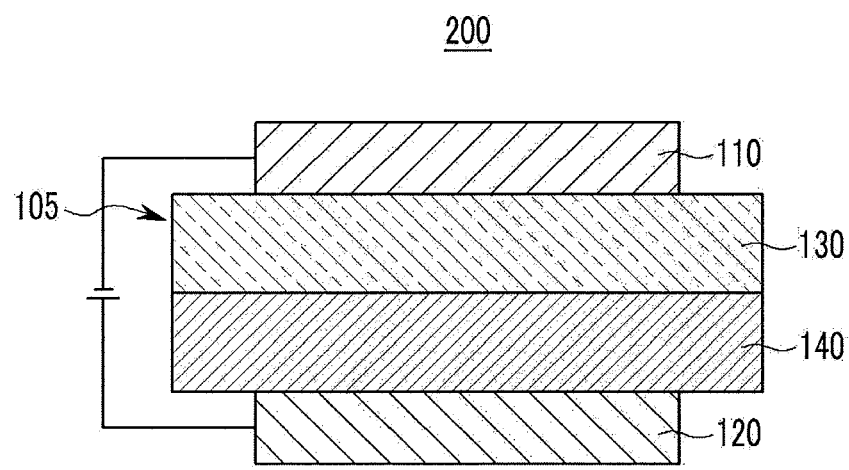

COMPOSITION AND ORGANIC OPTOELECTRIC DEVICE AND DISPLAY DEVICE

CROSS-REFERENCE TO RELATED APPLICATION

Korean Patent Application No. 10-2013-0076669, filed on Jul. 1, 2013, in the Korean Intellectual Property Office, and entitled: "Composition and Organic Optoelectric Device and Display Device," is incorporated by reference herein in its entirety.

BACKGROUND

1. Field

Embodiments relate to a composition, an organic optoelectric device, and a display device.

2. Description of the Related Art

An organic optoelectric device may be a device that converts electrical energy into photoenergy or vice versa. An organic optoelectric device may be classified as follows in accordance with its driving principles. One is an electronic device where excitons generated by photoenergy are separated into electrons and holes, and the electrons and holes are transferred to separate electrodes respectively and electrical energy is produced. Another is a light emitting device to generate photoenergy from electrical energy by supplying a voltage or a current to electrodes.

SUMMARY

Embodiments are directed to a composition including a first host compound including moieties represented by the following Chemical Formulae 1 to 3 that are sequentially bonded with each other, and a second host compound including at least one carbazole group with a substituent having hole characteristics,

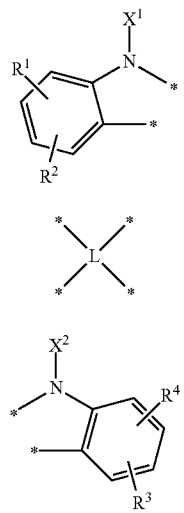

[Chemical Formula 1]

[Chemical Formula 2]

[Chemical Formula 3]

In the Chemical Formulae 1 to 3,
$X^1$ may be *—$Y^1$-ET,
$X^2$ may be *—$Y^2$—$Ar^1$,
ET may be a substituent for accepting an electron when an electric field is applied, $Ar^1$ may be a substituted or unsubstituted C6 to C30 aryl group, a substituted or unsubstituted C2 to C30 heteroaryl group, or a combination thereof, $Y^1$ and $Y^2$ may each independently be a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, L may be a substituted or unsubstituted C2 or C3 alkenylene group or a substituted or unsubstituted C6 to C20 arylene group, and $R^1$ to $R^4$ may each independently be hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

Embodiments are also directed to an organic optoelectric device that includes an anode and a cathode facing each other, and at least one organic layer interposed between the anode and the cathode, the organic layer including the composition according to an embodiment.

Embodiments are also directed to a display device including the organic optoelectric device according to an embodiment.

BRIEF DESCRIPTION OF THE DRAWINGS

Features will become apparent to those of skill in the art by describing in detail example embodiments with reference to the attached drawings in which:

FIGS. 1 and 2 illustrate cross-sectional views of each organic light emitting diode according to an example embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, when a definition is not otherwise provided, the term "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, and the like, or a cyano group, instead of at least one hydrogen of a substituent or a compound.

In addition, two adjacent substituents of the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as trifluoromethyl group and the like, or cyano group may be fused with each other to form a ring.

For example, the substituted C6 to C30 aryl group may be fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, P, and Si, and remaining carbons in one compound or substituent.

In the present specification, when a definition is not otherwise provided, the term "alkyl group" may refer to an aliphatic hydrocarbon group.

The alkyl group may refer to "a saturated alkyl" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group includes 1 to 4 carbon in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

As used herein, the term "heteroaryl group" may refer to aryl group including at least one hetero atoms selected from N, O, S, P, and Si and remaining carbons in one functional group.

The heteroaryl group may be a fused ring where each ring may include the 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzothiophenyl group, a substituted or unsubstituted dibenzofuranyl group, a substituted or unsubstituted carbazole group, or a combination thereof, is not limited thereto.

In the specification, hole characteristics refer to characteristics for donating an electron to form a hole when an electric field is applied, and characteristics that hole formed in the anode is easily injected into the emission layer and transported in the emission layer due to conductive characteristics according to HOMO level.

In addition, electron characteristics refer to characteristics for accepting an electron when an electric field is applied, and characteristics that electron formed in the cathode is easily injected into the emission layer and transported in the emission layer due to conductive characteristics according to LUMO level.

Hereinafter, a composition according to an example embodiment is described.

A composition according to the present example embodiment includes a first host compound having electron characteristics and a second host compound having hole characteristics.

According to the present example embodiment, the first host compound includes a substituent having characteristics for accepting an electron when an electric field is applied, that is, electron characteristics, and includes moieties represented by the Chemical Formulae 1 to 3 that are sequentially bonded with each other.

[Chemical Formula 1]

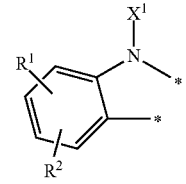

[Chemical Formula 2]

[Chemical Formula 3]

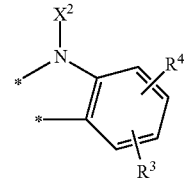

According to the present example embodiment, in the Chemical Formulae 1 to 3,

X¹ is *—Y¹-ET,

X² is *—Y²—Ar¹,

ET is a substituent for accepting an electron when an electric field is applied, Ar¹ is a substituted or unsubstituted C6 to C30 aryl group, a substituted or unsubstituted C2 to C30 heteroaryl group, or a combination thereof, $Y^1$ and $Y^2$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, L is a substituted or unsubstituted C2 or C3 alkenylene group or a substituted or unsubstituted C6 to C20 arylene group, and $R^1$ to $R^4$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

In the Chemical Formulae 1 to 3, "*" indicates linking points between Chemical Formula 1 and Chemical Formula 2, and between Chemical Formula 2 and Chemical Formula 3.

ET may be, for example, a substituent for transporting an electron, and may be, for example, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, or a combination thereof.

The ET may be a heteroaryl group including at least one nitrogen atom. In an implementation, ET is not a carbazolyl group.

According to an example embodiment, ET may be represented by, for example, the following Chemical Formula 1a,

[Chemical Formula 1a]

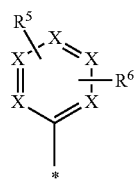

According to the present example embodiment, in the Chemical Formula 1a, each X is independently N, C or $CR^a$, at least one of X is N, and $R^5$, $R^6$, and $R^a$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

In an example embodiment, the ET may be one of the substituents listed in the following Group 1,

[Group 1]

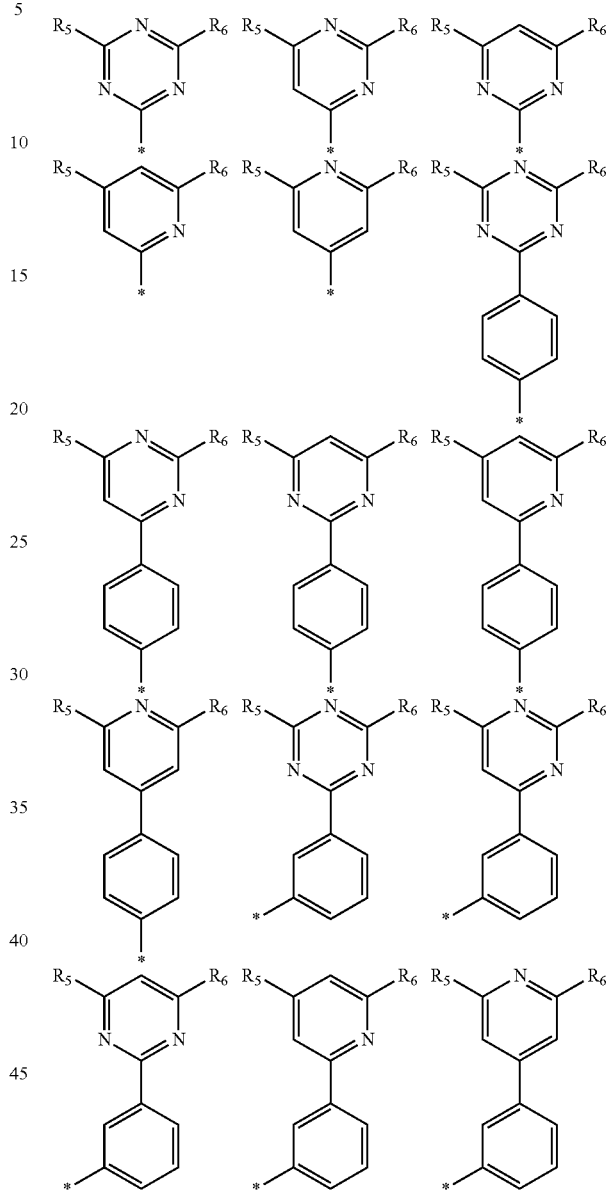

In the Group 1, $R^5$ and $R^6$ are the same as described above.

In an example embodiment, the $X^1$ may be, for example, one of the substituents listed in the following Group 2,

[Group 2]

A-1

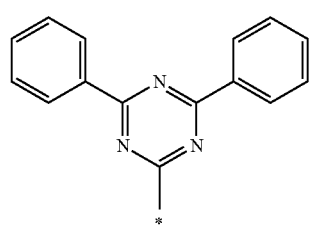

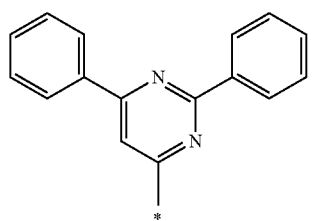
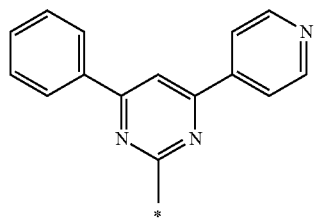

A-14
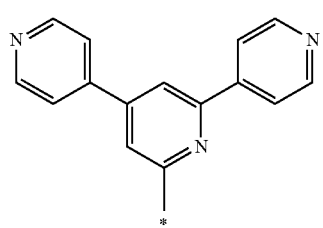
A-15
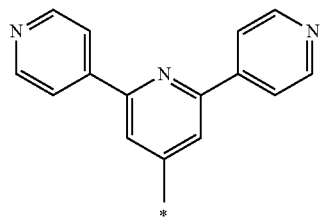
A-16
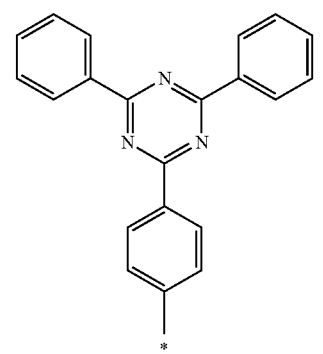
A-17
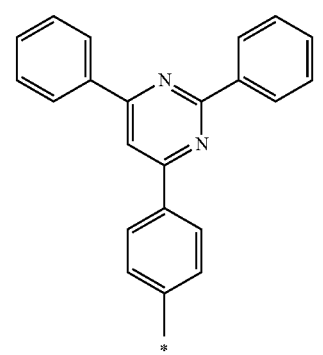
A-18
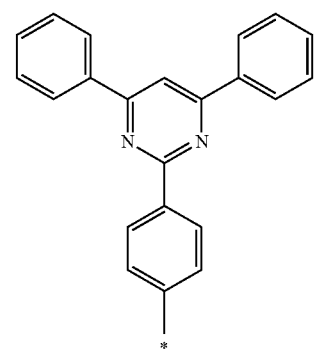
A-19
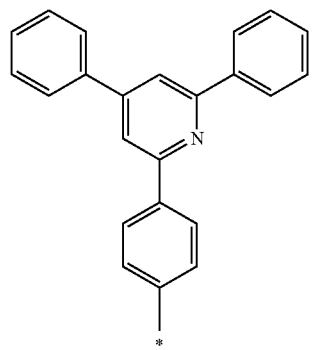
A-20
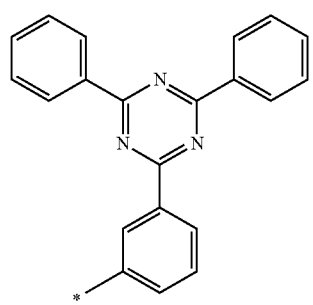
A-21
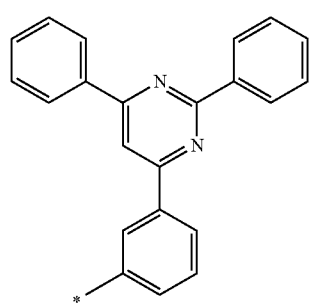
A-22

A-23
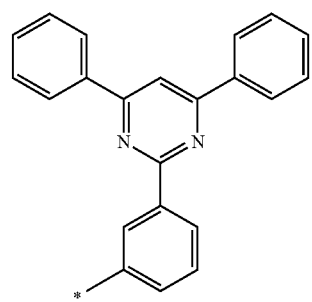
A-24
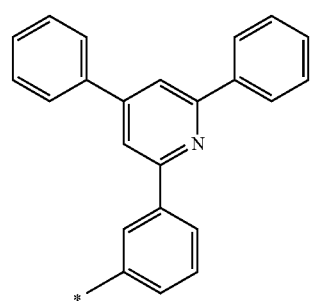
A-25
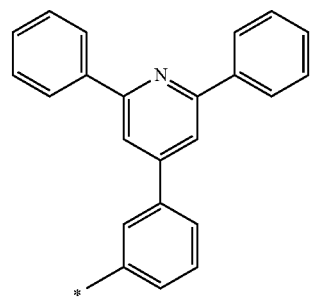
A-26
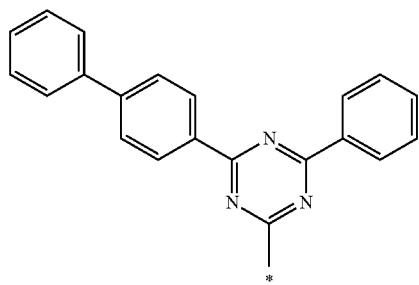
A-27
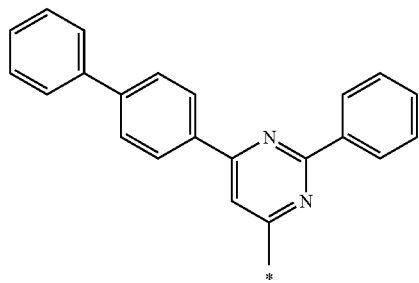
A-28
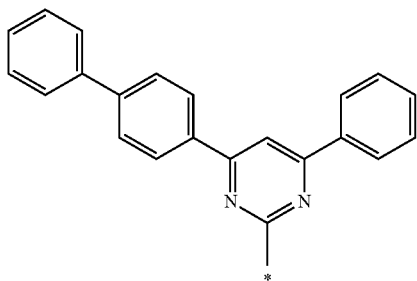
A-29
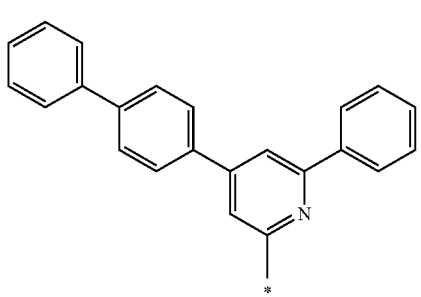
A-30
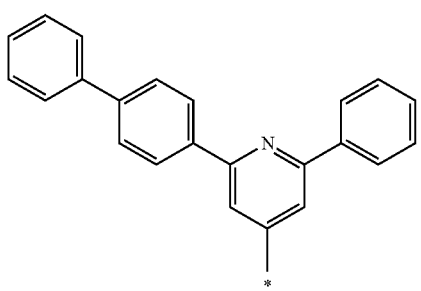
A-31
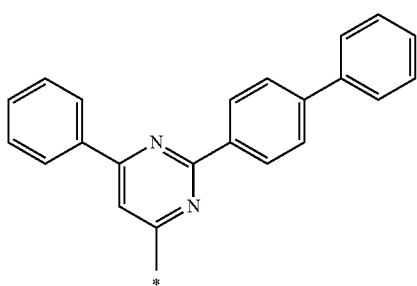
A-32
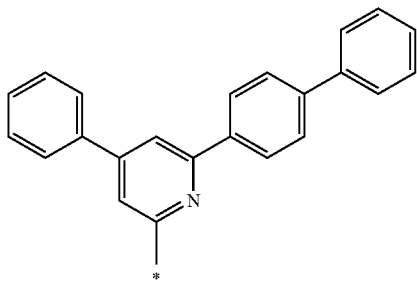

A-33
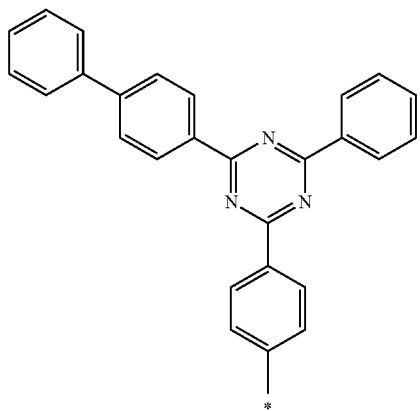
A-34
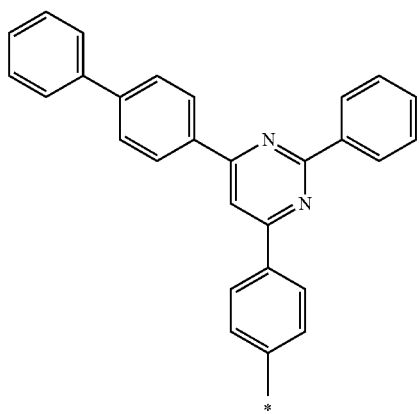
A-35
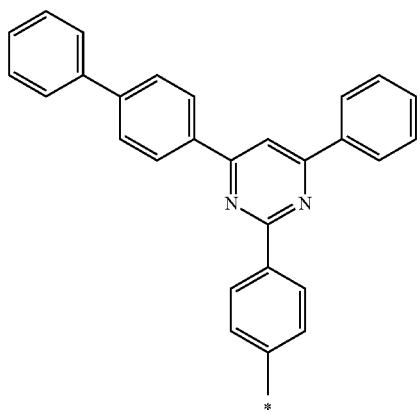
A-36
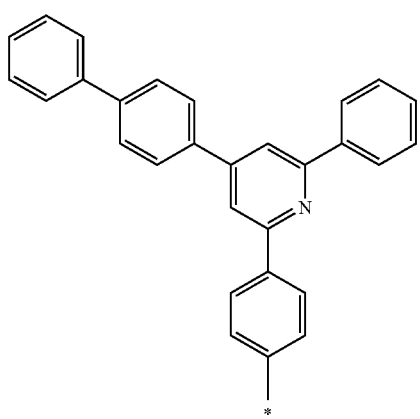
A-37
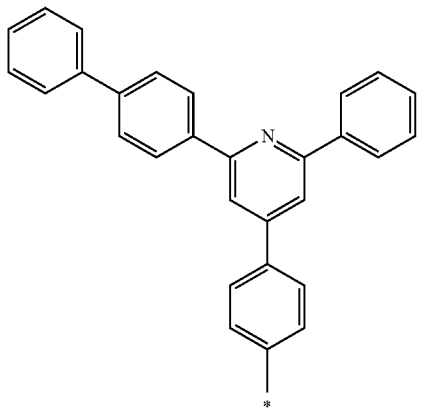
A-38
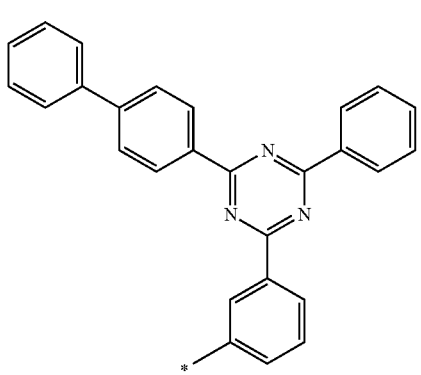
A-39
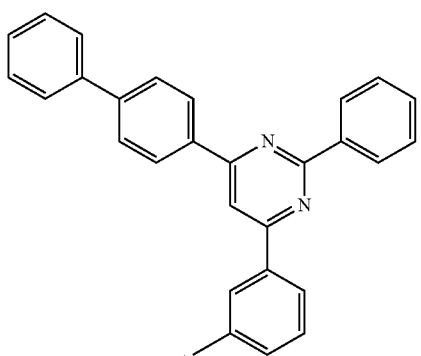
A-40
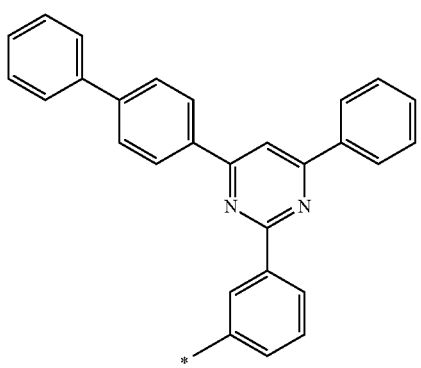

-continued

A-41
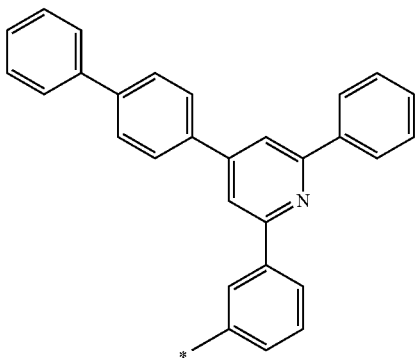

A-42
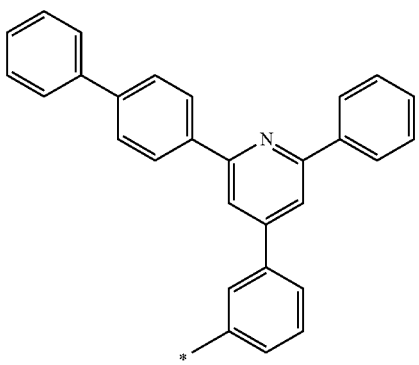

A-43
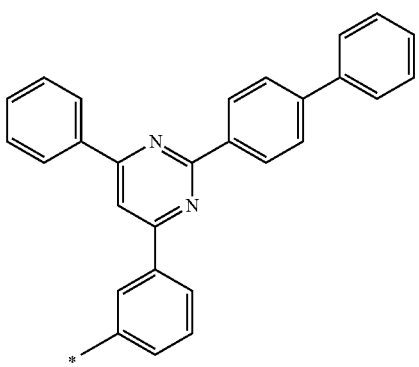

A-44
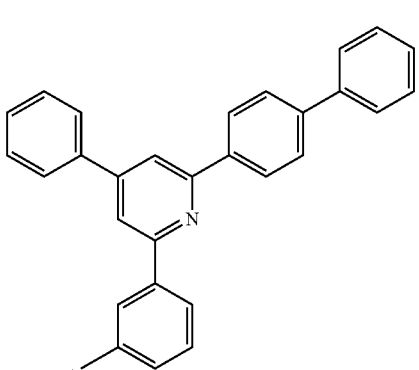

For example, the moiety represented by the Chemical Formula 2 may be represented by one of the Chemical Formulae 2-1 to 2-3,

[Chemical Formula 2-1]
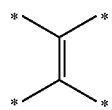

[Chemical Formula 2-2]
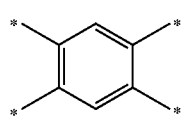

[Chemical Formula 2-3]
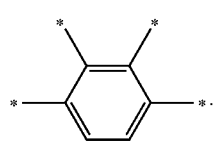

According to an example embodiment, in the moiety represented by the Chemical Formula 3, $Ar^1$ may be, for example, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, substituted unsubstituted dibenzofuranyl group, a substituted or unsubstituted dibenzothiophenyl group, or a combination thereof.

For example, the $X^2$ may be one of the substituents listed in the following Group 3,

[Group 3]

B-1
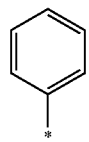

B-2
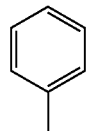

B-3
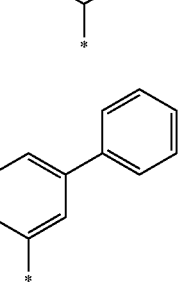

B-4
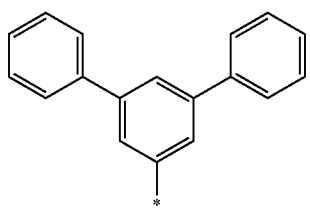
B-5
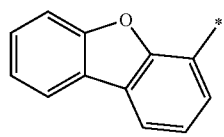
B-6
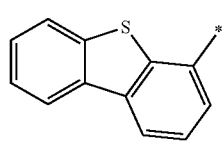
B-7
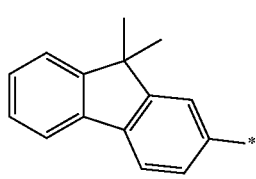
B-8
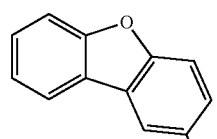
B-9
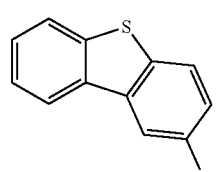
B-10
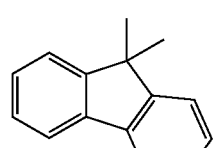
B-11
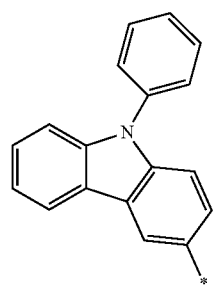
B-12
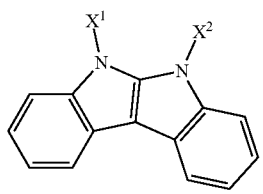
According to an example embodiment, the first host compound may be, e.g., one of compounds listed in the following Group 4,
[Group 4]
[5a-1]
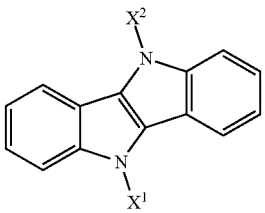
[5a-2]
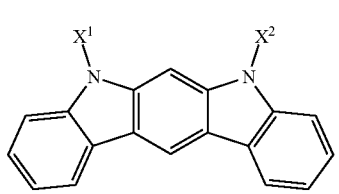
[5b-1]
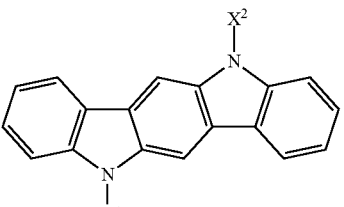
[5b-2]
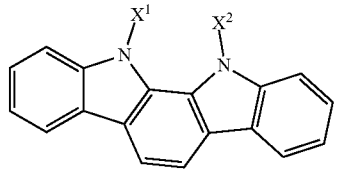
[5c-1]
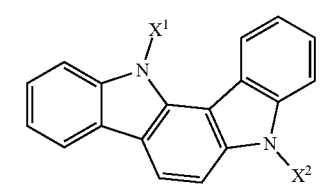
[5c-2]

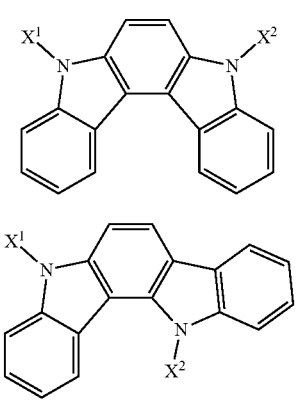

[5c-3]

[5c-4]

In the Group 4, $X^1$ and $X^2$ are the same as described above.

The first host compound may be, for example, compounds listed in the Tables 1 to 11.

TABLE 1

| Cmpd No. | Grp 4 | $X^1$ | $X^2$ |
|---|---|---|---|
| 1-1 | 5a-1 | A-1 | B-1 |
| 1-2 | 5a-1 | A-2 | B-1 |
| 1-3 | 5a-1 | A-3 | B-1 |
| 1-4 | 5a-1 | A-4 | B-1 |
| 1-5 | 5a-1 | A-5 | B-1 |
| 1-6 | 5a-1 | A-6 | B-1 |
| 1-7 | 5a-1 | A-7 | B-1 |
| 1-8 | 5a-1 | A-8 | B-1 |
| 1-9 | 5a-1 | A-9 | B-1 |
| 1-10 | 5a-1 | A-10 | B-1 |
| 1-11 | 5a-1 | A-11 | B-1 |
| 1-12 | 5a-1 | A-12 | B-1 |
| 1-13 | 5a-1 | A-13 | B-1 |
| 1-14 | 5a-1 | A-14 | B-1 |
| 1-15 | 5a-1 | A-15 | B-1 |
| 1-16 | 5a-1 | A-16 | B-1 |
| 1-17 | 5a-1 | A-17 | B-1 |
| 1-18 | 5a-1 | A-18 | B-1 |
| 1-19 | 5a-1 | A-19 | B-1 |
| 1-20 | 5a-1 | A-20 | B-1 |
| 1-21 | 5a-1 | A-21 | B-1 |
| 1-22 | 5a-1 | A-22 | B-1 |
| 1-23 | 5a-1 | A-23 | B-1 |
| 1-24 | 5a-1 | A-24 | B-1 |
| 1-25 | 5a-1 | A-25 | B-1 |
| 1-26 | 5a-1 | A-26 | B-1 |
| 1-27 | 5a-1 | A-27 | B-1 |
| 1-28 | 5a-1 | A-28 | B-1 |
| 1-29 | 5a-1 | A-29 | B-1 |
| 1-30 | 5a-1 | A-30 | B-1 |
| 1-31 | 5a-1 | A-31 | B-1 |
| 1-32 | 5a-1 | A-32 | B-1 |
| 1-33 | 5a-1 | A-33 | B-1 |
| 1-34 | 5a-1 | A-34 | B-1 |
| 1-35 | 5a-1 | A-35 | B-1 |
| 1-36 | 5a-1 | A-36 | B-1 |
| 1-37 | 5a-1 | A-37 | B-1 |
| 1-38 | 5a-1 | A-38 | B-1 |
| 1-39 | 5a-1 | A-39 | B-1 |
| 1-40 | 5a-1 | A-40 | B-1 |
| 1-41 | 5a-1 | A-41 | B-1 |
| 1-42 | 5a-1 | A-42 | B-1 |
| 1-43 | 5a-1 | A-43 | B-1 |
| 1-44 | 5a-1 | A-44 | B-1 |
| 1-45 | 5a-1 | A-1 | B-2 |
| 1-46 | 5a-1 | A-2 | B-2 |
| 1-47 | 5a-1 | A-3 | B-2 |
| 1-48 | 5a-1 | A-4 | B-2 |
| 1-49 | 5a-1 | A-5 | B-2 |
| 1-50 | 5a-1 | A-6 | B-2 |
| 1-51 | 5a-1 | A-7 | B-2 |
| 1-52 | 5a-1 | A-8 | B-2 |
| 1-53 | 5a-1 | A-9 | B-2 |
| 1-54 | 5a-1 | A-10 | B-2 |
| 1-55 | 5a-1 | A-11 | B-2 |
| 1-56 | 5a-1 | A-12 | B-2 |
| 1-57 | 5a-1 | A-13 | B-2 |
| 1-58 | 5a-1 | A-14 | B-2 |
| 1-59 | 5a-1 | A-15 | B-2 |
| 1-60 | 5a-1 | A-16 | B-2 |
| 1-61 | 5a-1 | A-17 | B-2 |
| 1-62 | 5a-1 | A-18 | B-2 |
| 1-63 | 5a-1 | A-19 | B-2 |
| 1-64 | 5a-1 | A-20 | B-2 |
| 1-65 | 5a-1 | A-21 | B-2 |
| 1-66 | 5a-1 | A-22 | B-2 |
| 1-67 | 5a-1 | A-23 | B-2 |
| 1-68 | 5a-1 | A-24 | B-2 |
| 1-69 | 5a-1 | A-25 | B-2 |
| 1-70 | 5a-1 | A-26 | B-2 |
| 1-71 | 5a-1 | A-27 | B-2 |
| 1-72 | 5a-1 | A-28 | B-2 |
| 1-73 | 5a-1 | A-29 | B-2 |
| 1-74 | 5a-1 | A-30 | B-2 |
| 1-75 | 5a-1 | A-31 | B-2 |
| 1-76 | 5a-1 | A-32 | B-2 |
| 1-77 | 5a-1 | A-33 | B-2 |
| 1-78 | 5a-1 | A-34 | B-2 |
| 1-79 | 5a-1 | A-35 | B-2 |
| 1-80 | 5a-1 | A-36 | B-2 |
| 1-81 | 5a-1 | A-37 | B-2 |
| 1-82 | 5a-1 | A-38 | B-2 |
| 1-83 | 5a-1 | A-39 | B-2 |
| 1-84 | 5a-1 | A-40 | B-2 |
| 1-85 | 5a-1 | A-41 | B-2 |
| 1-86 | 5a-1 | A-42 | B-2 |
| 1-87 | 5a-1 | A-43 | B-2 |
| 1-88 | 5a-1 | A-44 | B-3 |
| 1-89 | 5a-1 | A-1 | B-3 |
| 1-90 | 5a-1 | A-2 | B-3 |
| 1-91 | 5a-1 | A-3 | B-3 |
| 1-92 | 5a-1 | A-4 | B-3 |
| 1-93 | 5a-1 | A-5 | B-3 |
| 1-94 | 5a-1 | A-6 | B-3 |
| 1-95 | 5a-1 | A-7 | B-3 |
| 1-96 | 5a-1 | A-8 | B-3 |
| 1-97 | 5a-1 | A-9 | B-3 |
| 1-98 | 5a-1 | A-10 | B-3 |
| 1-99 | 5a-1 | A-11 | B-3 |
| 1-100 | 5a-1 | A-12 | B-3 |
| 1-101 | 5a-1 | A-13 | B-3 |
| 1-102 | 5a-1 | A-14 | B-3 |
| 1-103 | 5a-1 | A-15 | B-3 |
| 1-104 | 5a-1 | A-16 | B-3 |
| 1-105 | 5a-1 | A-17 | B-3 |
| 1-106 | 5a-1 | A-18 | B-3 |
| 1-107 | 5a-1 | A-19 | B-3 |
| 1-108 | 5a-1 | A-20 | B-3 |
| 1-109 | 5a-1 | A-21 | B-3 |
| 1-110 | 5a-1 | A-22 | B-3 |
| 1-111 | 5a-1 | A-23 | B-3 |
| 1-112 | 5a-1 | A-24 | B-3 |
| 1-113 | 5a-1 | A-25 | B-3 |
| 1-114 | 5a-1 | A-26 | B-3 |
| 1-115 | 5a-1 | A-27 | B-3 |
| 1-116 | 5a-1 | A-28 | B-3 |
| 1-117 | 5a-1 | A-29 | B-3 |
| 1-118 | 5a-1 | A-30 | B-3 |
| 1-119 | 5a-1 | A-31 | B-3 |
| 1-120 | 5a-1 | A-32 | B-3 |
| 1-121 | 5a-1 | A-33 | B-3 |
| 1-122 | 5a-1 | A-34 | B-3 |
| 1-123 | 5a-1 | A-35 | B-3 |
| 1-124 | 5a-1 | A-36 | B-3 |
| 1-125 | 5a-1 | A-37 | B-3 |

TABLE 1-continued

| Cmpd No. | Grp 4 | X¹ | X² |
| --- | --- | --- | --- |
| 1-126 | 5a-1 | A-38 | B-3 |
| 1-127 | 5a-1 | A-39 | B-3 |
| 1-128 | 5a-1 | A-40 | B-3 |
| 1-129 | 5a-1 | A-41 | B-3 |
| 1-130 | 5a-1 | A-42 | B-3 |
| 1-131 | 5a-1 | A-43 | B-3 |
| 1-132 | 5a-1 | A-44 | B-3 |
| 1-133 | 5a-1 | A-1 | B-4 |
| 1-134 | 5a-1 | A-2 | B-4 |
| 1-135 | 5a-1 | A-3 | B-4 |
| 1-136 | 5a-1 | A-4 | B-4 |
| 1-137 | 5a-1 | A-5 | B-4 |
| 1-138 | 5a-1 | A-6 | B-4 |

TABLE 2

| Cmpd No. | Grp 4 | X¹ | X² |
| --- | --- | --- | --- |
| 1-139 | 5a-1 | A-7 | B-4 |
| 1-140 | 5a-1 | A-8 | B-4 |
| 1-141 | 5a-1 | A-9 | B-4 |
| 1-142 | 5a-1 | A-10 | B-4 |
| 1-143 | 5a-1 | A-11 | B-4 |
| 1-144 | 5a-1 | A-12 | B-4 |
| 1-145 | 5a-1 | A-13 | B-4 |
| 1-146 | 5a-1 | A-14 | B-4 |
| 1-147 | 5a-1 | A-15 | B-4 |
| 1-148 | 5a-1 | A-16 | B-4 |
| 1-149 | 5a-1 | A-17 | B-4 |
| 1-150 | 5a-1 | A-18 | B-4 |
| 1-151 | 5a-1 | A-19 | B-4 |
| 1-152 | 5a-1 | A-20 | B-4 |
| 1-153 | 5a-1 | A-21 | B-4 |
| 1-154 | 5a-1 | A-22 | B-4 |
| 1-155 | 5a-1 | A-23 | B-4 |
| 1-156 | 5a-1 | A-24 | B-4 |
| 1-157 | 5a-1 | A-25 | B-4 |
| 1-158 | 5a-1 | A-26 | B-4 |
| 1-159 | 5a-1 | A-27 | B-4 |
| 1-160 | 5a-1 | A-28 | B-4 |
| 1-161 | 5a-1 | A-29 | B-4 |
| 1-162 | 5a-1 | A-30 | B-4 |
| 1-163 | 5a-1 | A-31 | B-4 |
| 1-164 | 5a-1 | A-32 | B-4 |
| 1-165 | 5a-1 | A-33 | B-4 |
| 1-166 | 5a-1 | A-34 | B-4 |
| 1-167 | 5a-1 | A-35 | B-4 |
| 1-168 | 5a-1 | A-36 | B-4 |
| 1-169 | 5a-1 | A-37 | B-4 |
| 1-170 | 5a-1 | A-38 | B-4 |
| 1-171 | 5a-1 | A-39 | B-4 |
| 1-172 | 5a-1 | A-40 | B-4 |
| 1-173 | 5a-1 | A-41 | B-4 |
| 1-174 | 5a-1 | A-42 | B-4 |
| 1-175 | 5a-1 | A-43 | B-4 |
| 1-176 | 5a-1 | A-44 | B-4 |
| 1-177 | 5a-2 | A-1 | B-1 |
| 1-178 | 5a-2 | A-2 | B-1 |
| 1-179 | 5a-2 | A-3 | B-1 |
| 1-180 | 5a-2 | A-4 | B-1 |
| 1-181 | 5a-2 | A-5 | B-1 |
| 1-182 | 5a-2 | A-6 | B-1 |
| 1-183 | 5a-2 | A-7 | B-1 |
| 1-184 | 5a-2 | A-8 | B-1 |
| 1-185 | 5a-2 | A-9 | B-1 |
| 1-186 | 5a-2 | A-10 | B-1 |
| 1-187 | 5a-2 | A-11 | B-1 |
| 1-188 | 5a-2 | A-12 | B-1 |
| 1-189 | 5a-2 | A-13 | B-1 |
| 1-190 | 5a-2 | A-14 | B-1 |
| 1-191 | 5a-2 | A-15 | B-1 |
| 1-192 | 5a-2 | A-16 | B-1 |
| 1-193 | 5a-2 | A-17 | B-1 |

TABLE 2-continued

| Cmpd No. | Grp 4 | X¹ | X² |
| --- | --- | --- | --- |
| 1-194 | 5a-2 | A-18 | B-1 |
| 1-195 | 5a-2 | A-19 | B-1 |
| 1-196 | 5a-2 | A-20 | B-1 |
| 1-197 | 5a-2 | A-21 | B-1 |
| 1-198 | 5a-2 | A-22 | B-1 |
| 1-199 | 5a-2 | A-23 | B-1 |
| 1-200 | 5a-2 | A-24 | B-1 |
| 1-201 | 5a-2 | A-25 | B-1 |
| 1-202 | 5a-2 | A-26 | B-1 |
| 1-203 | 5a-2 | A-27 | B-1 |
| 1-204 | 5a-2 | A-28 | B-1 |
| 1-205 | 5a-2 | A-29 | B-1 |
| 1-206 | 5a-2 | A-30 | B-1 |
| 1-207 | 5a-2 | A-31 | B-1 |
| 1-208 | 5a-2 | A-32 | B-1 |
| 1-209 | 5a-2 | A-33 | B-1 |
| 1-210 | 5a-2 | A-34 | B-1 |
| 1-211 | 5a-2 | A-35 | B-1 |
| 1-212 | 5a-2 | A-36 | B-1 |
| 1-213 | 5a-2 | A-37 | B-1 |
| 1-214 | 5a-2 | A-38 | B-1 |
| 1-215 | 5a-2 | A-39 | B-1 |
| 1-216 | 5a-2 | A-40 | B-1 |
| 1-217 | 5a-2 | A-41 | B-1 |
| 1-218 | 5a-2 | A-42 | B-1 |
| 1-219 | 5a-2 | A-43 | B-1 |
| 1-220 | 5a-2 | A-44 | B-1 |
| 1-221 | 5a-2 | A-1 | B-2 |
| 1-222 | 5a-2 | A-2 | B-2 |
| 1-223 | 5a-2 | A-3 | B-2 |
| 1-224 | 5a-2 | A-4 | B-2 |
| 1-225 | 5a-2 | A-5 | B-2 |
| 1-226 | 5a-2 | A-6 | B-2 |
| 1-227 | 5a-2 | A-7 | B-2 |
| 1-228 | 5a-2 | A-8 | B-2 |
| 1-229 | 5a-2 | A-9 | B-2 |
| 1-230 | 5a-2 | A-10 | B-2 |
| 1-231 | 5a-2 | A-11 | B-2 |
| 1-232 | 5a-2 | A-12 | B-2 |
| 1-233 | 5a-2 | A-13 | B-2 |
| 1-234 | 5a-2 | A-14 | B-2 |
| 1-235 | 5a-2 | A-15 | B-2 |
| 1-236 | 5a-2 | A-16 | B-2 |
| 1-237 | 5a-2 | A-17 | B-2 |
| 1-238 | 5a-2 | A-18 | B-2 |
| 1-239 | 5a-2 | A-19 | B-2 |
| 1-240 | 5a-2 | A-20 | B-2 |
| 1-241 | 5a-2 | A-21 | B-2 |
| 1-242 | 5a-2 | A-22 | B-2 |
| 1-243 | 5a-2 | A-23 | B-2 |
| 1-244 | 5a-2 | A-24 | B-2 |
| 1-245 | 5a-2 | A-25 | B-2 |
| 1-246 | 5a-2 | A-26 | B-2 |
| 1-247 | 5a-2 | A-27 | B-2 |
| 1-248 | 5a-2 | A-28 | B-2 |
| 1-249 | 5a-2 | A-29 | B-2 |
| 1-250 | 5a-2 | A-30 | B-2 |
| 1-251 | 5a-2 | A-31 | B-2 |
| 1-252 | 5a-2 | A-32 | B-2 |
| 1-253 | 5a-2 | A-33 | B-2 |
| 1-254 | 5a-2 | A-34 | B-2 |
| 1-255 | 5a-2 | A-35 | B-2 |
| 1-256 | 5a-2 | A-36 | B-2 |
| 1-257 | 5a-2 | A-37 | B-2 |
| 1-258 | 5a-2 | A-38 | B-2 |
| 1-259 | 5a-2 | A-39 | B-2 |
| 1-260 | 5a-2 | A-40 | B-2 |
| 1-261 | 5a-2 | A-41 | B-2 |
| 1-262 | 5a-2 | A-42 | B-2 |
| 1-263 | 5a-2 | A-43 | B-2 |
| 1-264 | 5a-2 | A-44 | B-2 |
| 1-265 | 5a-2 | A-1 | B-3 |
| 1-266 | 5a-2 | A-2 | B-3 |
| 1-267 | 5a-2 | A-3 | B-3 |
| 1-268 | 5a-2 | A-4 | B-3 |
| 1-269 | 5a-2 | A-5 | B-3 |
| 1-270 | 5a-2 | A-6 | B-3 |

TABLE 2-continued

| Cmpd No. | Grp 4 | $X^1$ | $X^2$ |
| --- | --- | --- | --- |
| 1-271 | 5a-2 | A-7 | B-3 |
| 1-272 | 5a-2 | A-8 | B-3 |
| 1-273 | 5a-2 | A-9 | B-3 |
| 1-274 | 5a-2 | A-10 | B-3 |
| 1-275 | 5a-2 | A-11 | B-3 |
| 1-276 | 5a-2 | A-12 | B-3 |

TABLE 3

| Cmpd No. | Grp 4 | $X^1$ | $X^2$ |
| --- | --- | --- | --- |
| 1-277 | 5a-2 | A-13 | B-3 |
| 1-278 | 5a-2 | A-14 | B-3 |
| 1-279 | 5a-2 | A-15 | B-3 |
| 1-280 | 5a-2 | A-16 | B-3 |
| 1-281 | 5a-2 | A-17 | B-3 |
| 1-282 | 5a-2 | A-18 | B-3 |
| 1-283 | 5a-2 | A-19 | B-3 |
| 1-284 | 5a-2 | A-20 | B-3 |
| 1-285 | 5a-2 | A-21 | B-3 |
| 1-286 | 5a-2 | A-22 | B-3 |
| 1-287 | 5a-2 | A-23 | B-3 |
| 1-288 | 5a-2 | A-24 | B-3 |
| 1-289 | 5a-2 | A-25 | B-3 |
| 1-290 | 5a-2 | A-26 | B-3 |
| 1-291 | 5a-2 | A-27 | B-3 |
| 1-292 | 5a-2 | A-28 | B-3 |
| 1-293 | 5a-2 | A-29 | B-3 |
| 1-294 | 5a-2 | A-30 | B-3 |
| 1-295 | 5a-2 | A-31 | B-3 |
| 1-296 | 5a-2 | A-32 | B-3 |
| 1-297 | 5a-2 | A-33 | B-3 |
| 1-298 | 5a-2 | A-34 | B-3 |
| 1-299 | 5a-2 | A-35 | B-3 |
| 1-300 | 5a-2 | A-36 | B-3 |
| 1-301 | 5a-2 | A-37 | B-3 |
| 1-302 | 5a-2 | A-38 | B-3 |
| 1-303 | 5a-2 | A-39 | B-3 |
| 1-304 | 5a-2 | A-40 | B-3 |
| 1-305 | 5a-2 | A-41 | B-3 |
| 1-306 | 5a-2 | A-42 | B-3 |
| 1-307 | 5a-2 | A-43 | B-3 |
| 1-308 | 5a-2 | A-44 | B-3 |
| 1-309 | 5a-2 | A-1 | B-4 |
| 1-310 | 5a-2 | A-2 | B-4 |
| 1-311 | 5a-2 | A-3 | B-4 |
| 1-312 | 5a-2 | A-4 | B-4 |
| 1-313 | 5a-2 | A-5 | B-4 |
| 1-314 | 5a-2 | A-6 | B-4 |
| 1-315 | 5a-2 | A-7 | B-4 |
| 1-316 | 5a-2 | A-8 | B-4 |
| 1-317 | 5a-2 | A-9 | B-4 |
| 1-318 | 5a-2 | A-10 | B-4 |
| 1-319 | 5a-2 | A-11 | B-4 |
| 1-320 | 5a-2 | A-12 | B-4 |
| 1-321 | 5a-2 | A-13 | B-4 |
| 1-322 | 5a-2 | A-14 | B-4 |
| 1-323 | 5a-2 | A-15 | B-4 |
| 1-324 | 5a-2 | A-16 | B-4 |
| 1-325 | 5a-2 | A-17 | B-4 |
| 1-326 | 5a-2 | A-18 | B-4 |
| 1-327 | 5a-2 | A-19 | B-4 |
| 1-328 | 5a-2 | A-20 | B-4 |
| 1-329 | 5a-2 | A-21 | B-4 |
| 1-330 | 5a-2 | A-22 | B-4 |
| 1-331 | 5a-2 | A-23 | B-4 |
| 1-332 | 5a-2 | A-24 | B-4 |
| 1-333 | 5a-2 | A-25 | B-4 |
| 1-334 | 5a-2 | A-26 | B-4 |
| 1-335 | 5a-2 | A-27 | B-4 |
| 1-336 | 5a-2 | A-28 | B-4 |
| 1-337 | 5a-2 | A-29 | B-4 |
| 1-338 | 5a-2 | A-30 | B-4 |
| 1-339 | 5a-2 | A-31 | B-4 |
| 1-340 | 5a-2 | A-32 | B-4 |
| 1-341 | 5a-2 | A-33 | B-4 |
| 1-342 | 5a-2 | A-34 | B-4 |
| 1-343 | 5a-2 | A-35 | B-4 |
| 1-344 | 5a-2 | A-36 | B-4 |
| 1-345 | 5a-2 | A-37 | B-4 |
| 1-346 | 5a-2 | A-38 | B-4 |
| 1-347 | 5a-2 | A-39 | B-4 |
| 1-348 | 5a-2 | A-40 | B-4 |
| 1-349 | 5a-2 | A-41 | B-4 |
| 1-350 | 5a-2 | A-42 | B-4 |
| 1-351 | 5a-2 | A-43 | B-4 |
| 1-352 | 5a-2 | A-44 | B-4 |
| 1-353 | 5b-1 | A-1 | B-1 |
| 1-354 | 5b-1 | A-2 | B-1 |
| 1-355 | 5b-1 | A-3 | B-1 |
| 1-356 | 5b-1 | A-4 | B-1 |
| 1-357 | 5b-1 | A-5 | B-1 |
| 1-358 | 5b-1 | A-6 | B-1 |
| 1-359 | 5b-1 | A-7 | B-1 |
| 1-360 | 5b-1 | A-8 | B-1 |
| 1-361 | 5b-1 | A-9 | B-1 |
| 1-362 | 5b-1 | A-10 | B-1 |
| 1-363 | 5b-1 | A-11 | B-1 |
| 1-364 | 5b-1 | A-12 | B-1 |
| 1-365 | 5b-1 | A-13 | B-1 |
| 1-366 | 5b-1 | A-14 | B-1 |
| 1-367 | 5b-1 | A-15 | B-1 |
| 1-368 | 5b-1 | A-16 | B-1 |
| 1-369 | 5b-1 | A-17 | B-1 |
| 1-370 | 5b-1 | A-18 | B-1 |
| 1-371 | 5b-1 | A-19 | B-1 |
| 1-372 | 5b-1 | A-20 | B-1 |
| 1-373 | 5b-1 | A-21 | B-1 |
| 1-374 | 5b-1 | A-22 | B-1 |
| 1-375 | 5b-1 | A-23 | B-1 |
| 1-376 | 5b-1 | A-24 | B-1 |
| 1-377 | 5b-1 | A-25 | B-1 |
| 1-378 | 5b-1 | A-26 | B-1 |
| 1-379 | 5b-1 | A-27 | B-1 |
| 1-380 | 5b-1 | A-28 | B-1 |
| 1-381 | 5b-1 | A-29 | B-1 |
| 1-382 | 5b-1 | A-30 | B-1 |
| 1-383 | 5b-1 | A-31 | B-1 |
| 1-384 | 5b-1 | A-32 | B-1 |
| 1-385 | 5b-1 | A-33 | B-1 |
| 1-386 | 5b-1 | A-34 | B-1 |
| 1-387 | 5b-1 | A-35 | B-1 |
| 1-388 | 5b-1 | A-36 | B-1 |
| 1-389 | 5b-1 | A-37 | B-1 |
| 1-390 | 5b-1 | A-38 | B-1 |
| 1-391 | 5b-1 | A-39 | B-1 |
| 1-392 | 5b-1 | A-40 | B-1 |
| 1-393 | 5b-1 | A-41 | B-1 |
| 1-394 | 5b-1 | A-42 | B-1 |
| 1-395 | 5b-1 | A-43 | B-1 |
| 1-396 | 5b-1 | A-44 | B-1 |
| 1-397 | 5b-1 | A-1 | B-2 |
| 1-398 | 5b-1 | A-2 | B-2 |
| 1-399 | 5b-1 | A-3 | B-2 |
| 1-400 | 5b-1 | A-4 | B-2 |
| 1-401 | 5b-1 | A-5 | B-2 |
| 1-402 | 5b-1 | A-6 | B-2 |
| 1-403 | 5b-1 | A-7 | B-2 |
| 1-404 | 5b-1 | A-8 | B-2 |
| 1-405 | 5b-1 | A-9 | B-2 |
| 1-406 | 5b-1 | A-10 | B-2 |
| 1-407 | 5b-1 | A-11 | B-2 |
| 1-408 | 5b-1 | A-12 | B-2 |
| 1-409 | 5b-1 | A-13 | B-2 |
| 1-410 | 5b-1 | A-14 | B-2 |
| 1-411 | 5b-1 | A-15 | B-2 |
| 1-412 | 5b-1 | A-16 | B-2 |
| 1-413 | 5b-1 | A-17 | B-2 |
| 1-414 | 5b-1 | A-18 | B-2 |

TABLE 4

| Cmpd No. | Grp 4 | X¹ | X² |
|---|---|---|---|
| 1-415 | 5b-1 | A-19 | B-2 |
| 1-416 | 5b-1 | A-20 | B-2 |
| 1-417 | 5b-1 | A-21 | B-2 |
| 1-418 | 5b-1 | A-22 | B-2 |
| 1-419 | 5b-1 | A-23 | B-2 |
| 1-420 | 5b-1 | A-24 | B-2 |
| 1-421 | 5b-1 | A-25 | B-2 |
| 1-422 | 5b-1 | A-26 | B-2 |
| 1-423 | 5b-1 | A-27 | B-2 |
| 1-424 | 5b-1 | A-28 | B-2 |
| 1-425 | 5b-1 | A-29 | B-2 |
| 1-426 | 5b-1 | A-30 | B-2 |
| 1-427 | 5b-1 | A-31 | B-2 |
| 1-428 | 5b-1 | A-32 | B-2 |
| 1-429 | 5b-1 | A-33 | B-2 |
| 1-430 | 5b-1 | A-34 | B-2 |
| 1-431 | 5b-1 | A-35 | B-2 |
| 1-432 | 5b-1 | A-36 | B-2 |
| 1-433 | 5b-1 | A-37 | B-2 |
| 1-434 | 5b-1 | A-38 | B-2 |
| 1-435 | 5b-1 | A-39 | B-2 |
| 1-436 | 5b-1 | A-40 | B-2 |
| 1-437 | 5b-1 | A-41 | B-2 |
| 1-438 | 5b-1 | A-42 | B-2 |
| 1-439 | 5b-1 | A-43 | B-2 |
| 1-440 | 5b-1 | A-44 | B-2 |
| 1-441 | 5b-1 | A-1 | B-3 |
| 1-442 | 5b-1 | A-2 | B-3 |
| 1-443 | 5b-1 | A-3 | B-3 |
| 1-444 | 5b-1 | A-4 | B-3 |
| 1-445 | 5b-1 | A-5 | B-3 |
| 1-446 | 5b-1 | A-6 | B-3 |
| 1-447 | 5b-1 | A-7 | B-3 |
| 1-448 | 5b-1 | A-8 | B-3 |
| 1-449 | 5b-1 | A-9 | B-3 |
| 1-450 | 5b-1 | A-10 | B-3 |
| 1-451 | 5b-1 | A-11 | B-3 |
| 1-452 | 5b-1 | A-12 | B-3 |
| 1-453 | 5b-1 | A-13 | B-3 |
| 1-454 | 5b-1 | A-14 | B-3 |
| 1-455 | 5b-1 | A-15 | B-3 |
| 1-456 | 5b-1 | A-16 | B-3 |
| 1-457 | 5b-1 | A-17 | B-3 |
| 1-458 | 5b-1 | A-18 | B-3 |
| 1-459 | 5b-1 | A-19 | B-3 |
| 1-460 | 5b-1 | A-20 | B-3 |
| 1-461 | 5b-1 | A-21 | B-3 |
| 1-462 | 5b-1 | A-22 | B-3 |
| 1-463 | 5b-1 | A-23 | B-3 |
| 1-464 | 5b-1 | A-24 | B-3 |
| 1-465 | 5b-1 | A-25 | B-3 |
| 1-466 | 5b-1 | A-26 | B-3 |
| 1-467 | 5b-1 | A-27 | B-3 |
| 1-468 | 5b-1 | A-28 | B-3 |
| 1-469 | 5b-1 | A-29 | B-3 |
| 1-470 | 5b-1 | A-30 | B-3 |
| 1-471 | 5b-1 | A-31 | B-3 |
| 1-472 | 5b-1 | A-32 | B-3 |
| 1-473 | 5b-1 | A-33 | B-3 |
| 1-474 | 5b-1 | A-34 | B-3 |
| 1-475 | 5b-1 | A-35 | B-3 |
| 1-476 | 5b-1 | A-36 | B-3 |
| 1-477 | 5b-1 | A-37 | B-3 |
| 1-478 | 5b-1 | A-38 | B-3 |
| 1-479 | 5b-1 | A-39 | B-3 |
| 1-480 | 5b-1 | A-40 | B-3 |
| 1-481 | 5b-1 | A-41 | B-3 |
| 1-482 | 5b-1 | A-42 | B-3 |
| 1-483 | 5b-1 | A-43 | B-3 |
| 1-484 | 5b-1 | A-44 | B-3 |
| 1-485 | 5b-1 | A-1 | B-4 |
| 1-486 | 5b-1 | A-2 | B-4 |
| 1-487 | 5b-1 | A-3 | B-4 |
| 1-488 | 5b-1 | A-4 | B-4 |
| 1-489 | 5b-1 | A-5 | B-4 |
| 1-490 | 5b-1 | A-6 | B-4 |
| 1-491 | 5b-1 | A-7 | B-4 |
| 1-492 | 5b-1 | A-8 | B-4 |
| 1-493 | 5b-1 | A-9 | B-4 |
| 1-494 | 5b-1 | A-10 | B-4 |
| 1-495 | 5b-1 | A-11 | B-4 |
| 1-496 | 5b-1 | A-12 | B-4 |
| 1-497 | 5b-1 | A-13 | B-4 |
| 1-498 | 5b-1 | A-14 | B-4 |
| 1-499 | 5b-1 | A-15 | B-4 |
| 1-500 | 5b-1 | A-16 | B-4 |
| 1-501 | 5b-1 | A-17 | B-4 |
| 1-502 | 5b-1 | A-18 | B-4 |
| 1-503 | 5b-1 | A-19 | B-4 |
| 1-504 | 5b-1 | A-20 | B-4 |
| 1-505 | 5b-1 | A-21 | B-4 |
| 1-506 | 5b-1 | A-22 | B-4 |
| 1-507 | 5b-1 | A-23 | B-4 |
| 1-508 | 5b-1 | A-24 | B-4 |
| 1-509 | 5b-1 | A-25 | B-4 |
| 1-510 | 5b-1 | A-26 | B-4 |
| 1-511 | 5b-1 | A-27 | B-4 |
| 1-512 | 5b-1 | A-28 | B-4 |
| 1-513 | 5b-1 | A-29 | B-4 |
| 1-514 | 5b-1 | A-30 | B-4 |
| 1-515 | 5b-1 | A-31 | B-4 |
| 1-516 | 5b-1 | A-32 | B-4 |
| 1-517 | 5b-1 | A-33 | B-4 |
| 1-518 | 5b-1 | A-34 | B-4 |
| 1-519 | 5b-1 | A-35 | B-4 |
| 1-520 | 5b-1 | A-36 | B-4 |
| 1-521 | 5b-1 | A-37 | B-4 |
| 1-522 | 5b-1 | A-38 | B-4 |
| 1-523 | 5b-1 | A-39 | B-4 |
| 1-524 | 5b-1 | A-40 | B-4 |
| 1-525 | 5b-1 | A-41 | B-4 |
| 1-526 | 5b-1 | A-42 | B-4 |
| 1-527 | 5b-1 | A-43 | B-4 |
| 1-528 | 5b-1 | A-44 | B-4 |
| 1-529 | 5b-2 | A-1 | B-1 |
| 1-530 | 5b-2 | A-2 | B-1 |
| 1-531 | 5b-2 | A-3 | B-1 |
| 1-532 | 5b-2 | A-4 | B-1 |
| 1-533 | 5b-2 | A-5 | B-1 |
| 1-534 | 5b-2 | A-6 | B-1 |
| 1-535 | 5b-2 | A-7 | B-1 |
| 1-536 | 5b-2 | A-8 | B-1 |
| 1-537 | 5b-2 | A-9 | B-1 |
| 1-538 | 5b-2 | A-10 | B-1 |
| 1-539 | 5b-2 | A-11 | B-1 |
| 1-540 | 5b-2 | A-12 | B-1 |
| 1-541 | 5b-2 | A-13 | B-1 |
| 1-542 | 5b-2 | A-14 | B-1 |
| 1-543 | 5b-2 | A-15 | B-1 |
| 1-544 | 5b-2 | A-16 | B-1 |
| 1-545 | 5b-2 | A-17 | B-1 |
| 1-546 | 5b-2 | A-18 | B-1 |
| 1-547 | 5b-2 | A-19 | B-1 |
| 1-548 | 5b-2 | A-20 | B-1 |
| 1-549 | 5b-2 | A-21 | B-1 |
| 1-550 | 5b-2 | A-22 | B-1 |
| 1-551 | 5b-2 | A-23 | B-1 |
| 1-552 | 5b-2 | A-24 | B-1 |

TABLE 5

| Cmpd No. | Grp 4 | X¹ | X² |
|---|---|---|---|
| 1-553 | 5b-2 | A-25 | B-1 |
| 1-554 | 5b-2 | A-26 | B-1 |
| 1-555 | 5b-2 | A-27 | B-1 |
| 1-556 | 5b-2 | A-28 | B-1 |
| 1-557 | 5b-2 | A-29 | B-1 |
| 1-558 | 5b-2 | A-30 | B-1 |
| 1-559 | 5b-2 | A-31 | B-1 |

TABLE 5-continued

| Cmpd No. | Grp 4 | $X^1$ | $X^2$ |
| --- | --- | --- | --- |
| 1-560 | 5b-2 | A-32 | B-1 |
| 1-561 | 5b-2 | A-33 | B-1 |
| 1-562 | 5b-2 | A-34 | B-1 |
| 1-563 | 5b-2 | A-35 | B-1 |
| 1-564 | 5b-2 | A-36 | B-1 |
| 1-565 | 5b-2 | A-37 | B-1 |
| 1-566 | 5b-2 | A-38 | B-1 |
| 1-567 | 5b-2 | A-39 | B-1 |
| 1-568 | 5b-2 | A-40 | B-1 |
| 1-569 | 5b-2 | A-41 | B-1 |
| 1-570 | 5b-2 | A-42 | B-1 |
| 1-571 | 5b-2 | A-43 | B-1 |
| 1-572 | 5b-2 | A-44 | B-1 |
| 1-573 | 5b-2 | A-1 | B-2 |
| 1-574 | 5b-2 | A-2 | B-2 |
| 1-575 | 5b-2 | A-3 | B-2 |
| 1-576 | 5b-2 | A-4 | B-2 |
| 1-577 | 5b-2 | A-5 | B-2 |
| 1-578 | 5b-2 | A-6 | B-2 |
| 1-579 | 5b-2 | A-7 | B-2 |
| 1-580 | 5b-2 | A-8 | B-2 |
| 1-581 | 5b-2 | A-9 | B-2 |
| 1-582 | 5b-2 | A-10 | B-2 |
| 1-583 | 5b-2 | A-11 | B-2 |
| 1-584 | 5b-2 | A-12 | B-2 |
| 1-585 | 5b-2 | A-13 | B-2 |
| 1-586 | 5b-2 | A-14 | B-2 |
| 1-587 | 5b-2 | A-15 | B-2 |
| 1-588 | 5b-2 | A-16 | B-2 |
| 1-589 | 5b-2 | A-17 | B-2 |
| 1-590 | 5b-2 | A-18 | B-2 |
| 1-591 | 5b-2 | A-19 | B-2 |
| 1-592 | 5b-2 | A-20 | B-2 |
| 1-593 | 5b-2 | A-21 | B-2 |
| 1-594 | 5b-2 | A-22 | B-2 |
| 1-595 | 5b-2 | A-23 | B-2 |
| 1-596 | 5b-2 | A-24 | B-2 |
| 1-597 | 5b-2 | A-25 | B-2 |
| 1-598 | 5b-2 | A-26 | B-2 |
| 1-599 | 5b-2 | A-27 | B-2 |
| 1-600 | 5b-2 | A-28 | B-2 |
| 1-601 | 5b-2 | A-29 | B-2 |
| 1-602 | 5b-2 | A-30 | B-2 |
| 1-603 | 5b-2 | A-31 | B-2 |
| 1-604 | 5b-2 | A-32 | B-2 |
| 1-605 | 5b-2 | A-33 | B-2 |
| 1-606 | 5b-2 | A-34 | B-2 |
| 1-607 | 5b-2 | A-35 | B-2 |
| 1-608 | 5b-2 | A-36 | B-2 |
| 1-609 | 5b-2 | A-37 | B-2 |
| 1-610 | 5b-2 | A-38 | B-2 |
| 1-611 | 5b-2 | A-39 | B-2 |
| 1-612 | 5b-2 | A-40 | B-2 |
| 1-613 | 5b-2 | A-41 | B-2 |
| 1-614 | 5b-2 | A-42 | B-2 |
| 1-615 | 5b-2 | A-43 | B-2 |
| 1-616 | 5b-2 | A-44 | B-2 |
| 1-617 | 5b-2 | A-1 | B-3 |
| 1-618 | 5b-2 | A-2 | B-3 |
| 1-619 | 5b-2 | A-3 | B-3 |
| 1-620 | 5b-2 | A-4 | B-3 |
| 1-621 | 5b-2 | A-5 | B-3 |
| 1-622 | 5b-2 | A-6 | B-3 |
| 1-623 | 5b-2 | A-7 | B-3 |
| 1-624 | 5b-2 | A-8 | B-3 |
| 1-625 | 5b-2 | A-9 | B-3 |
| 1-626 | 5b-2 | A-10 | B-3 |
| 1-627 | 5b-2 | A-11 | B-3 |
| 1-628 | 5b-2 | A-12 | B-3 |
| 1-629 | 5b-2 | A-13 | B-3 |
| 1-630 | 5b-2 | A-14 | B-3 |
| 1-631 | 5b-2 | A-15 | B-3 |
| 1-632 | 5b-2 | A-16 | B-3 |
| 1-633 | 5b-2 | A-17 | B-3 |
| 1-634 | 5b-2 | A-18 | B-3 |
| 1-635 | 5b-2 | A-19 | B-3 |
| 1-636 | 5b-2 | A-20 | B-3 |
| 1-637 | 5b-2 | A-21 | B-3 |
| 1-638 | 5b-2 | A-22 | B-3 |
| 1-639 | 5b-2 | A-23 | B-3 |
| 1-640 | 5b-2 | A-24 | B-3 |
| 1-641 | 5b-2 | A-25 | B-3 |
| 1-642 | 5b-2 | A-26 | B-3 |
| 1-643 | 5b-2 | A-27 | B-3 |
| 1-644 | 5b-2 | A-28 | B-3 |
| 1-645 | 5b-2 | A-29 | B-3 |
| 1-646 | 5b-2 | A-30 | B-3 |
| 1-647 | 5b-2 | A-31 | B-3 |
| 1-648 | 5b-2 | A-32 | B-3 |
| 1-649 | 5b-2 | A-33 | B-3 |
| 1-650 | 5b-2 | A-34 | B-3 |
| 1-651 | 5b-2 | A-35 | B-3 |
| 1-652 | 5b-2 | A-36 | B-3 |
| 1-653 | 5b-2 | A-37 | B-3 |
| 1-654 | 5b-2 | A-38 | B-3 |
| 1-655 | 5b-2 | A-39 | B-3 |
| 1-656 | 5b-2 | A-40 | B-3 |
| 1-657 | 5b-2 | A-41 | B-3 |
| 1-658 | 5b-2 | A-42 | B-3 |
| 1-659 | 5b-2 | A-43 | B-3 |
| 1-660 | 5b-2 | A-44 | B-3 |
| 1-661 | 5b-2 | A-1 | B-4 |
| 1-662 | 5b-2 | A-2 | B-4 |
| 1-663 | 5b-2 | A-3 | B-4 |
| 1-664 | 5b-2 | A-4 | B-4 |
| 1-665 | 5b-2 | A-5 | B-4 |
| 1-666 | 5b-2 | A-6 | B-4 |
| 1-667 | 5b-2 | A-7 | B-4 |
| 1-668 | 5b-2 | A-8 | B-4 |
| 1-669 | 5b-2 | A-9 | B-4 |
| 1-670 | 5b-2 | A-10 | B-4 |
| 1-671 | 5b-2 | A-11 | B-4 |
| 1-672 | 5b-2 | A-12 | B-4 |
| 1-673 | 5b-2 | A-13 | B-4 |
| 1-674 | 5b-2 | A-14 | B-4 |
| 1-675 | 5b-2 | A-15 | B-4 |
| 1-676 | 5b-2 | A-16 | B-4 |
| 1-677 | 5b-2 | A-17 | B-4 |
| 1-678 | 5b-2 | A-18 | B-4 |
| 1-679 | 5b-2 | A-19 | B-4 |
| 1-680 | 5b-2 | A-20 | B-4 |
| 1-681 | 5b-2 | A-21 | B-4 |
| 1-682 | 5b-2 | A-22 | B-4 |
| 1-683 | 5b-2 | A-23 | B-4 |
| 1-684 | 5b-2 | A-24 | B-4 |
| 1-685 | 5b-2 | A-25 | B-4 |
| 1-686 | 5b-2 | A-26 | B-4 |
| 1-687 | 5b-2 | A-27 | B-4 |
| 1-688 | 5b-2 | A-28 | B-4 |
| 1-689 | 5b-2 | A-29 | B-4 |
| 1-690 | 5b-2 | A-30 | B-4 |

TABLE 6

| Cmpd No. | Grp 4 | $X^1$ | $X^2$ |
| --- | --- | --- | --- |
| 1-691 | 5b-2 | A-31 | B-4 |
| 1-692 | 5b-2 | A-32 | B-4 |
| 1-693 | 5b-2 | A-33 | B-4 |
| 1-694 | 5b-2 | A-34 | B-4 |
| 1-695 | 5b-2 | A-35 | B-4 |
| 1-696 | 5b-2 | A-36 | B-4 |
| 1-697 | 5b-2 | A-37 | B-4 |
| 1-698 | 5b-2 | A-38 | B-4 |
| 1-699 | 5b-2 | A-39 | B-4 |
| 1-700 | 5b-2 | A-40 | B-4 |
| 1-701 | 5b-2 | A-41 | B-4 |
| 1-702 | 5b-2 | A-42 | B-4 |
| 1-703 | 5b-2 | A-43 | B-4 |
| 1-704 | 5b-2 | A-44 | B-4 |

TABLE 6-continued

| Cmpd No. | Grp 4 | $X^1$ | $X^2$ |
| --- | --- | --- | --- |
| 1-705 | 5c-1 | A-1 | B-1 |
| 1-706 | 5c-1 | A-2 | B-1 |
| 1-707 | 5c-1 | A-3 | B-1 |
| 1-708 | 5c-1 | A-4 | B-1 |
| 1-709 | 5c-1 | A-5 | B-1 |
| 1-710 | 5c-1 | A-6 | B-1 |
| 1-711 | 5c-1 | A-7 | B-1 |
| 1-712 | 5c-1 | A-8 | B-1 |
| 1-713 | 5c-1 | A-9 | B-1 |
| 1-714 | 5c-1 | A-10 | B-1 |
| 1-715 | 5c-1 | A-11 | B-1 |
| 1-716 | 5c-1 | A-12 | B-1 |
| 1-717 | 5c-1 | A-13 | B-1 |
| 1-718 | 5c-1 | A-14 | B-1 |
| 1-719 | 5c-1 | A-15 | B-1 |
| 1-720 | 5c-1 | A-16 | B-1 |
| 1-721 | 5c-1 | A-17 | B-1 |
| 1-722 | 5c-1 | A-18 | B-1 |
| 1-723 | 5c-1 | A-19 | B-1 |
| 1-724 | 5c-1 | A-20 | B-1 |
| 1-725 | 5c-1 | A-21 | B-1 |
| 1-726 | 5c-1 | A-22 | B-1 |
| 1-727 | 5c-1 | A-23 | B-1 |
| 1-728 | 5c-1 | A-24 | B-1 |
| 1-729 | 5c-1 | A-25 | B-1 |
| 1-730 | 5c-1 | A-26 | B-1 |
| 1-731 | 5c-1 | A-27 | B-1 |
| 1-732 | 5c-1 | A-28 | B-1 |
| 1-733 | 5c-1 | A-29 | B-1 |
| 1-734 | 5c-1 | A-30 | B-1 |
| 1-735 | 5c-1 | A-31 | B-1 |
| 1-736 | 5c-1 | A-32 | B-1 |
| 1-737 | 5c-1 | A-33 | B-1 |
| 1-738 | 5c-1 | A-34 | B-1 |
| 1-739 | 5c-1 | A-35 | B-1 |
| 1-740 | 5c-1 | A-36 | B-1 |
| 1-741 | 5c-1 | A-37 | B-1 |
| 1-742 | 5c-1 | A-38 | B-1 |
| 1-743 | 5c-1 | A-39 | B-1 |
| 1-744 | 5c-1 | A-40 | B-1 |
| 1-745 | 5c-1 | A-41 | B-1 |
| 1-746 | 5c-1 | A-42 | B-1 |
| 1-747 | 5c-1 | A-43 | B-1 |
| 1-748 | 5c-1 | A-44 | B-1 |
| 1-749 | 5c-1 | A-1 | B-2 |
| 1-750 | 5c-1 | A-2 | B-2 |
| 1-751 | 5c-1 | A-3 | B-2 |
| 1-752 | 5c-1 | A-4 | B-2 |
| 1-753 | 5c-1 | A-5 | B-2 |
| 1-754 | 5c-1 | A-6 | B-2 |
| 1-755 | 5c-1 | A-7 | B-2 |
| 1-756 | 5c-1 | A-8 | B-2 |
| 1-757 | 5c-1 | A-9 | B-2 |
| 1-758 | 5c-1 | A-10 | B-2 |
| 1-759 | 5c-1 | A-11 | B-2 |
| 1-760 | 5c-1 | A-12 | B-2 |
| 1-761 | 5c-1 | A-13 | B-2 |
| 1-762 | 5c-1 | A-14 | B-2 |
| 1-763 | 5c-1 | A-15 | B-2 |
| 1-764 | 5c-1 | A-16 | B-2 |
| 1-765 | 5c-1 | A-17 | B-2 |
| 1-766 | 5c-1 | A-18 | B-2 |
| 1-767 | 5c-1 | A-19 | B-2 |
| 1-768 | 5c-1 | A-20 | B-2 |
| 1-769 | 5c-1 | A-21 | B-2 |
| 1-770 | 5c-1 | A-22 | B-2 |
| 1-771 | 5c-1 | A-23 | B-2 |
| 1-772 | 5c-1 | A-24 | B-2 |
| 1-773 | 5c-1 | A-25 | B-2 |
| 1-774 | 5c-1 | A-26 | B-2 |
| 1-775 | 5c-1 | A-27 | B-2 |
| 1-776 | 5c-1 | A-28 | B-2 |
| 1-777 | 5c-1 | A-29 | B-2 |
| 1-778 | 5c-1 | A-30 | B-2 |
| 1-779 | 5c-1 | A-31 | B-2 |
| 1-780 | 5c-1 | A-32 | B-2 |
| 1-781 | 5c-1 | A-33 | B-2 |
| 1-782 | 5c-1 | A-34 | B-2 |
| 1-783 | 5c-1 | A-35 | B-2 |
| 1-784 | 5c-1 | A-36 | B-2 |
| 1-785 | 5c-1 | A-37 | B-2 |
| 1-786 | 5c-1 | A-38 | B-2 |
| 1-787 | 5c-1 | A-39 | B-2 |
| 1-788 | 5c-1 | A-40 | B-2 |
| 1-789 | 5c-1 | A-41 | B-2 |
| 1-790 | 5c-1 | A-42 | B-2 |
| 1-791 | 5c-1 | A-43 | B-2 |
| 1-792 | 5c-1 | A-44 | B-2 |
| 1-793 | 5c-1 | A-1 | B-3 |
| 1-794 | 5c-1 | A-2 | B-3 |
| 1-795 | 5c-1 | A-3 | B-3 |
| 1-796 | 5c-1 | A-4 | B-3 |
| 1-797 | 5c-1 | A-5 | B-3 |
| 1-798 | 5c-1 | A-6 | B-3 |
| 1-799 | 5c-1 | A-7 | B-3 |
| 1-800 | 5c-1 | A-8 | B-3 |
| 1-801 | 5c-1 | A-9 | B-3 |
| 1-802 | 5c-1 | A-10 | B-3 |
| 1-803 | 5c-1 | A-11 | B-3 |
| 1-804 | 5c-1 | A-12 | B-3 |
| 1-805 | 5c-1 | A-13 | B-3 |
| 1-806 | 5c-1 | A-14 | B-3 |
| 1-807 | 5c-1 | A-15 | B-3 |
| 1-808 | 5c-1 | A-16 | B-3 |
| 1-809 | 5c-1 | A-17 | B-3 |
| 1-810 | 5c-1 | A-18 | B-3 |
| 1-811 | 5c-1 | A-19 | B-3 |
| 1-812 | 5c-1 | A-20 | B-3 |
| 1-813 | 5c-1 | A-21 | B-3 |
| 1-814 | 5c-1 | A-22 | B-3 |
| 1-815 | 5c-1 | A-23 | B-3 |
| 1-816 | 5c-1 | A-24 | B-3 |
| 1-817 | 5c-1 | A-25 | B-3 |
| 1-818 | 5c-1 | A-26 | B-3 |
| 1-819 | 5c-1 | A-27 | B-3 |
| 1-820 | 5c-1 | A-28 | B-3 |
| 1-821 | 5c-1 | A-29 | B-3 |
| 1-822 | 5c-1 | A-30 | B-3 |
| 1-823 | 5c-1 | A-31 | B-3 |
| 1-824 | 5c-1 | A-32 | B-3 |
| 1-825 | 5c-1 | A-33 | B-3 |
| 1-826 | 5c-1 | A-34 | B-3 |
| 1-827 | 5c-1 | A-35 | B-3 |
| 1-828 | 5c-1 | A-36 | B-3 |

TABLE 7

| Cmpd No. | Grp 4 | $X^1$ | $X^2$ |
| --- | --- | --- | --- |
| 1-829 | 5c-1 | A-37 | B-3 |
| 1-830 | 5c-1 | A-38 | B-3 |
| 1-831 | 5c-1 | A-39 | B-3 |
| 1-832 | 5c-1 | A-40 | B-3 |
| 1-833 | 5c-1 | A-41 | B-3 |
| 1-834 | 5c-1 | A-42 | B-3 |
| 1-835 | 5c-1 | A-43 | B-3 |
| 1-836 | 5c-1 | A-44 | B-3 |
| 1-837 | 5c-1 | A-1 | B-4 |
| 1-838 | 5c-1 | A-2 | B-4 |
| 1-839 | 5c-1 | A-3 | B-4 |
| 1-840 | 5c-1 | A-4 | B-4 |
| 1-841 | 5c-1 | A-5 | B-4 |
| 1-842 | 5c-1 | A-6 | B-4 |
| 1-843 | 5c-1 | A-7 | B-4 |
| 1-844 | 5c-1 | A-8 | B-4 |
| 1-845 | 5c-1 | A-9 | B-4 |
| 1-846 | 5c-1 | A-10 | B-4 |
| 1-847 | 5c-1 | A-11 | B-4 |
| 1-848 | 5c-1 | A-12 | B-4 |
| 1-849 | 5c-1 | A-13 | B-4 |

TABLE 7-continued

| Cmpd No. | Grp 4 | $X^1$ | $X^2$ |
|---|---|---|---|
| 1-850 | 5c-1 | A-14 | B-4 |
| 1-851 | 5c-1 | A-15 | B-4 |
| 1-852 | 5c-1 | A-16 | B-4 |
| 1-853 | 5c-1 | A-17 | B-4 |
| 1-854 | 5c-1 | A-18 | B-4 |
| 1-855 | 5c-1 | A-19 | B-4 |
| 1-856 | 5c-1 | A-20 | B-4 |
| 1-857 | 5c-1 | A-21 | B-4 |
| 1-858 | 5c-1 | A-22 | B-4 |
| 1-859 | 5c-1 | A-23 | B-4 |
| 1-860 | 5c-1 | A-24 | B-4 |
| 1-861 | 5c-1 | A-25 | B-4 |
| 1-862 | 5c-1 | A-26 | B-4 |
| 1-863 | 5c-1 | A-27 | B-4 |
| 1-864 | 5c-1 | A-28 | B-4 |
| 1-865 | 5c-1 | A-29 | B-4 |
| 1-866 | 5c-1 | A-30 | B-4 |
| 1-867 | 5c-1 | A-31 | B-4 |
| 1-868 | 5c-1 | A-32 | B-4 |
| 1-869 | 5c-1 | A-33 | B-4 |
| 1-870 | 5c-1 | A-34 | B-4 |
| 1-871 | 5c-1 | A-35 | B-4 |
| 1-872 | 5c-1 | A-36 | B-4 |
| 1-873 | 5c-1 | A-37 | B-4 |
| 1-874 | 5c-1 | A-38 | B-4 |
| 1-875 | 5c-1 | A-39 | B-4 |
| 1-876 | 5c-1 | A-40 | B-4 |
| 1-877 | 5c-1 | A-41 | B-4 |
| 1-878 | 5c-1 | A-42 | B-4 |
| 1-879 | 5c-1 | A-43 | B-4 |
| 1-880 | 5c-1 | A-44 | B-4 |
| 1-881 | 5c-2 | A-1 | B-1 |
| 1-882 | 5c-2 | A-2 | B-1 |
| 1-883 | 5c-2 | A-3 | B-1 |
| 1-884 | 5c-2 | A-4 | B-1 |
| 1-885 | 5c-2 | A-5 | B-1 |
| 1-886 | 5c-2 | A-6 | B-1 |
| 1-887 | 5c-2 | A-7 | B-1 |
| 1-888 | 5c-2 | A-8 | B-1 |
| 1-889 | 5c-2 | A-9 | B-1 |
| 1-890 | 5c-2 | A-10 | B-1 |
| 1-891 | 5c-2 | A-11 | B-1 |
| 1-892 | 5c-2 | A-12 | B-1 |
| 1-893 | 5c-2 | A-13 | B-1 |
| 1-894 | 5c-2 | A-14 | B-1 |
| 1-895 | 5c-2 | A-15 | B-1 |
| 1-896 | 5c-2 | A-16 | B-1 |
| 1-897 | 5c-2 | A-17 | B-1 |
| 1-898 | 5c-2 | A-18 | B-1 |
| 1-899 | 5c-2 | A-19 | B-1 |
| 1-900 | 5c-2 | A-20 | B-1 |
| 1-901 | 5c-2 | A-21 | B-1 |
| 1-902 | 5c-2 | A-22 | B-1 |
| 1-903 | 5c-2 | A-23 | B-1 |
| 1-904 | 5c-2 | A-24 | B-1 |
| 1-905 | 5c-2 | A-25 | B-1 |
| 1-906 | 5c-2 | A-26 | B-1 |
| 1-907 | 5c-2 | A-27 | B-1 |
| 1-908 | 5c-2 | A-28 | B-1 |
| 1-909 | 5c-2 | A-29 | B-1 |
| 1-910 | 5c-2 | A-30 | B-1 |
| 1-911 | 5c-2 | A-31 | B-1 |
| 1-912 | 5c-2 | A-32 | B-1 |
| 1-913 | 5c-2 | A-33 | B-1 |
| 1-914 | 5c-2 | A-34 | B-1 |
| 1-915 | 5c-2 | A-35 | B-1 |
| 1-916 | 5c-2 | A-36 | B-1 |
| 1-917 | 5c-2 | A-37 | B-1 |
| 1-918 | 5c-2 | A-38 | B-1 |
| 1-919 | 5c-2 | A-39 | B-1 |
| 1-920 | 5c-2 | A-40 | B-1 |
| 1-921 | 5c-2 | A-41 | B-1 |
| 1-922 | 5c-2 | A-42 | B-1 |
| 1-923 | 5c-2 | A-43 | B-1 |
| 1-924 | 5c-2 | A-44 | B-1 |
| 1-925 | 5c-2 | A-1 | B-2 |
| 1-926 | 5c-2 | A-2 | B-2 |

TABLE 7-continued

| Cmpd No. | Grp 4 | $X^1$ | $X^2$ |
|---|---|---|---|
| 1-927 | 5c-2 | A-3 | B-2 |
| 1-928 | 5c-2 | A-4 | B-2 |
| 1-929 | 5c-2 | A-5 | B-2 |
| 1-930 | 5c-2 | A-6 | B-2 |
| 1-931 | 5c-2 | A-7 | B-2 |
| 1-932 | 5c-2 | A-8 | B-2 |
| 1-933 | 5c-2 | A-9 | B-2 |
| 1-934 | 5c-2 | A-10 | B-2 |
| 1-935 | 5c-2 | A-11 | B-2 |
| 1-936 | 5c-2 | A-12 | B-2 |
| 1-937 | 5c-2 | A-13 | B-2 |
| 1-938 | 5c-2 | A-14 | B-2 |
| 1-939 | 5c-2 | A-15 | B-2 |
| 1-940 | 5c-2 | A-16 | B-2 |
| 1-941 | 5c-2 | A-17 | B-2 |
| 1-942 | 5c-2 | A-18 | B-2 |
| 1-943 | 5c-2 | A-19 | B-2 |
| 1-944 | 5c-2 | A-20 | B-2 |
| 1-945 | 5c-2 | A-21 | B-2 |
| 1-946 | 5c-2 | A-22 | B-2 |
| 1-947 | 5c-2 | A-23 | B-2 |
| 1-948 | 5c-2 | A-24 | B-2 |
| 1-949 | 5c-2 | A-25 | B-2 |
| 1-950 | 5c-2 | A-26 | B-2 |
| 1-951 | 5c-2 | A-27 | B-2 |
| 1-952 | 5c-2 | A-28 | B-2 |
| 1-953 | 5c-2 | A-29 | B-2 |
| 1-954 | 5c-2 | A-30 | B-2 |
| 1-955 | 5c-2 | A-31 | B-2 |
| 1-956 | 5c-2 | A-32 | B-2 |
| 1-957 | 5c-2 | A-33 | B-2 |
| 1-958 | 5c-2 | A-34 | B-2 |
| 1-959 | 5c-2 | A-35 | B-2 |
| 1-960 | 5c-2 | A-36 | B-2 |
| 1-961 | 5c-2 | A-37 | B-2 |
| 1-962 | 5c-2 | A-38 | B-2 |
| 1-963 | 5c-2 | A-39 | B-2 |
| 1-964 | 5c-2 | A-40 | B-2 |
| 1-965 | 5c-2 | A-41 | B-2 |
| 1-966 | 5c-2 | A-42 | B-2 |

TABLE 8

| Cmpd No. | Grp 4 | $X^1$ | $X^2$ |
|---|---|---|---|
| 1-967 | 5c-2 | A-43 | B-2 |
| 1-968 | 5c-2 | A-44 | B-2 |
| 1-969 | 5c-2 | A-1 | B-3 |
| 1-970 | 5c-2 | A-2 | B-3 |
| 1-971 | 5c-2 | A-3 | B-3 |
| 1-972 | 5c-2 | A-4 | B-3 |
| 1-973 | 5c-2 | A-5 | B-3 |
| 1-974 | 5c-2 | A-6 | B-3 |
| 1-975 | 5c-2 | A-7 | B-3 |
| 1-976 | 5c-2 | A-8 | B-3 |
| 1-977 | 5c-2 | A-9 | B-3 |
| 1-978 | 5c-2 | A-10 | B-3 |
| 1-979 | 5c-2 | A-11 | B-3 |
| 1-980 | 5c-2 | A-12 | B-3 |
| 1-981 | 5c-2 | A-13 | B-3 |
| 1-982 | 5c-2 | A-14 | B-3 |
| 1-983 | 5c-2 | A-15 | B-3 |
| 1-984 | 5c-2 | A-16 | B-3 |
| 1-985 | 5c-2 | A-17 | B-3 |
| 1-986 | 5c-2 | A-18 | B-3 |
| 1-987 | 5c-2 | A-19 | B-3 |
| 1-988 | 5c-2 | A-20 | B-3 |
| 1-989 | 5c-2 | A-21 | B-3 |
| 1-990 | 5c-2 | A-22 | B-3 |
| 1-991 | 5c-2 | A-23 | B-3 |
| 1-992 | 5c-2 | A-24 | B-3 |
| 1-993 | 5c-2 | A-25 | B-3 |
| 1-994 | 5c-2 | A-26 | B-3 |

TABLE 8-continued

| Cmpd No. | Grp 4 | $X^1$ | $X^2$ |
|---|---|---|---|
| 1-995 | 5c-2 | A-27 | B-3 |
| 1-996 | 5c-2 | A-28 | B-3 |
| 1-997 | 5c-2 | A-29 | B-3 |
| 1-998 | 5c-2 | A-30 | B-3 |
| 1-999 | 5c-2 | A-31 | B-3 |
| 1-1000 | 5c-2 | A-32 | B-3 |
| 1-1001 | 5c-2 | A-33 | B-3 |
| 1-1002 | 5c-2 | A-34 | B-3 |
| 1-1003 | 5c-2 | A-35 | B-3 |
| 1-1004 | 5c-2 | A-36 | B-3 |
| 1-1005 | 5c-2 | A-37 | B-3 |
| 1-1006 | 5c-2 | A-38 | B-3 |
| 1-1007 | 5c-2 | A-39 | B-3 |
| 1-1008 | 5c-2 | A-40 | B-3 |
| 1-1009 | 5c-2 | A-41 | B-3 |
| 1-1010 | 5c-2 | A-42 | B-3 |
| 1-1011 | 5c-2 | A-43 | B-3 |
| 1-1012 | 5c-2 | A-44 | B-3 |
| 1-1013 | 5c-2 | A-1 | B-4 |
| 1-1014 | 5c-2 | A-2 | B-4 |
| 1-1015 | 5c-2 | A-3 | B-4 |
| 1-1016 | 5c-2 | A-4 | B-4 |
| 1-1017 | 5c-2 | A-5 | B-4 |
| 1-1018 | 5c-2 | A-6 | B-4 |
| 1-1019 | 5c-2 | A-7 | B-4 |
| 1-1020 | 5c-2 | A-8 | B-4 |
| 1-1021 | 5c-2 | A-9 | B-4 |
| 1-1022 | 5c-2 | A-10 | B-4 |
| 1-1023 | 5c-2 | A-11 | B-4 |
| 1-1024 | 5c-2 | A-12 | B-4 |
| 1-1025 | 5c-2 | A-13 | B-4 |
| 1-1026 | 5c-2 | A-14 | B-4 |
| 1-1027 | 5c-2 | A-15 | B-4 |
| 1-1028 | 5c-2 | A-16 | B-4 |
| 1-1029 | 5c-2 | A-17 | B-4 |
| 1-1030 | 5c-2 | A-18 | B-4 |
| 1-1031 | 5c-2 | A-19 | B-4 |
| 1-1032 | 5c-2 | A-20 | B-4 |
| 1-1033 | 5c-2 | A-21 | B-4 |
| 1-1034 | 5c-2 | A-22 | B-4 |
| 1-1035 | 5c-2 | A-23 | B-4 |
| 1-1036 | 5c-2 | A-24 | B-4 |
| 1-1037 | 5c-2 | A-25 | B-4 |
| 1-1038 | 5c-2 | A-26 | B-4 |
| 1-1039 | 5c-2 | A-27 | B-4 |
| 1-1040 | 5c-2 | A-28 | B-4 |
| 1-1041 | 5c-2 | A-29 | B-4 |
| 1-1042 | 5c-2 | A-30 | B-4 |
| 1-1043 | 5c-2 | A-31 | B-4 |
| 1-1044 | 5c-2 | A-32 | B-4 |
| 1-1045 | 5c-2 | A-33 | B-4 |
| 1-1046 | 5c-2 | A-34 | B-4 |
| 1-1047 | 5c-2 | A-35 | B-4 |
| 1-1048 | 5c-2 | A-36 | B-4 |
| 1-1049 | 5c-2 | A-37 | B-4 |
| 1-1050 | 5c-2 | A-38 | B-4 |
| 1-1051 | 5c-2 | A-39 | B-4 |
| 1-1052 | 5c-2 | A-40 | B-4 |
| 1-1053 | 5c-2 | A-41 | B-4 |
| 1-1054 | 5c-2 | A-42 | B-4 |
| 1-1055 | 5c-2 | A-43 | B-4 |
| 1-1056 | 5c-2 | A-44 | B-4 |
| 1-1057 | 5c-3 | A-1 | B-1 |
| 1-1058 | 5c-3 | A-2 | B-1 |
| 1-1059 | 5c-3 | A-3 | B-1 |
| 1-1060 | 5c-3 | A-4 | B-1 |
| 1-1061 | 5c-3 | A-5 | B-1 |
| 1-1062 | 5c-3 | A-6 | B-1 |
| 1-1063 | 5c-3 | A-7 | B-1 |
| 1-1064 | 5c-3 | A-8 | B-1 |
| 1-1065 | 5c-3 | A-9 | B-1 |
| 1-1066 | 5c-3 | A-10 | B-1 |
| 1-1067 | 5c-3 | A-11 | B-1 |
| 1-1068 | 5c-3 | A-12 | B-1 |
| 1-1069 | 5c-3 | A-13 | B-1 |
| 1-1070 | 5c-3 | A-14 | B-1 |
| 1-1071 | 5c-3 | A-15 | B-1 |
| 1-1072 | 5c-3 | A-16 | B-1 |
| 1-1073 | 5c-3 | A-17 | B-1 |
| 1-1074 | 5c-3 | A-18 | B-1 |
| 1-1075 | 5c-3 | A-19 | B-1 |
| 1-1076 | 5c-3 | A-20 | B-1 |
| 1-1077 | 5c-3 | A-21 | B-1 |
| 1-1078 | 5c-3 | A-22 | B-1 |
| 1-1079 | 5c-3 | A-23 | B-1 |
| 1-1080 | 5c-3 | A-24 | B-1 |
| 1-1081 | 5c-3 | A-25 | B-1 |
| 1-1082 | 5c-3 | A-26 | B-1 |
| 1-1083 | 5c-3 | A-27 | B-1 |
| 1-1084 | 5c-3 | A-28 | B-1 |
| 1-1085 | 5c-3 | A-29 | B-1 |
| 1-1086 | 5c-3 | A-30 | B-1 |
| 1-1087 | 5c-3 | A-31 | B-1 |
| 1-1088 | 5c-3 | A-32 | B-1 |
| 1-1089 | 5c-3 | A-33 | B-1 |
| 1-1090 | 5c-3 | A-34 | B-1 |
| 1-1091 | 5c-3 | A-35 | B-1 |
| 1-1092 | 5c-3 | A-36 | B-1 |
| 1-1093 | 5c-3 | A-37 | B-1 |
| 1-1094 | 5c-3 | A-38 | B-1 |
| 1-1095 | 5c-3 | A-39 | B-1 |
| 1-1096 | 5c-3 | A-40 | B-1 |
| 1-1097 | 5c-3 | A-41 | B-1 |
| 1-1098 | 5c-3 | A-42 | B-1 |
| 1-1099 | 5c-3 | A-43 | B-1 |
| 1-1100 | 5c-3 | A-44 | B-1 |
| 1-1101 | 5c-3 | A-1 | B-2 |
| 1-1102 | 5c-3 | A-2 | B-2 |
| 1-1103 | 5c-3 | A-3 | B-2 |
| 1-1104 | 5c-3 | A-4 | B-2 |

TABLE 9

| Cmpd No. | Grp 4 | $X^1$ | $X^2$ |
|---|---|---|---|
| 1-1105 | 5c-3 | A-5 | B-2 |
| 1-1106 | 5c-3 | A-6 | B-2 |
| 1-1107 | 5c-3 | A-7 | B-2 |
| 1-1108 | 5c-3 | A-8 | B-2 |
| 1-1109 | 5c-3 | A-9 | B-2 |
| 1-1110 | 5c-3 | A-10 | B-2 |
| 1-1111 | 5c-3 | A-11 | B-2 |
| 1-1112 | 5c-3 | A-12 | B-2 |
| 1-1113 | 5c-3 | A-13 | B-2 |
| 1-1114 | 5c-3 | A-14 | B-2 |
| 1-1115 | 5c-3 | A-15 | B-2 |
| 1-1116 | 5c-3 | A-16 | B-2 |
| 1-1117 | 5c-3 | A-17 | B-2 |
| 1-1118 | 5c-3 | A-18 | B-2 |
| 1-1119 | 5c-3 | A-19 | B-2 |
| 1-1120 | 5c-3 | A-20 | B-2 |
| 1-1121 | 5c-3 | A-21 | B-2 |
| 1-1122 | 5c-3 | A-22 | B-2 |
| 1-1123 | 5c-3 | A-23 | B-2 |
| 1-1124 | 5c-3 | A-24 | B-2 |
| 1-1125 | 5c-3 | A-25 | B-2 |
| 1-1126 | 5c-3 | A-26 | B-2 |
| 1-1127 | 5c-3 | A-27 | B-2 |
| 1-1128 | 5c-3 | A-28 | B-2 |
| 1-1129 | 5c-3 | A-29 | B-2 |
| 1-1130 | 5c-3 | A-30 | B-2 |
| 1-1131 | 5c-3 | A-31 | B-2 |
| 1-1132 | 5c-3 | A-32 | B-2 |
| 1-1133 | 5c-3 | A-33 | B-2 |
| 1-1134 | 5c-3 | A-34 | B-2 |
| 1-1135 | 5c-3 | A-35 | B-2 |
| 1-1136 | 5c-3 | A-36 | B-2 |
| 1-1137 | 5c-3 | A-37 | B-2 |
| 1-1138 | 5c-3 | A-38 | B-2 |
| 1-1139 | 5c-3 | A-39 | B-2 |

TABLE 9-continued

| Cmpd No. | Grp 4 | $X^1$ | $X^2$ |
|---|---|---|---|
| 1-1140 | 5c-3 | A-40 | B-2 |
| 1-1141 | 5c-3 | A-41 | B-2 |
| 1-1142 | 5c-3 | A-42 | B-2 |
| 1-1143 | 5c-3 | A-43 | B-2 |
| 1-1144 | 5c-3 | A-44 | B-2 |
| 1-1145 | 5c-3 | A-1 | B-3 |
| 1-1146 | 5c-3 | A-2 | B-3 |
| 1-1147 | 5c-3 | A-3 | B-3 |
| 1-1148 | 5c-3 | A-4 | B-3 |
| 1-1149 | 5c-3 | A-5 | B-3 |
| 1-1150 | 5c-3 | A-6 | B-3 |
| 1-1151 | 5c-3 | A-7 | B-3 |
| 1-1152 | 5c-3 | A-8 | B-3 |
| 1-1153 | 5c-3 | A-9 | B-3 |
| 1-1154 | 5c-3 | A-10 | B-3 |
| 1-1155 | 5c-3 | A-11 | B-3 |
| 1-1156 | 5c-3 | A-12 | B-3 |
| 1-1157 | 5c-3 | A-13 | B-3 |
| 1-1158 | 5c-3 | A-14 | B-3 |
| 1-1159 | 5c-3 | A-15 | B-3 |
| 1-1160 | 5c-3 | A-16 | B-3 |
| 1-1161 | 5c-3 | A-17 | B-3 |
| 1-1162 | 5c-3 | A-18 | B-3 |
| 1-1163 | 5c-3 | A-19 | B-3 |
| 1-1164 | 5c-3 | A-20 | B-3 |
| 1-1165 | 5c-3 | A-21 | B-3 |
| 1-1166 | 5c-3 | A-22 | B-3 |
| 1-1167 | 5c-3 | A-23 | B-3 |
| 1-1168 | 5c-3 | A-24 | B-3 |
| 1-1169 | 5c-3 | A-25 | B-3 |
| 1-1170 | 5c-3 | A-26 | B-3 |
| 1-1171 | 5c-3 | A-27 | B-3 |
| 1-1172 | 5c-3 | A-28 | B-3 |
| 1-1173 | 5c-3 | A-29 | B-3 |
| 1-1174 | 5c-3 | A-30 | B-3 |
| 1-1175 | 5c-3 | A-31 | B-3 |
| 1-1176 | 5c-3 | A-32 | B-3 |
| 1-1177 | 5c-3 | A-33 | B-3 |
| 1-1178 | 5c-3 | A-34 | B-3 |
| 1-1179 | 5c-3 | A-35 | B-3 |
| 1-1180 | 5c-3 | A-36 | B-3 |
| 1-1181 | 5c-3 | A-37 | B-3 |
| 1-1182 | 5c-3 | A-38 | B-3 |
| 1-1183 | 5c-3 | A-39 | B-3 |
| 1-1184 | 5c-3 | A-40 | B-3 |
| 1-1185 | 5c-3 | A-41 | B-3 |
| 1-1186 | 5c-3 | A-42 | B-3 |
| 1-1187 | 5c-3 | A-43 | B-3 |
| 1-1188 | 5c-3 | A-44 | B-3 |
| 1-1189 | 5c-3 | A-1 | B-4 |
| 1-1190 | 5c-3 | A-2 | B-4 |
| 1-1191 | 5c-3 | A-3 | B-4 |
| 1-1192 | 5c-3 | A-4 | B-4 |
| 1-1193 | 5c-3 | A-5 | B-4 |
| 1-1194 | 5c-3 | A-6 | B-4 |
| 1-1195 | 5c-3 | A-7 | B-4 |
| 1-1196 | 5c-3 | A-8 | B-4 |
| 1-1197 | 5c-3 | A-9 | B-4 |
| 1-1198 | 5c-3 | A-10 | B-4 |
| 1-1199 | 5c-3 | A-11 | B-4 |
| 1-1200 | 5c-3 | A-12 | B-4 |
| 1-1201 | 5c-3 | A-13 | B-4 |
| 1-1202 | 5c-3 | A-14 | B-4 |
| 1-1203 | 5c-3 | A-15 | B-4 |
| 1-1204 | 5c-3 | A-16 | B-4 |
| 1-1205 | 5c-3 | A-17 | B-4 |
| 1-1206 | 5c-3 | A-18 | B-4 |
| 1-1207 | 5c-3 | A-19 | B-4 |
| 1-1208 | 5c-3 | A-20 | B-4 |
| 1-1209 | 5c-3 | A-21 | B-4 |
| 1-1210 | 5c-3 | A-22 | B-4 |
| 1-1211 | 5c-3 | A-23 | B-4 |
| 1-1212 | 5c-3 | A-24 | B-4 |
| 1-1213 | 5c-3 | A-25 | B-4 |
| 1-1214 | 5c-3 | A-26 | B-4 |
| 1-1215 | 5c-3 | A-27 | B-4 |
| 1-1216 | 5c-3 | A-28 | B-4 |
| 1-1217 | 5c-3 | A-29 | B-4 |
| 1-1218 | 5c-3 | A-30 | B-4 |
| 1-1219 | 5c-3 | A-31 | B-4 |
| 1-1220 | 5c-3 | A-32 | B-4 |
| 1-1221 | 5c-3 | A-33 | B-4 |
| 1-1222 | 5c-3 | A-34 | B-4 |
| 1-1223 | 5c-3 | A-35 | B-4 |
| 1-1224 | 5c-3 | A-36 | B-4 |
| 1-1225 | 5c-3 | A-37 | B-4 |
| 1-1226 | 5c-3 | A-38 | B-4 |
| 1-1227 | 5c-3 | A-39 | B-4 |
| 1-1228 | 5c-3 | A-40 | B-4 |
| 1-1229 | 5c-3 | A-41 | B-4 |
| 1-1230 | 5c-3 | A-42 | B-4 |
| 1-1231 | 5c-3 | A-43 | B-4 |
| 1-1232 | 5c-3 | A-44 | B-4 |
| 1-1233 | 5c-4 | A-1 | B-1 |
| 1-1234 | 5c-4 | A-2 | B-1 |
| 1-1235 | 5c-4 | A-3 | B-1 |
| 1-1236 | 5c-4 | A-4 | B-1 |
| 1-1237 | 5c-4 | A-5 | B-1 |
| 1-1238 | 5c-4 | A-6 | B-1 |
| 1-1239 | 5c-4 | A-7 | B-1 |
| 1-1240 | 5c-4 | A-8 | B-1 |
| 1-1241 | 5c-4 | A-9 | B-1 |
| 1-1242 | 5c-4 | A-10 | B-1 |

TABLE 10

| Cmpd No. | Grp 4 | $X^1$ | $X^2$ |
|---|---|---|---|
| 1-1243 | 5c-4 | A-11 | B-1 |
| 1-1244 | 5c-4 | A-12 | B-1 |
| 1-1245 | 5c-4 | A-13 | B-1 |
| 1-1246 | 5c-4 | A-14 | B-1 |
| 1-1247 | 5c-4 | A-15 | B-1 |
| 1-1248 | 5c-4 | A-16 | B-1 |
| 1-1249 | 5c-4 | A-17 | B-1 |
| 1-1250 | 5c-4 | A-18 | B-1 |
| 1-1251 | 5c-4 | A-19 | B-1 |
| 1-1252 | 5c-4 | A-20 | B-1 |
| 1-1253 | 5c-4 | A-21 | B-1 |
| 1-1254 | 5c-4 | A-22 | B-1 |
| 1-1255 | 5c-4 | A-23 | B-1 |
| 1-1256 | 5c-4 | A-24 | B-1 |
| 1-1257 | 5c-4 | A-25 | B-1 |
| 1-1258 | 5c-4 | A-26 | B-1 |
| 1-1259 | 5c-4 | A-27 | B-1 |
| 1-1260 | 5c-4 | A-28 | B-1 |
| 1-1261 | 5c-4 | A-29 | B-1 |
| 1-1262 | 5c-4 | A-30 | B-1 |
| 1-1263 | 5c-4 | A-31 | B-1 |
| 1-1264 | 5c-4 | A-32 | B-1 |
| 1-1265 | 5c-4 | A-33 | B-1 |
| 1-1266 | 5c-4 | A-34 | B-1 |
| 1-1267 | 5c-4 | A-35 | B-1 |
| 1-1268 | 5c-4 | A-36 | B-1 |
| 1-1269 | 5c-4 | A-37 | B-1 |
| 1-1270 | 5c-4 | A-38 | B-1 |
| 1-1271 | 5c-4 | A-39 | B-1 |
| 1-1272 | 5c-4 | A-40 | B-1 |
| 1-1273 | 5c-4 | A-41 | B-1 |
| 1-1274 | 5c-4 | A-42 | B-1 |
| 1-1275 | 5c-4 | A-43 | B-1 |
| 1-1276 | 5c-4 | A-44 | B-1 |
| 1-1277 | 5c-4 | A-1 | B-2 |
| 1-1278 | 5c-4 | A-2 | B-2 |
| 1-1279 | 5c-4 | A-3 | B-2 |
| 1-1280 | 5c-4 | A-4 | B-2 |
| 1-1281 | 5c-4 | A-5 | B-2 |
| 1-1282 | 5c-4 | A-6 | B-2 |
| 1-1283 | 5c-4 | A-7 | B-2 |
| 1-1284 | 5c-4 | A-8 | B-2 |

TABLE 10-continued

| Cmpd No. | Grp 4 | X¹ | X² |
|---|---|---|---|
| 1-1285 | 5c-4 | A-9 | B-2 |
| 1-1286 | 5c-4 | A-10 | B-2 |
| 1-1287 | 5c-4 | A-11 | B-2 |
| 1-1288 | 5c-4 | A-12 | B-2 |
| 1-1289 | 5c-4 | A-13 | B-2 |
| 1-1290 | 5c-4 | A-14 | B-2 |
| 1-1291 | 5c-4 | A-15 | B-2 |
| 1-1292 | 5c-4 | A-16 | B-2 |
| 1-1293 | 5c-4 | A-17 | B-2 |
| 1-1294 | 5c-4 | A-18 | B-2 |
| 1-1295 | 5c-4 | A-19 | B-2 |
| 1-1296 | 5c-4 | A-20 | B-2 |
| 1-1297 | 5c-4 | A-21 | B-2 |
| 1-1298 | 5c-4 | A-22 | B-2 |
| 1-1299 | 5c-4 | A-23 | B-2 |
| 1-1300 | 5c-4 | A-24 | B-2 |
| 1-1301 | 5c-4 | A-25 | B-2 |
| 1-1302 | 5c-4 | A-26 | B-2 |
| 1-1303 | 5c-4 | A-27 | B-2 |
| 1-1304 | 5c-4 | A-28 | B-2 |
| 1-1305 | 5c-4 | A-29 | B-2 |
| 1-1306 | 5c-4 | A-30 | B-2 |
| 1-1307 | 5c-4 | A-31 | B-2 |
| 1-1308 | 5c-4 | A-32 | B-2 |
| 1-1309 | 5c-4 | A-33 | B-2 |
| 1-1310 | 5c-4 | A-34 | B-2 |
| 1-1311 | 5c-4 | A-35 | B-2 |
| 1-1312 | 5c-4 | A-36 | B-2 |
| 1-1313 | 5c-4 | A-37 | B-2 |
| 1-1314 | 5c-4 | A-38 | B-2 |
| 1-1315 | 5c-4 | A-39 | B-2 |
| 1-1316 | 5c-4 | A-40 | B-2 |
| 1-1317 | 5c-4 | A-41 | B-2 |
| 1-1318 | 5c-4 | A-42 | B-2 |
| 1-1319 | 5c-4 | A-43 | B-2 |
| 1-1320 | 5c-4 | A-44 | B-2 |
| 1-1321 | 5c-4 | A-1 | B-3 |
| 1-1322 | 5c-4 | A-2 | B-3 |
| 1-1323 | 5c-4 | A-3 | B-3 |
| 1-1324 | 5c-4 | A-4 | B-3 |
| 1-1325 | 5c-4 | A-5 | B-3 |
| 1-1326 | 5c-4 | A-6 | B-3 |
| 1-1327 | 5c-4 | A-7 | B-3 |
| 1-1328 | 5c-4 | A-8 | B-3 |
| 1-1329 | 5c-4 | A-9 | B-3 |
| 1-1330 | 5c-4 | A-10 | B-3 |
| 1-1331 | 5c-4 | A-11 | B-3 |
| 1-1332 | 5c-4 | A-12 | B-3 |
| 1-1333 | 5c-4 | A-13 | B-3 |
| 1-1334 | 5c-4 | A-14 | B-3 |
| 1-1335 | 5c-4 | A-15 | B-3 |
| 1-1336 | 5c-4 | A-16 | B-3 |
| 1-1337 | 5c-4 | A-17 | B-3 |
| 1-1338 | 5c-4 | A-18 | B-3 |
| 1-1339 | 5c-4 | A-19 | B-3 |
| 1-1340 | 5c-4 | A-20 | B-3 |
| 1-1341 | 5c-4 | A-21 | B-3 |
| 1-1342 | 5c-4 | A-22 | B-3 |
| 1-1343 | 5c-4 | A-23 | B-3 |
| 1-1344 | 5c-4 | A-24 | B-3 |
| 1-1345 | 5c-4 | A-25 | B-3 |
| 1-1346 | 5c-4 | A-26 | B-3 |
| 1-1347 | 5c-4 | A-27 | B-3 |
| 1-1348 | 5c-4 | A-28 | B-3 |
| 1-1349 | 5c-4 | A-29 | B-3 |
| 1-1350 | 5c-4 | A-30 | B-3 |
| 1-1351 | 5c-4 | A-31 | B-3 |
| 1-1352 | 5c-4 | A-32 | B-3 |
| 1-1353 | 5c-4 | A-33 | B-3 |
| 1-1354 | 5c-4 | A-34 | B-3 |
| 1-1355 | 5c-4 | A-35 | B-3 |
| 1-1356 | 5c-4 | A-36 | B-3 |
| 1-1357 | 5c-4 | A-37 | B-3 |
| 1-1358 | 5c-4 | A-38 | B-3 |
| 1-1359 | 5c-4 | A-39 | B-3 |
| 1-1360 | 5c-4 | A-40 | B-3 |
| 1-1361 | 5c-4 | A-41 | B-3 |
| 1-1362 | 5c-4 | A-42 | B-3 |
| 1-1363 | 5c-4 | A-43 | B-3 |
| 1-1364 | 5c-4 | A-44 | B-3 |
| 1-1365 | 5c-4 | A-1 | B-4 |
| 1-1366 | 5c-4 | A-2 | B-4 |
| 1-1367 | 5c-4 | A-3 | B-4 |
| 1-1368 | 5c-4 | A-4 | B-4 |
| 1-1369 | 5c-4 | A-5 | B-4 |
| 1-1370 | 5c-4 | A-6 | B-4 |
| 1-1371 | 5c-4 | A-7 | B-4 |
| 1-1372 | 5c-4 | A-8 | B-4 |
| 1-1373 | 5c-4 | A-9 | B-4 |
| 1-1374 | 5c-4 | A-10 | B-4 |
| 1-1375 | 5c-4 | A-11 | B-4 |
| 1-1376 | 5c-4 | A-12 | B-4 |
| 1-1377 | 5c-4 | A-13 | B-4 |
| 1-1378 | 5c-4 | A-14 | B-4 |
| 1-1379 | 5c-4 | A-15 | B-4 |
| 1-1380 | 5c-4 | A-16 | B-4 |

TABLE 11

| Cmpd No. | Grp 4 | X¹ | X² |
|---|---|---|---|
| 1-1381 | 5c-4 | A-17 | B-4 |
| 1-1382 | 5c-4 | A-18 | B-4 |
| 1-1383 | 5c-4 | A-19 | B-4 |
| 1-1384 | 5c-4 | A-20 | B-4 |
| 1-1385 | 5c-4 | A-21 | B-4 |
| 1-1386 | 5c-4 | A-22 | B-4 |
| 1-1387 | 5c-4 | A-23 | B-4 |
| 1-1388 | 5c-4 | A-24 | B-4 |
| 1-1389 | 5c-4 | A-25 | B-4 |
| 1-1390 | 5c-4 | A-26 | B-4 |
| 1-1391 | 5c-4 | A-27 | B-4 |
| 1-1392 | 5c-4 | A-28 | B-4 |
| 1-1393 | 5c-4 | A-29 | B-4 |
| 1-1394 | 5c-4 | A-30 | B-4 |
| 1-1395 | 5c-4 | A-31 | B-4 |
| 1-1396 | 5c-4 | A-32 | B-4 |
| 1-1397 | 5c-4 | A-33 | B-4 |
| 1-1398 | 5c-4 | A-34 | B-4 |
| 1-1399 | 5c-4 | A-35 | B-4 |
| 1-1400 | 5c-4 | A-36 | B-4 |
| 1-1401 | 5c-4 | A-37 | B-4 |
| 1-1402 | 5c-4 | A-38 | B-4 |
| 1-1403 | 5c-4 | A-39 | B-4 |
| 1-1404 | 5c-4 | A-40 | B-4 |
| 1-1405 | 5c-4 | A-41 | B-4 |
| 1-1406 | 5c-4 | A-42 | B-4 |
| 1-1407 | 5c-4 | A-43 | B-4 |
| 1-1408 | 5c-4 | A-44 | B-4 |

According to an example embodiment, the second host compound is a compound having hole characteristics, and may show bipolar characteristics along with the first host compound.

According to an example embodiment, the second host compound may include at least one carbazole group with a substituent having hole characteristics.

According to an example embodiment, the second host compound may be represented by, for example, Chemical Formula 4,

[Chemical Formula 4]

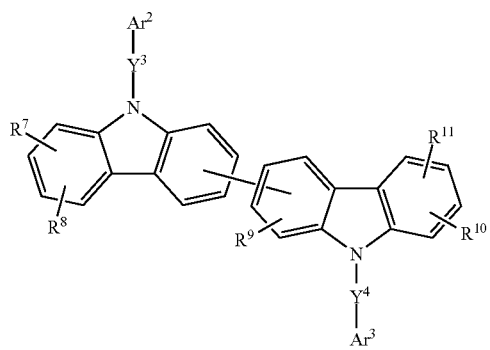

According to the present example embodiment, in the Chemical Formula 4,

Ar² and Ar³ are each independently a substituted or unsubstituted C6 to C30 aryl group, a substituted or unsubstituted C2 to C30 heteroaryl group, or a combination thereof, Y³ and Y⁴ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, and R⁷ to R¹¹ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

In the Chemical Formula 4, Ar² and Ar³ are each independently a substituent having hole characteristics, for example, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, or a combination thereof.

According to an example embodiment, a biscarbazole core of the Chemical Formula 4 may be one of the groups listed in the Group 5.

According to an example embodiment, the *—Y³—Ar², *—Y⁴—Ar³ may be one of substituents listed in Group 3.

[Group 5]

C-1

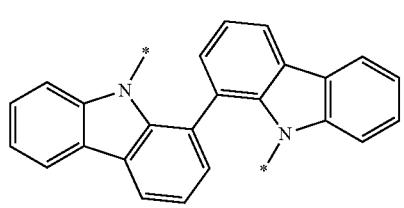

C-2

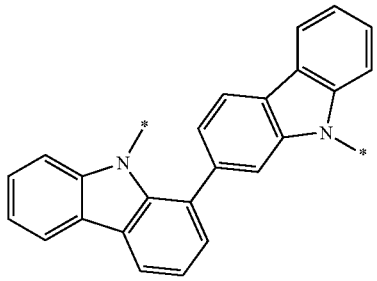

C-3

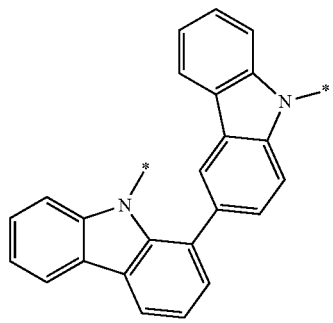

C-4

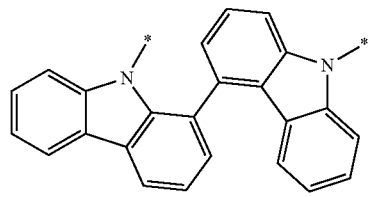

C-5

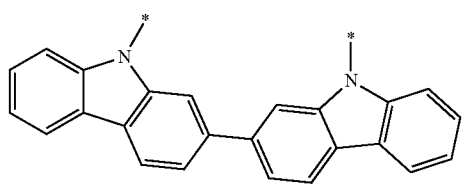

C-6

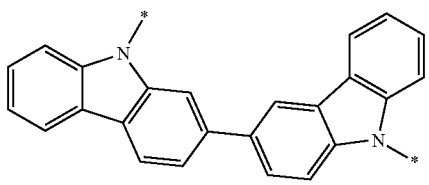

C-7

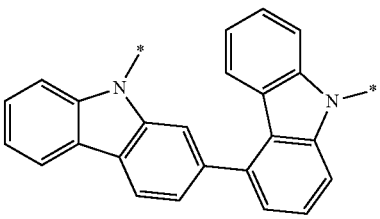

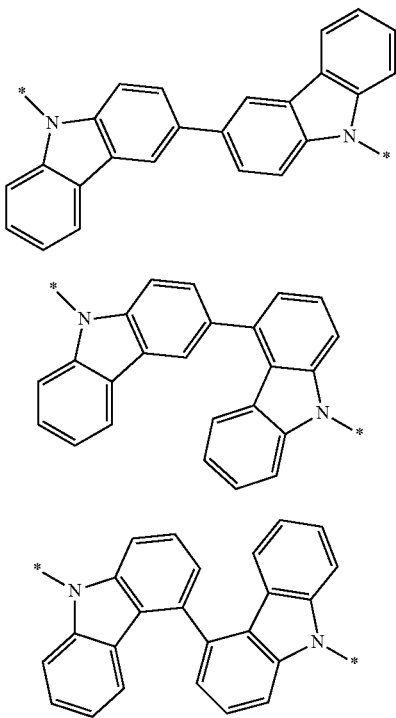

According to an example embodiment, the second host compound represented by the Chemical Formula 4 may be one of compound listed in the following Tables 12 to 21,

TABLE 12

| Cmpd No. | Grp 5 | *—$Y^3$—$Ar^2$ | *—$Y^4$—$Ar^3$ |
|---|---|---|---|
| 2-1 | C-1 | B-1 | B-1 |
| 2-2 | C-1 | B-1 | B-2 |
| 2-3 | C-1 | B-1 | B-3 |
| 2-4 | C-1 | B-1 | B-4 |
| 2-5 | C-1 | B-1 | B-5 |
| 2-6 | C-1 | B-1 | B-6 |
| 2-7 | C-1 | B-1 | B-7 |
| 2-8 | C-1 | B-1 | B-8 |
| 2-9 | C-1 | B-1 | B-9 |
| 2-10 | C-1 | B-1 | B-10 |
| 2-11 | C-1 | B-1 | B-11 |
| 2-12 | C-1 | B-1 | B-12 |
| 2-13 | C-1 | B-2 | B-2 |
| 2-14 | C-1 | B-2 | B-3 |
| 2-15 | C-1 | B-2 | B-4 |
| 2-16 | C-1 | B-2 | B-5 |
| 2-17 | C-1 | B-2 | B-6 |
| 2-18 | C-1 | B-2 | B-7 |
| 2-19 | C-1 | B-2 | B-8 |
| 2-20 | C-1 | B-2 | B-9 |
| 2-21 | C-1 | B-2 | B-10 |
| 2-22 | C-1 | B-2 | B-11 |
| 2-23 | C-1 | B-2 | B-12 |
| 2-24 | C-1 | B-3 | B-3 |
| 2-25 | C-1 | B-3 | B-4 |
| 2-26 | C-1 | B-3 | B-5 |
| 2-27 | C-1 | B-3 | B-6 |
| 2-28 | C-1 | B-3 | B-7 |
| 2-29 | C-1 | B-3 | B-8 |
| 2-30 | C-1 | B-3 | B-9 |
| 2-31 | C-1 | B-3 | B-10 |
| 2-32 | C-1 | B-3 | B-11 |
| 2-33 | C-1 | B-3 | B-12 |
| 2-34 | C-1 | B-4 | B-4 |
| 2-35 | C-1 | B-4 | B-5 |
| 2-36 | C-1 | B-4 | B-6 |
| 2-37 | C-1 | B-4 | B-7 |
| 2-38 | C-1 | B-4 | B-8 |
| 2-39 | C-1 | B-4 | B-9 |
| 2-40 | C-1 | B-4 | B-10 |
| 2-41 | C-1 | B-4 | B-11 |
| 2-42 | C-1 | B-4 | B-12 |
| 2-43 | C-1 | B-5 | B-5 |
| 2-44 | C-1 | B-5 | B-6 |
| 2-45 | C-1 | B-5 | B-7 |
| 2-46 | C-1 | B-5 | B-8 |
| 2-47 | C-1 | B-5 | B-9 |
| 2-48 | C-1 | B-5 | B-10 |
| 2-49 | C-1 | B-5 | B-11 |
| 2-50 | C-1 | B-5 | B-12 |
| 2-51 | C-1 | B-6 | B-6 |
| 2-52 | C-1 | B-6 | B-7 |
| 2-53 | C-1 | B-6 | B-8 |
| 2-54 | C-1 | B-6 | B-9 |
| 2-55 | C-1 | B-6 | B-10 |
| 2-56 | C-1 | B-6 | B-11 |
| 2-57 | C-1 | B-6 | B-12 |
| 2-58 | C-1 | B-7 | B-7 |
| 2-59 | C-1 | B-7 | B-8 |
| 2-60 | C-1 | B-7 | B-9 |
| 2-61 | C-1 | B-7 | B-10 |
| 2-62 | C-1 | B-7 | B-11 |
| 2-63 | C-1 | B-7 | B-12 |
| 2-64 | C-1 | B-8 | B-8 |
| 2-65 | C-1 | B-8 | B-9 |
| 2-66 | C-1 | B-8 | B-10 |
| 2-67 | C-1 | B-8 | B-11 |
| 2-68 | C-1 | B-8 | B-12 |
| 2-69 | C-1 | B-9 | B-9 |
| 2-70 | C-1 | B-9 | B-10 |
| 2-71 | C-1 | B-9 | B-11 |
| 2-72 | C-1 | B-9 | B-12 |
| 2-73 | C-1 | B-10 | B-10 |
| 2-74 | C-1 | B-10 | B-11 |
| 2-75 | C-1 | B-10 | B-12 |
| 2-76 | C-1 | B-11 | B-11 |
| 2-77 | C-1 | B-11 | B-12 |
| 2-78 | C-1 | B-12 | B-12 |
| 2-79 | C-2 | B-1 | B-1 |
| 2-80 | C-2 | B-1 | B-2 |
| 2-81 | C-2 | B-1 | B-3 |
| 2-82 | C-2 | B-1 | B-4 |
| 2-83 | C-2 | B-1 | B-5 |
| 2-84 | C-2 | B-1 | B-6 |
| 2-85 | C-2 | B-1 | B-7 |
| 2-86 | C-2 | B-1 | B-8 |
| 2-87 | C-2 | B-1 | B-9 |
| 2-88 | C-2 | B-1 | B-10 |
| 2-89 | C-2 | B-1 | B-11 |
| 2-90 | C-2 | B-1 | B-12 |
| 2-91 | C-2 | B-2 | B-1 |
| 2-92 | C-2 | B-2 | B-2 |
| 2-93 | C-2 | B-2 | B-3 |
| 2-94 | C-2 | B-2 | B-4 |
| 2-95 | C-2 | B-2 | B-5 |
| 2-96 | C-2 | B-2 | B-6 |
| 2-97 | C-2 | B-2 | B-7 |
| 2-98 | C-2 | B-2 | B-8 |
| 2-99 | C-2 | B-2 | B-9 |
| 2-100 | C-2 | B-2 | B-10 |
| 2-101 | C-2 | B-2 | B-11 |
| 2-102 | C-2 | B-2 | B-12 |
| 2-103 | C-2 | B-3 | B-1 |
| 2-104 | C-2 | B-3 | B-2 |
| 2-105 | C-2 | B-3 | B-3 |
| 2-106 | C-2 | B-3 | B-4 |
| 2-107 | C-2 | B-3 | B-5 |
| 2-108 | C-2 | B-3 | B-6 |
| 2-109 | C-2 | B-3 | B-7 |
| 2-110 | C-2 | B-3 | B-8 |
| 2-111 | C-2 | B-3 | B-9 |
| 2-112 | C-2 | B-3 | B-10 |

TABLE 12-continued

| Cmpd No. | Grp 5 | *—Y³—Ar² | *—Y⁴—Ar³ |
|---|---|---|---|
| 2-113 | C-2 | B-3 | B-11 |
| 2-114 | C-2 | B-3 | B-12 |
| 2-115 | C-2 | B-4 | B-1 |
| 2-116 | C-2 | B-4 | B-2 |
| 2-117 | C-2 | B-4 | B-3 |
| 2-118 | C-2 | B-4 | B-4 |
| 2-119 | C-2 | B-4 | B-5 |
| 2-120 | C-2 | B-4 | B-6 |
| 2-121 | C-2 | B-4 | B-7 |
| 2-122 | C-2 | B-4 | B-8 |
| 2-123 | C-2 | B-4 | B-9 |
| 2-124 | C-2 | B-4 | B-10 |
| 2-125 | C-2 | B-4 | B-11 |
| 2-126 | C-2 | B-4 | B-12 |
| 2-127 | C-2 | B-5 | B-1 |
| 2-128 | C-2 | B-5 | B-2 |
| 2-129 | C-2 | B-5 | B-3 |
| 2-130 | C-2 | B-5 | B-4 |
| 2-131 | C-2 | B-5 | B-5 |
| 2-132 | C-2 | B-5 | B-6 |

TABLE 13

| Cmpd No. | Grp 5 | *—Y³—Ar² | *—Y⁴—Ar³ |
|---|---|---|---|
| 2-133 | C-2 | B-5 | B-7 |
| 2-134 | C-2 | B-5 | B-8 |
| 2-135 | C-2 | B-5 | B-9 |
| 2-136 | C-2 | B-5 | B-10 |
| 2-137 | C-2 | B-5 | B-11 |
| 2-138 | C-2 | B-5 | B-12 |
| 2-139 | C-2 | B-6 | B-1 |
| 2-140 | C-2 | B-6 | B-2 |
| 2-141 | C-2 | B-6 | B-3 |
| 2-142 | C-2 | B-6 | B-4 |
| 2-143 | C-2 | B-6 | B-5 |
| 2-144 | C-2 | B-6 | B-6 |
| 2-145 | C-2 | B-6 | B-7 |
| 2-146 | C-2 | B-6 | B-8 |
| 2-147 | C-2 | B-6 | B-9 |
| 2-148 | C-2 | B-6 | B-10 |
| 2-149 | C-2 | B-6 | B-11 |
| 2-150 | C-2 | B-6 | B-12 |
| 2-151 | C-2 | B-7 | B-1 |
| 2-152 | C-2 | B-7 | B-2 |
| 2-153 | C-2 | B-7 | B-3 |
| 2-154 | C-2 | B-7 | B-4 |
| 2-155 | C-2 | B-7 | B-5 |
| 2-156 | C-2 | B-7 | B-6 |
| 2-157 | C-2 | B-7 | B-7 |
| 2-158 | C-2 | B-7 | B-8 |
| 2-159 | C-2 | B-7 | B-9 |
| 2-160 | C-2 | B-7 | B-10 |
| 2-161 | C-2 | B-7 | B-11 |
| 2-162 | C-2 | B-7 | B-12 |
| 2-163 | C-2 | B-8 | B-1 |
| 2-164 | C-2 | B-8 | B-2 |
| 2-165 | C-2 | B-8 | B-3 |
| 2-166 | C-2 | B-8 | B-4 |
| 2-167 | C-2 | B-8 | B-5 |
| 2-168 | C-2 | B-8 | B-6 |
| 2-169 | C-2 | B-8 | B-7 |
| 2-170 | C-2 | B-8 | B-8 |
| 2-171 | C-2 | B-8 | B-9 |
| 2-172 | C-2 | B-8 | B-10 |
| 2-173 | C-2 | B-8 | B-11 |
| 2-174 | C-2 | B-8 | B-12 |
| 2-175 | C-2 | B-9 | B-1 |
| 2-176 | C-2 | B-9 | B-2 |
| 2-177 | C-2 | B-9 | B-3 |
| 2-178 | C-2 | B-9 | B-4 |
| 2-179 | C-2 | B-9 | B-5 |
| 2-180 | C-2 | B-9 | B-6 |

TABLE 13-continued

| Cmpd No. | Grp 5 | *—Y³—Ar² | *—Y⁴—Ar³ |
|---|---|---|---|
| 2-181 | C-2 | B-9 | B-7 |
| 2-182 | C-2 | B-9 | B-8 |
| 2-183 | C-2 | B-9 | B-9 |
| 2-184 | C-2 | B-9 | B-10 |
| 2-185 | C-2 | B-9 | B-11 |
| 2-186 | C-2 | B-9 | B-12 |
| 2-187 | C-2 | B-10 | B-1 |
| 2-188 | C-2 | B-10 | B-2 |
| 2-189 | C-2 | B-10 | B-3 |
| 2-190 | C-2 | B-10 | B-4 |
| 2-191 | C-2 | B-10 | B-5 |
| 2-192 | C-2 | B-10 | B-6 |
| 2-193 | C-2 | B-10 | B-7 |
| 2-194 | C-2 | B-10 | B-8 |
| 2-195 | C-2 | B-10 | B-9 |
| 2-196 | C-2 | B-10 | B-10 |
| 2-197 | C-2 | B-10 | B-11 |
| 2-198 | C-2 | B-10 | B-12 |
| 2-199 | C-2 | B-11 | B-1 |
| 2-200 | C-2 | B-11 | B-2 |
| 2-201 | C-2 | B-11 | B-3 |
| 2-202 | C-2 | B-11 | B-4 |
| 2-203 | C-2 | B-11 | B-5 |
| 2-204 | C-2 | B-11 | B-6 |
| 2-205 | C-2 | B-11 | B-7 |
| 2-206 | C-2 | B-11 | B-8 |
| 2-207 | C-2 | B-11 | B-9 |
| 2-208 | C-2 | B-11 | B-10 |
| 2-209 | C-2 | B-11 | B-11 |
| 2-210 | C-2 | B-11 | B-12 |
| 2-211 | C-2 | B-12 | B-1 |
| 2-212 | C-2 | B-12 | B-2 |
| 2-213 | C-2 | B-12 | B-3 |
| 2-214 | C-2 | B-12 | B-4 |
| 2-215 | C-2 | B-12 | B-5 |
| 2-216 | C-2 | B-12 | B-6 |
| 2-217 | C-2 | B-12 | B-7 |
| 2-218 | C-2 | B-12 | B-8 |
| 2-219 | C-2 | B-12 | B-9 |
| 2-220 | C-2 | B-12 | B-10 |
| 2-221 | C-2 | B-12 | B-11 |
| 2-222 | C-2 | B-12 | B-12 |
| 2-223 | C-3 | B-1 | B-1 |
| 2-224 | C-3 | B-1 | B-2 |
| 2-225 | C-3 | B-1 | B-3 |
| 2-226 | C-3 | B-1 | B-4 |
| 2-227 | C-3 | B-1 | B-5 |
| 2-228 | C-3 | B-1 | B-6 |
| 2-229 | C-3 | B-1 | B-7 |
| 2-230 | C-3 | B-1 | B-8 |
| 2-231 | C-3 | B-1 | B-9 |
| 2-232 | C-3 | B-1 | B-10 |
| 2-233 | C-3 | B-1 | B-11 |
| 2-234 | C-3 | B-1 | B-12 |
| 2-235 | C-3 | B-2 | B-1 |
| 2-236 | C-3 | B-2 | B-2 |
| 2-237 | C-3 | B-2 | B-3 |
| 2-238 | C-3 | B-2 | B-4 |
| 2-239 | C-3 | B-2 | B-5 |
| 2-240 | C-3 | B-2 | B-6 |
| 2-241 | C-3 | B-2 | B-7 |
| 2-242 | C-3 | B-2 | B-8 |
| 2-243 | C-3 | B-2 | B-9 |
| 2-244 | C-3 | B-2 | B-10 |
| 2-245 | C-3 | B-2 | B-11 |
| 2-246 | C-3 | B-2 | B-12 |
| 2-247 | C-3 | B-3 | B-1 |
| 2-248 | C-3 | B-3 | B-2 |
| 2-249 | C-3 | B-3 | B-3 |
| 2-250 | C-3 | B-3 | B-4 |
| 2-251 | C-3 | B-3 | B-5 |
| 2-252 | C-3 | B-3 | B-6 |
| 2-253 | C-3 | B-3 | B-7 |
| 2-254 | C-3 | B-3 | B-8 |
| 2-255 | C-3 | B-3 | B-9 |
| 2-256 | C-3 | B-3 | B-10 |
| 2-257 | C-3 | B-3 | B-11 |

TABLE 13-continued

| Cmpd No. | Grp 5 | *—$Y^3$—$Ar^2$ | *—$Y^4$—$Ar^3$ |
|---|---|---|---|
| 2-258 | C-3 | B-3 | B-12 |
| 2-259 | C-3 | B-4 | B-1 |
| 2-260 | C-3 | B-4 | B-2 |
| 2-261 | C-3 | B-4 | B-3 |
| 2-262 | C-3 | B-4 | B-4 |
| 2-263 | C-3 | B-4 | B-5 |
| 2-264 | C-3 | B-4 | B-6 |

TABLE 14

| Cmpd No. | Grp 5 | *—$Y^3$—$Ar^2$ | *—$Y^4$—$Ar^3$ |
|---|---|---|---|
| 2-265 | C-3 | B-4 | B-7 |
| 2-266 | C-3 | B-4 | B-8 |
| 2-267 | C-3 | B-4 | B-9 |
| 2-268 | C-3 | B-4 | B-10 |
| 2-269 | C-3 | B-4 | B-11 |
| 2-270 | C-3 | B-4 | B-12 |
| 2-271 | C-3 | B-5 | B-1 |
| 2-272 | C-3 | B-5 | B-2 |
| 2-273 | C-3 | B-5 | B-3 |
| 2-274 | C-3 | B-5 | B-4 |
| 2-275 | C-3 | B-5 | B-5 |
| 2-276 | C-3 | B-5 | B-6 |
| 2-277 | C-3 | B-5 | B-7 |
| 2-278 | C-3 | B-5 | B-8 |
| 2-279 | C-3 | B-5 | B-9 |
| 2-280 | C-3 | B-5 | B-10 |
| 2-281 | C-3 | B-5 | B-11 |
| 2-282 | C-3 | B-5 | B-12 |
| 2-283 | C-3 | B-6 | B-1 |
| 2-284 | C-3 | B-6 | B-2 |
| 2-285 | C-3 | B-6 | B-3 |
| 2-286 | C-3 | B-6 | B-4 |
| 2-287 | C-3 | B-6 | B-5 |
| 2-288 | C-3 | B-6 | B-6 |
| 2-289 | C-3 | B-6 | B-7 |
| 2-290 | C-3 | B-6 | B-8 |
| 2-291 | C-3 | B-6 | B-9 |
| 2-292 | C-3 | B-6 | B-10 |
| 2-293 | C-3 | B-6 | B-11 |
| 2-294 | C-3 | B-6 | B-12 |
| 2-295 | C-3 | B-7 | B-1 |
| 2-296 | C-3 | B-7 | B-2 |
| 2-297 | C-3 | B-7 | B-3 |
| 2-298 | C-3 | B-7 | B-4 |
| 2-299 | C-3 | B-7 | B-5 |
| 2-300 | C-3 | B-7 | B-6 |
| 2-301 | C-3 | B-7 | B-7 |
| 2-302 | C-3 | B-7 | B-8 |
| 2-303 | C-3 | B-7 | B-9 |
| 2-304 | C-3 | B-7 | B-10 |
| 2-305 | C-3 | B-7 | B-11 |
| 2-306 | C-3 | B-7 | B-12 |
| 2-307 | C-3 | B-8 | B-1 |
| 2-308 | C-3 | B-8 | B-2 |
| 2-309 | C-3 | B-8 | B-3 |
| 2-310 | C-3 | B-8 | B-4 |
| 2-311 | C-3 | B-8 | B-5 |
| 2-312 | C-3 | B-8 | B-6 |
| 2-313 | C-3 | B-8 | B-7 |
| 2-314 | C-3 | B-8 | B-8 |
| 2-315 | C-3 | B-8 | B-9 |
| 2-316 | C-3 | B-8 | B-10 |
| 2-317 | C-3 | B-8 | B-11 |
| 2-318 | C-3 | B-8 | B-12 |
| 2-319 | C-3 | B-9 | B-1 |
| 2-320 | C-3 | B-9 | B-2 |
| 2-321 | C-3 | B-9 | B-3 |
| 2-322 | C-3 | B-9 | B-4 |
| 2-323 | C-3 | B-9 | B-5 |
| 2-324 | C-3 | B-9 | B-6 |
| 2-325 | C-3 | B-9 | B-7 |

TABLE 14-continued

| Cmpd No. | Grp 5 | *—$Y^3$—$Ar^2$ | *—$Y^4$—$Ar^3$ |
|---|---|---|---|
| 2-326 | C-3 | B-9 | B-8 |
| 2-327 | C-3 | B-9 | B-9 |
| 2-328 | C-3 | B-9 | B-10 |
| 2-329 | C-3 | B-9 | B-11 |
| 2-330 | C-3 | B-9 | B-12 |
| 2-331 | C-3 | B-10 | B-1 |
| 2-332 | C-3 | B-10 | B-2 |
| 2-333 | C-3 | B-10 | B-3 |
| 2-334 | C-3 | B-10 | B-4 |
| 2-335 | C-3 | B-10 | B-5 |
| 2-336 | C-3 | B-10 | B-6 |
| 2-337 | C-3 | B-10 | B-7 |
| 2-338 | C-3 | B-10 | B-8 |
| 2-339 | C-3 | B-10 | B-9 |
| 2-340 | C-3 | B-10 | B-10 |
| 2-341 | C-3 | B-10 | B-11 |
| 2-342 | C-3 | B-10 | B-12 |
| 2-343 | C-3 | B-11 | B-1 |
| 2-344 | C-3 | B-11 | B-2 |
| 2-345 | C-3 | B-11 | B-3 |
| 2-346 | C-3 | B-11 | B-4 |
| 2-347 | C-3 | B-11 | B-5 |
| 2-348 | C-3 | B-11 | B-6 |
| 2-349 | C-3 | B-11 | B-7 |
| 2-350 | C-3 | B-11 | B-8 |
| 2-351 | C-3 | B-11 | B-9 |
| 2-352 | C-3 | B-11 | B-10 |
| 2-353 | C-3 | B-11 | B-11 |
| 2-354 | C-3 | B-11 | B-12 |
| 2-355 | C-3 | B-12 | B-1 |
| 2-356 | C-3 | B-12 | B-2 |
| 2-357 | C-3 | B-12 | B-3 |
| 2-358 | C-3 | B-12 | B-4 |
| 2-359 | C-3 | B-12 | B-5 |
| 2-360 | C-3 | B-12 | B-6 |
| 2-361 | C-3 | B-12 | B-7 |
| 2-362 | C-3 | B-12 | B-8 |
| 2-363 | C-3 | B-12 | B-9 |
| 2-364 | C-3 | B-12 | B-10 |
| 2-365 | C-3 | B-12 | B-11 |
| 2-366 | C-3 | B-12 | B-12 |
| 2-367 | C-4 | B-1 | B-1 |
| 2-368 | C-4 | B-1 | B-2 |
| 2-369 | C-4 | B-1 | B-3 |
| 2-370 | C-4 | B-1 | B-4 |
| 2-371 | C-4 | B-1 | B-5 |
| 2-372 | C-4 | B-1 | B-6 |
| 2-373 | C-4 | B-1 | B-7 |
| 2-374 | C-4 | B-1 | B-8 |
| 2-375 | C-4 | B-1 | B-9 |
| 2-376 | C-4 | B-1 | B-10 |
| 2-377 | C-4 | B-1 | B-11 |
| 2-378 | C-4 | B-1 | B-12 |
| 2-279 | C-4 | B-2 | B-1 |
| 2-380 | C-4 | B-2 | B-2 |
| 2-381 | C-4 | B-2 | B-3 |
| 2-382 | C-4 | B-2 | B-4 |
| 2-383 | C-4 | B-2 | B-5 |
| 2-384 | C-4 | B-2 | B-6 |
| 2-385 | C-4 | B-2 | B-7 |
| 2-386 | C-4 | B-2 | B-8 |
| 2-387 | C-4 | B-2 | B-9 |
| 2-388 | C-4 | B-2 | B-10 |
| 2-389 | C-4 | B-2 | B-11 |
| 2-390 | C-4 | B-2 | B-12 |
| 2-391 | C-4 | B-3 | B-1 |
| 2-392 | C-4 | B-3 | B-2 |
| 2-393 | C-4 | B-3 | B-3 |
| 2-394 | C-4 | B-3 | B-4 |
| 2-395 | C-4 | B-3 | B-5 |
| 2-396 | C-4 | B-3 | B-6 |

TABLE 15

| Cmpd No. | Grp 5 | *—Y³—Ar² | *—Y⁴—Ar³ |
|---|---|---|---|
| 2-397 | C-4 | B-3 | B-7 |
| 2-398 | C-4 | B-3 | B-8 |
| 2-399 | C-4 | B-3 | B-9 |
| 2-400 | C-4 | B-3 | B-10 |
| 2-401 | C-4 | B-3 | B-11 |
| 2-402 | C-4 | B-3 | B-12 |
| 2-403 | C-4 | B-4 | B-1 |
| 2-404 | C-4 | B-4 | B-2 |
| 2-405 | C-4 | B-4 | B-3 |
| 2-406 | C-4 | B-4 | B-4 |
| 2-407 | C-4 | B-4 | B-5 |
| 2-408 | C-4 | B-4 | B-6 |
| 2-409 | C-4 | B-4 | B-7 |
| 2-410 | C-4 | B-4 | B-8 |
| 2-411 | C-4 | B-4 | B-9 |
| 2-412 | C-4 | B-4 | B-10 |
| 2-413 | C-4 | B-4 | B-11 |
| 2-414 | C-4 | B-4 | B-12 |
| 2-415 | C-4 | B-5 | B-1 |
| 2-416 | C-4 | B-5 | B-2 |
| 2-417 | C-4 | B-5 | B-3 |
| 2-418 | C-4 | B-5 | B-4 |
| 2-419 | C-4 | B-5 | B-5 |
| 2-420 | C-4 | B-5 | B-6 |
| 2-421 | C-4 | B-5 | B-7 |
| 2-422 | C-4 | B-5 | B-8 |
| 2-423 | C-4 | B-5 | B-9 |
| 2-424 | C-4 | B-5 | B-10 |
| 2-425 | C-4 | B-5 | B-11 |
| 2-426 | C-4 | B-5 | B-12 |
| 2-427 | C-4 | B-6 | B-1 |
| 2-428 | C-4 | B-6 | B-2 |
| 2-429 | C-4 | B-6 | B-3 |
| 2-430 | C-4 | B-6 | B-4 |
| 2-431 | C-4 | B-6 | B-5 |
| 2-432 | C-4 | B-6 | B-6 |
| 2-433 | C-4 | B-6 | B-7 |
| 2-434 | C-4 | B-6 | B-8 |
| 2-435 | C-4 | B-6 | B-9 |
| 2-436 | C-4 | B-6 | B-10 |
| 2-437 | C-4 | B-6 | B-11 |
| 2-438 | C-4 | B-6 | B-12 |
| 2-439 | C-4 | B-7 | B-1 |
| 2-440 | C-4 | B-7 | B-2 |
| 2-441 | C-4 | B-7 | B-3 |
| 2-442 | C-4 | B-7 | B-4 |
| 2-443 | C-4 | B-7 | B-5 |
| 2-444 | C-4 | B-7 | B-6 |
| 2-445 | C-4 | B-7 | B-7 |
| 2-446 | C-4 | B-7 | B-8 |
| 2-447 | C-4 | B-7 | B-9 |
| 2-448 | C-4 | B-7 | B-10 |
| 2-449 | C-4 | B-7 | B-11 |
| 2-450 | C-4 | B-7 | B-12 |
| 2-451 | C-4 | B-8 | B-1 |
| 2-452 | C-4 | B-8 | B-2 |
| 2-453 | C-4 | B-8 | B-3 |
| 2-454 | C-4 | B-8 | B-4 |
| 2-455 | C-4 | B-8 | B-5 |
| 2-456 | C-4 | B-8 | B-6 |
| 2-457 | C-4 | B-8 | B-7 |
| 2-458 | C-4 | B-8 | B-8 |
| 2-459 | C-4 | B-8 | B-9 |
| 2-460 | C-4 | B-8 | B-10 |
| 2-461 | C-4 | B-8 | B-11 |
| 2-462 | C-4 | B-8 | B-12 |
| 2-463 | C-4 | B-9 | B-1 |
| 2-464 | C-4 | B-9 | B-2 |
| 2-465 | C-4 | B-9 | B-3 |
| 2-466 | C-4 | B-9 | B-4 |
| 2-467 | C-4 | B-9 | B-5 |
| 2-468 | C-4 | B-9 | B-6 |
| 2-469 | C-4 | B-9 | B-7 |
| 2-470 | C-4 | B-9 | B-8 |
| 2-471 | C-4 | B-9 | B-9 |
| 2-472 | C-4 | B-9 | B-10 |
| 2-473 | C-4 | B-9 | B-11 |
| 2-474 | C-4 | B-9 | B-12 |
| 2-475 | C-4 | B-10 | B-1 |
| 2-476 | C-4 | B-10 | B-2 |
| 2-477 | C-4 | B-10 | B-3 |
| 2-478 | C-4 | B-10 | B-4 |
| 2-479 | C-4 | B-10 | B-5 |
| 2-480 | C-4 | B-10 | B-6 |
| 2-481 | C-4 | B-10 | B-7 |
| 2-482 | C-4 | B-10 | B-8 |
| 2-483 | C-4 | B-10 | B-9 |
| 2-484 | C-4 | B-10 | B-10 |
| 2-485 | C-4 | B-10 | B-11 |
| 2-486 | C-4 | B-10 | B-12 |
| 2-487 | C-4 | B-11 | B-1 |
| 2-488 | C-4 | B-11 | B-2 |
| 2-489 | C-4 | B-11 | B-3 |
| 2-490 | C-4 | B-11 | B-4 |
| 2-491 | C-4 | B-11 | B-5 |
| 2-492 | C-4 | B-11 | B-6 |
| 2-493 | C-4 | B-11 | B-7 |
| 2-494 | C-4 | B-11 | B-8 |
| 2-495 | C-4 | B-11 | B-9 |
| 2-496 | C-4 | B-11 | B-10 |
| 2-497 | C-4 | B-11 | B-11 |
| 2-498 | C-4 | B-11 | B-12 |
| 2-499 | C-4 | B-12 | B-1 |
| 2-500 | C-4 | B-12 | B-2 |
| 2-501 | C-4 | B-12 | B-3 |
| 2-502 | C-4 | B-12 | B-4 |
| 2-503 | C-4 | B-12 | B-5 |
| 2-504 | C-4 | B-12 | B-6 |
| 2-505 | C-4 | B-12 | B-7 |
| 2-506 | C-4 | B-12 | B-8 |
| 2-507 | C-4 | B-12 | B-9 |
| 2-508 | C-4 | B-12 | B-10 |
| 2-509 | C-4 | B-12 | B-11 |
| 2-510 | C-4 | B-12 | B-12 |
| 2-511 | C-5 | B-1 | B-1 |
| 2-512 | C-5 | B-1 | B-2 |
| 2-513 | C-5 | B-1 | B-3 |
| 2-514 | C-5 | B-1 | B-4 |
| 2-515 | C-5 | B-1 | B-5 |
| 2-516 | C-5 | B-1 | B-6 |
| 2-517 | C-5 | B-1 | B-7 |
| 2-518 | C-5 | B-1 | B-8 |
| 2-519 | C-5 | B-1 | B-9 |
| 2-520 | C-5 | B-1 | B-10 |
| 2-521 | C-5 | B-1 | B-11 |
| 2-522 | C-5 | B-1 | B-12 |
| 2-523 | C-5 | B-2 | B-1 |
| 2-524 | C-5 | B-2 | B-2 |
| 2-525 | C-5 | B-2 | B-3 |
| 2-526 | C-5 | B-2 | B-4 |
| 2-527 | C-5 | B-2 | B-5 |
| 2-528 | C-5 | B-2 | B-6 |

TABLE 16

| Cmpd No. | Grp 5 | *—Y³—Ar² | *—Y⁴—Ar³ |
|---|---|---|---|
| 2-529 | C-5 | B-2 | B-7 |
| 2-530 | C-5 | B-2 | B-8 |
| 2-531 | C-5 | B-2 | B-9 |
| 2-532 | C-5 | B-2 | B-10 |
| 2-533 | C-5 | B-2 | B-11 |
| 2-534 | C-5 | B-2 | B-12 |
| 2-535 | C-5 | B-3 | B-1 |
| 2-536 | C-5 | B-3 | B-2 |
| 2-537 | C-5 | B-3 | B-3 |
| 2-538 | C-5 | B-3 | B-4 |
| 2-539 | C-5 | B-3 | B-5 |
| 2-540 | C-5 | B-3 | B-6 |
| 2-541 | C-5 | B-3 | B-7 |

TABLE 16-continued

| Cmpd No. | Grp 5 | *—Y³—Ar² | *—Y⁴—Ar³ |
|---|---|---|---|
| 2-542 | C-5 | B-3 | B-8 |
| 2-543 | C-5 | B-3 | B-9 |
| 2-544 | C-5 | B-3 | B-10 |
| 2-545 | C-5 | B-3 | B-11 |
| 2-546 | C-5 | B-3 | B-12 |
| 2-547 | C-5 | B-4 | B-1 |
| 2-548 | C-5 | B-4 | B-2 |
| 2-549 | C-5 | B-4 | B-3 |
| 2-550 | C-5 | B-4 | B-4 |
| 2-551 | C-5 | B-4 | B-5 |
| 2-552 | C-5 | B-4 | B-6 |
| 2-553 | C-5 | B-4 | B-7 |
| 2-554 | C-5 | B-4 | B-8 |
| 2-555 | C-5 | B-4 | B-9 |
| 2-556 | C-5 | B-4 | B-10 |
| 2-557 | C-5 | B-4 | B-11 |
| 2-558 | C-5 | B-4 | B-12 |
| 2-559 | C-5 | B-5 | B-1 |
| 2-560 | C-5 | B-5 | B-2 |
| 2-561 | C-5 | B-5 | B-3 |
| 2-562 | C-5 | B-5 | B-4 |
| 2-563 | C-5 | B-5 | B-5 |
| 2-564 | C-5 | B-5 | B-6 |
| 2-565 | C-5 | B-5 | B-7 |
| 2-566 | C-5 | B-5 | B-8 |
| 2-567 | C-5 | B-5 | B-9 |
| 2-568 | C-5 | B-5 | B-10 |
| 2-569 | C-5 | B-5 | B-11 |
| 2-570 | C-5 | B-5 | B-12 |
| 2-571 | C-5 | B-6 | B-1 |
| 2-572 | C-5 | B-6 | B-2 |
| 2-573 | C-5 | B-6 | B-3 |
| 2-574 | C-5 | B-6 | B-4 |
| 2-575 | C-5 | B-6 | B-5 |
| 2-576 | C-5 | B-6 | B-6 |
| 2-577 | C-5 | B-6 | B-7 |
| 2-578 | C-5 | B-6 | B-8 |
| 2-579 | C-5 | B-6 | B-9 |
| 2-580 | C-5 | B-6 | B-10 |
| 2-581 | C-5 | B-6 | B-11 |
| 2-582 | C-5 | B-6 | B-12 |
| 2-583 | C-5 | B-7 | B-1 |
| 2-584 | C-5 | B-7 | B-2 |
| 2-585 | C-5 | B-7 | B-3 |
| 2-586 | C-5 | B-7 | B-4 |
| 2-587 | C-5 | B-7 | B-5 |
| 2-588 | C-5 | B-7 | B-6 |
| 2-589 | C-5 | B-7 | B-7 |
| 2-590 | C-5 | B-7 | B-8 |
| 2-591 | C-5 | B-7 | B-9 |
| 2-592 | C-5 | B-7 | B-10 |
| 2-593 | C-5 | B-7 | B-11 |
| 2-594 | C-5 | B-7 | B-12 |
| 2-595 | C-5 | B-8 | B-1 |
| 2-596 | C-5 | B-8 | B-2 |
| 2-597 | C-5 | B-8 | B-3 |
| 2-598 | C-5 | B-8 | B-4 |
| 2-599 | C-5 | B-8 | B-5 |
| 2-600 | C-5 | B-8 | B-6 |
| 2-601 | C-5 | B-8 | B-7 |
| 2-602 | C-5 | B-8 | B-8 |
| 2-603 | C-5 | B-8 | B-9 |
| 2-604 | C-5 | B-8 | B-10 |
| 2-605 | C-5 | B-8 | B-11 |
| 2-606 | C-5 | B-8 | B-12 |
| 2-607 | C-5 | B-9 | B-1 |
| 2-608 | C-5 | B-9 | B-2 |
| 2-609 | C-5 | B-9 | B-3 |
| 2-610 | C-5 | B-9 | B-4 |
| 2-611 | C-5 | B-9 | B-5 |
| 2-612 | C-5 | B-9 | B-6 |
| 2-613 | C-5 | B-9 | B-7 |
| 2-614 | C-5 | B-9 | B-8 |
| 2-615 | C-5 | B-9 | B-9 |
| 2-616 | C-5 | B-9 | B-10 |
| 2-617 | C-5 | B-9 | B-11 |
| 2-618 | C-5 | B-9 | B-12 |
| 2-619 | C-5 | B-10 | B-1 |
| 2-620 | C-5 | B-10 | B-2 |
| 2-621 | C-5 | B-10 | B-3 |
| 2-622 | C-5 | B-10 | B-4 |
| 2-623 | C-5 | B-10 | B-5 |
| 2-624 | C-5 | B-10 | B-6 |
| 2-625 | C-5 | B-10 | B-7 |
| 2-626 | C-5 | B-10 | B-8 |
| 2-627 | C-5 | B-10 | B-9 |
| 2-628 | C-5 | B-10 | B-10 |
| 2-629 | C-5 | B-10 | B-11 |
| 2-630 | C-5 | B-10 | B-12 |
| 2-631 | C-5 | B-11 | B-1 |
| 2-632 | C-5 | B-11 | B-2 |
| 2-633 | C-5 | B-11 | B-3 |
| 2-634 | C-5 | B-11 | B-4 |
| 2-635 | C-5 | B-11 | B-5 |
| 2-636 | C-5 | B-11 | B-6 |
| 2-637 | C-5 | B-11 | B-7 |
| 2-638 | C-5 | B-11 | B-8 |
| 2-639 | C-5 | B-11 | B-9 |
| 2-640 | C-5 | B-11 | B-10 |
| 2-641 | C-5 | B-11 | B-11 |
| 2-642 | C-5 | B-11 | B-12 |
| 2-643 | C-5 | B-12 | B-1 |
| 2-644 | C-5 | B-12 | B-2 |
| 2-645 | C-5 | B-12 | B-3 |
| 2-646 | C-5 | B-12 | B-4 |
| 2-647 | C-5 | B-12 | B-5 |
| 2-648 | C-5 | B-12 | B-6 |
| 2-649 | C-5 | B-12 | B-7 |
| 2-650 | C-5 | B-12 | B-8 |
| 2-651 | C-5 | B-12 | B-9 |
| 2-652 | C-5 | B-12 | B-10 |
| 2-653 | C-5 | B-12 | B-11 |
| 2-654 | C-5 | B-12 | B-12 |
| 2-655 | C-6 | B-1 | B-1 |
| 2-656 | C-6 | B-1 | B-2 |
| 2-657 | C-6 | B-1 | B-3 |
| 2-658 | C-6 | B-1 | B-4 |
| 2-659 | C-6 | B-1 | B-5 |
| 2-660 | C-6 | B-1 | B-6 |

TABLE 17

| Cmpd No. | Grp 5 | *—Y³—Ar² | *—Y⁴—Ar³ |
|---|---|---|---|
| 2-661 | C-6 | B-1 | B-7 |
| 2-662 | C-6 | B-1 | B-8 |
| 2-663 | C-6 | B-1 | B-9 |
| 2-664 | C-6 | B-1 | B-10 |
| 2-665 | C-6 | B-1 | B-11 |
| 2-666 | C-6 | B-1 | B-12 |
| 2-667 | C-6 | B-2 | B-1 |
| 2-668 | C-6 | B-2 | B-2 |
| 2-669 | C-6 | B-2 | B-3 |
| 2-670 | C-6 | B-2 | B-4 |
| 2-671 | C-6 | B-2 | B-5 |
| 2-672 | C-6 | B-2 | B-6 |
| 2-673 | C-6 | B-2 | B-7 |
| 2-674 | C-6 | B-2 | B-8 |
| 2-675 | C-6 | B-2 | B-9 |
| 2-676 | C-6 | B-2 | B-10 |
| 2-677 | C-6 | B-2 | B-11 |
| 2-678 | C-6 | B-2 | B-12 |
| 2-679 | C-6 | B-3 | B-1 |
| 2-680 | C-6 | B-3 | B-2 |
| 2-681 | C-6 | B-3 | B-3 |
| 2-682 | C-6 | B-3 | B-4 |
| 2-683 | C-6 | B-3 | B-5 |
| 2-684 | C-6 | B-3 | B-6 |
| 2-685 | C-6 | B-3 | B-7 |
| 2-686 | C-6 | B-3 | B-8 |

TABLE 17-continued

| Cmpd No. | Grp 5 | *—Y³—Ar² | *—Y⁴—Ar³ |
| --- | --- | --- | --- |
| 2-687 | C-6 | B-3 | B-9 |
| 2-688 | C-6 | B-3 | B-10 |
| 2-689 | C-6 | B-3 | B-11 |
| 2-690 | C-6 | B-3 | B-12 |
| 2-691 | C-6 | B-4 | B-1 |
| 2-692 | C-6 | B-4 | B-2 |
| 2-693 | C-6 | B-4 | B-3 |
| 2-694 | C-6 | B-4 | B-4 |
| 2-695 | C-6 | B-4 | B-5 |
| 2-696 | C-6 | B-4 | B-6 |
| 2-697 | C-6 | B-4 | B-7 |
| 2-698 | C-6 | B-4 | B-8 |
| 2-699 | C-6 | B-4 | B-9 |
| 2-700 | C-6 | B-4 | B-10 |
| 2-701 | C-6 | B-4 | B-11 |
| 2-702 | C-6 | B-4 | B-12 |
| 2-703 | C-6 | B-5 | B-1 |
| 2-704 | C-6 | B-5 | B-2 |
| 2-705 | C-6 | B-5 | B-3 |
| 2-706 | C-6 | B-5 | B-4 |
| 2-707 | C-6 | B-5 | B-5 |
| 2-708 | C-6 | B-5 | B-6 |
| 2-709 | C-6 | B-5 | B-7 |
| 2-710 | C-6 | B-5 | B-8 |
| 2-711 | C-6 | B-5 | B-9 |
| 2-712 | C-6 | B-5 | B-10 |
| 2-713 | C-6 | B-5 | B-11 |
| 2-714 | C-6 | B-5 | B-12 |
| 2-715 | C-6 | B-6 | B-1 |
| 2-716 | C-6 | B-6 | B-2 |
| 2-717 | C-6 | B-6 | B-3 |
| 2-718 | C-6 | B-6 | B-4 |
| 2-719 | C-6 | B-6 | B-5 |
| 2-720 | C-6 | B-6 | B-6 |
| 2-721 | C-6 | B-6 | B-7 |
| 2-722 | C-6 | B-6 | B-8 |
| 2-723 | C-6 | B-6 | B-9 |
| 2-724 | C-6 | B-6 | B-10 |
| 2-725 | C-6 | B-6 | B-11 |
| 2-726 | C-6 | B-6 | B-12 |
| 2-727 | C-6 | B-7 | B-1 |
| 2-728 | C-6 | B-7 | B-2 |
| 2-729 | C-6 | B-7 | B-3 |
| 2-730 | C-6 | B-7 | B-4 |
| 2-731 | C-6 | B-7 | B-5 |
| 2-732 | C-6 | B-7 | B-6 |
| 2-733 | C-6 | B-7 | B-7 |
| 2-734 | C-6 | B-7 | B-8 |
| 2-735 | C-6 | B-7 | B-9 |
| 2-736 | C-6 | B-7 | B-10 |
| 2-737 | C-6 | B-7 | B-11 |
| 2-738 | C-6 | B-7 | B-12 |
| 2-739 | C-6 | B-8 | B-1 |
| 2-740 | C-6 | B-8 | B-2 |
| 2-741 | C-6 | B-8 | B-3 |
| 2-742 | C-6 | B-8 | B-4 |
| 2-743 | C-6 | B-8 | B-5 |
| 2-744 | C-6 | B-8 | B-6 |
| 2-745 | C-6 | B-8 | B-7 |
| 2-746 | C-6 | B-8 | B-8 |
| 2-747 | C-6 | B-8 | B-9 |
| 2-748 | C-6 | B-8 | B-10 |
| 2-749 | C-6 | B-8 | B-11 |
| 2-750 | C-6 | B-8 | B-12 |
| 2-751 | C-6 | B-9 | B-1 |
| 2-752 | C-6 | B-9 | B-2 |
| 2-753 | C-6 | B-9 | B-3 |
| 2-754 | C-6 | B-9 | B-4 |
| 2-755 | C-6 | B-9 | B-5 |
| 2-756 | C-6 | B-9 | B-6 |
| 2-757 | C-6 | B-9 | B-7 |
| 2-758 | C-6 | B-9 | B-8 |
| 2-759 | C-6 | B-9 | B-9 |
| 2-760 | C-6 | B-9 | B-10 |
| 2-761 | C-6 | B-9 | B-11 |
| 2-762 | C-6 | B-9 | B-12 |
| 2-763 | C-6 | B-10 | B-1 |
| 2-764 | C-6 | B-10 | B-2 |
| 2-765 | C-6 | B-10 | B-3 |
| 2-766 | C-6 | B-10 | B-4 |
| 2-767 | C-6 | B-10 | B-5 |
| 2-768 | C-6 | B-10 | B-6 |
| 2-769 | C-6 | B-10 | B-7 |
| 2-770 | C-6 | B-10 | B-8 |
| 2-771 | C-6 | B-10 | B-9 |
| 2-772 | C-6 | B-10 | B-10 |
| 2-773 | C-6 | B-10 | B-11 |
| 2-774 | C-6 | B-10 | B-12 |
| 2-775 | C-6 | B-11 | B-1 |
| 2-776 | C-6 | B-11 | B-2 |
| 2-777 | C-6 | B-11 | B-3 |
| 2-778 | C-6 | B-11 | B-4 |
| 2-779 | C-6 | B-11 | B-5 |
| 2-780 | C-6 | B-11 | B-6 |
| 2-781 | C-6 | B-11 | B-7 |
| 2-782 | C-6 | B-11 | B-8 |
| 2-783 | C-6 | B-11 | B-9 |
| 2-784 | C-6 | B-11 | B-10 |
| 2-785 | C-6 | B-11 | B-11 |
| 2-786 | C-6 | B-11 | B-12 |
| 2-787 | C-6 | B-12 | B-1 |
| 2-788 | C-6 | B-12 | B-2 |
| 2-789 | C-6 | B-12 | B-3 |
| 2-790 | C-6 | B-12 | B-4 |
| 2-791 | C-6 | B-12 | B-5 |
| 2-792 | C-6 | B-12 | B-6 |

TABLE 18

| Cmpd No. | Grp 5 | *—Y³—Ar² | *—Y⁴—Ar³ |
| --- | --- | --- | --- |
| 2-793 | C-6 | B-12 | B-7 |
| 2-794 | C-6 | B-12 | B-8 |
| 2-795 | C-6 | B-12 | B-9 |
| 2-796 | C-6 | B-12 | B-10 |
| 2-797 | C-6 | B-12 | B-11 |
| 2-798 | C-6 | B-12 | B-12 |
| 2-799 | C-7 | B-1 | B-1 |
| 2-800 | C-7 | B-1 | B-2 |
| 2-801 | C-7 | B-1 | B-3 |
| 2-802 | C-7 | B-1 | B-4 |
| 2-803 | C-7 | B-1 | B-5 |
| 2-804 | C-7 | B-1 | B-6 |
| 2-805 | C-7 | B-1 | B-7 |
| 2-806 | C-7 | B-1 | B-8 |
| 2-807 | C-7 | B-1 | B-9 |
| 2-808 | C-7 | B-1 | B-10 |
| 2-809 | C-7 | B-1 | B-11 |
| 2-810 | C-7 | B-1 | B-12 |
| 2-811 | C-7 | B-2 | B-1 |
| 2-812 | C-7 | B-2 | B-2 |
| 2-813 | C-7 | B-2 | B-3 |
| 2-814 | C-7 | B-2 | B-4 |
| 2-815 | C-7 | B-2 | B-5 |
| 2-816 | C-7 | B-2 | B-6 |
| 2-817 | C-7 | B-2 | B-7 |
| 2-818 | C-7 | B-2 | B-8 |
| 2-819 | C-7 | B-2 | B-9 |
| 2-820 | C-7 | B-2 | B-10 |
| 2-821 | C-7 | B-2 | B-11 |
| 2-822 | C-7 | B-2 | B-12 |
| 2-823 | C-7 | B-3 | B-1 |
| 2-824 | C-7 | B-3 | B-2 |
| 2-825 | C-7 | B-3 | B-3 |
| 2-826 | C-7 | B-3 | B-4 |
| 2-827 | C-7 | B-3 | B-5 |
| 2-828 | C-7 | B-3 | B-6 |
| 2-829 | C-7 | B-3 | B-7 |
| 2-830 | C-7 | B-3 | B-8 |
| 2-831 | C-7 | B-3 | B-9 |

TABLE 18-continued

| Cmpd No. | Grp 5 | *—Y³—Ar² | *—Y⁴—Ar³ |
|---|---|---|---|
| 2-832 | C-7 | B-3 | B-10 |
| 2-833 | C-7 | B-3 | B-11 |
| 2-834 | C-7 | B-3 | B-12 |
| 2-835 | C-7 | B-4 | B-1 |
| 2-836 | C-7 | B-4 | B-2 |
| 2-837 | C-7 | B-4 | B-3 |
| 2-838 | C-7 | B-4 | B-4 |
| 2-839 | C-7 | B-4 | B-5 |
| 2-840 | C-7 | B-4 | B-6 |
| 2-841 | C-7 | B-4 | B-7 |
| 2-842 | C-7 | B-4 | B-8 |
| 2-843 | C-7 | B-4 | B-9 |
| 2-844 | C-7 | B-4 | B-10 |
| 2-845 | C-7 | B-4 | B-11 |
| 2-846 | C-7 | B-4 | B-12 |
| 2-847 | C-7 | B-5 | B-1 |
| 2-848 | C-7 | B-5 | B-2 |
| 2-849 | C-7 | B-5 | B-3 |
| 2-850 | C-7 | B-5 | B-4 |
| 2-851 | C-7 | B-5 | B-5 |
| 2-852 | C-7 | B-5 | B-6 |
| 2-853 | C-7 | B-5 | B-7 |
| 2-854 | C-7 | B-5 | B-8 |
| 2-855 | C-7 | B-5 | B-9 |
| 2-856 | C-7 | B-5 | B-10 |
| 2-857 | C-7 | B-5 | B-11 |
| 2-858 | C-7 | B-5 | B-12 |
| 2-859 | C-7 | B-6 | B-1 |
| 2-860 | C-7 | B-6 | B-2 |
| 2-861 | C-7 | B-6 | B-3 |
| 2-862 | C-7 | B-6 | B-4 |
| 2-863 | C-7 | B-6 | B-5 |
| 2-864 | C-7 | B-6 | B-6 |
| 2-865 | C-7 | B-6 | B-7 |
| 2-866 | C-7 | B-6 | B-8 |
| 2-867 | C-7 | B-6 | B-9 |
| 2-868 | C-7 | B-6 | B-10 |
| 2-869 | C-7 | B-6 | B-11 |
| 2-870 | C-7 | B-6 | B-12 |
| 2-871 | C-7 | B-7 | B-1 |
| 2-872 | C-7 | B-7 | B-2 |
| 2-873 | C-7 | B-7 | B-3 |
| 2-874 | C-7 | B-7 | B-4 |
| 2-875 | C-7 | B-7 | B-5 |
| 2-876 | C-7 | B-7 | B-6 |
| 2-877 | C-7 | B-7 | B-7 |
| 2-878 | C-7 | B-7 | B-8 |
| 2-879 | C-7 | B-7 | B-9 |
| 2-880 | C-7 | B-7 | B-10 |
| 2-881 | C-7 | B-7 | B-11 |
| 2-882 | C-7 | B-7 | B-12 |
| 2-883 | C-7 | B-8 | B-1 |
| 2-884 | C-7 | B-8 | B-2 |
| 2-885 | C-7 | B-8 | B-3 |
| 2-886 | C-7 | B-8 | B-4 |
| 2-887 | C-7 | B-8 | B-5 |
| 2-888 | C-7 | B-8 | B-6 |
| 2-889 | C-7 | B-8 | B-7 |
| 2-890 | C-7 | B-8 | B-8 |
| 2-891 | C-7 | B-8 | B-9 |
| 2-892 | C-7 | B-8 | B-10 |
| 2-893 | C-7 | B-8 | B-11 |
| 2-894 | C-7 | B-8 | B-12 |
| 2-895 | C-7 | B-9 | B-1 |
| 2-896 | C-7 | B-9 | B-2 |
| 2-897 | C-7 | B-9 | B-3 |
| 2-898 | C-7 | B-9 | B-4 |
| 2-899 | C-7 | B-9 | B-5 |
| 2-900 | C-7 | B-9 | B-6 |
| 2-901 | C-7 | B-9 | B-7 |
| 2-902 | C-7 | B-9 | B-8 |
| 2-903 | C-7 | B-9 | B-9 |
| 2-904 | C-7 | B-9 | B-10 |
| 2-905 | C-7 | B-9 | B-11 |
| 2-906 | C-7 | B-9 | B-12 |
| 2-907 | C-7 | B-10 | B-1 |
| 2-908 | C-7 | B-10 | B-2 |
| 2-909 | C-7 | B-10 | B-3 |
| 2-910 | C-7 | B-10 | B-4 |
| 2-911 | C-7 | B-10 | B-5 |
| 2-912 | C-7 | B-10 | B-6 |
| 2-913 | C-7 | B-10 | B-7 |
| 2-914 | C-7 | B-10 | B-8 |
| 2-915 | C-7 | B-10 | B-9 |
| 2-916 | C-7 | B-10 | B-10 |
| 2-917 | C-7 | B-10 | B-11 |
| 2-918 | C-7 | B-10 | B-12 |
| 2-919 | C-7 | B-11 | B-1 |
| 2-920 | C-7 | B-11 | B-2 |
| 2-921 | C-7 | B-11 | B-3 |
| 2-922 | C-7 | B-11 | B-4 |
| 2-923 | C-7 | B-11 | B-5 |
| 2-924 | C-7 | B-11 | B-6 |

TABLE 19

| Cmpd No. | Grp 5 | *—Y³—Ar² | *—Y⁴—Ar³ |
|---|---|---|---|
| 2-925 | C-7 | B-11 | B-7 |
| 2-926 | C-7 | B-11 | B-8 |
| 2-927 | C-7 | B-11 | B-9 |
| 2-928 | C-7 | B-11 | B-10 |
| 2-929 | C-7 | B-11 | B-11 |
| 2-930 | C-7 | B-11 | B-12 |
| 2-931 | C-7 | B-12 | B-1 |
| 2-932 | C-7 | B-12 | B-2 |
| 2-933 | C-7 | B-12 | B-3 |
| 2-934 | C-7 | B-12 | B-4 |
| 2-935 | C-7 | B-12 | B-5 |
| 2-936 | C-7 | B-12 | B-6 |
| 2-937 | C-7 | B-12 | B-7 |
| 2-938 | C-7 | B-12 | B-8 |
| 2-939 | C-7 | B-12 | B-9 |
| 2-940 | C-7 | B-12 | B-10 |
| 2-941 | C-7 | B-12 | B-11 |
| 2-942 | C-7 | B-12 | B-12 |
| 2-943 | C-8 | B-1 | B-1 |
| 2-944 | C-8 | B-1 | B-2 |
| 2-945 | C-8 | B-1 | B-3 |
| 2-946 | C-8 | B-1 | B-4 |
| 2-947 | C-8 | B-1 | B-5 |
| 2-948 | C-8 | B-1 | B-6 |
| 2-949 | C-8 | B-1 | B-7 |
| 2-950 | C-8 | B-1 | B-8 |
| 2-951 | C-8 | B-1 | B-9 |
| 2-952 | C-8 | B-1 | B-10 |
| 2-953 | C-8 | B-1 | B-11 |
| 2-954 | C-8 | B-1 | B-12 |
| 2-955 | C-8 | B-2 | B-2 |
| 2-956 | C-8 | B-2 | B-3 |
| 2-957 | C-8 | B-2 | B-4 |
| 2-958 | C-8 | B-2 | B-5 |
| 2-959 | C-8 | B-2 | B-6 |
| 2-960 | C-8 | B-2 | B-7 |
| 2-961 | C-8 | B-2 | B-8 |
| 2-962 | C-8 | B-2 | B-9 |
| 2-963 | C-8 | B-2 | B-10 |
| 2-964 | C-8 | B-2 | B-11 |
| 2-965 | C-8 | B-2 | B-12 |
| 2-966 | C-8 | B-3 | B-3 |
| 2-967 | C-8 | B-3 | B-4 |
| 2-968 | C-8 | B-3 | B-5 |
| 2-969 | C-8 | B-3 | B-6 |
| 2-970 | C-8 | B-3 | B-7 |
| 2-971 | C-8 | B-3 | B-8 |
| 2-972 | C-8 | B-3 | B-9 |
| 2-973 | C-8 | B-3 | B-10 |
| 2-974 | C-8 | B-3 | B-11 |
| 2-975 | C-8 | B-3 | B-12 |
| 2-976 | C-8 | B-4 | B-4 |

TABLE 19-continued

| Cmpd No. | Grp 5 | *—Y³—Ar² | *—Y⁴—Ar³ |
|---|---|---|---|
| 2-977 | C-8 | B-4 | B-5 |
| 2-978 | C-8 | B-4 | B-6 |
| 2-979 | C-8 | B-4 | B-7 |
| 2-980 | C-8 | B-4 | B-8 |
| 2-981 | C-8 | B-4 | B-9 |
| 2-982 | C-8 | B-4 | B-10 |
| 2-983 | C-8 | B-4 | B-11 |
| 2-984 | C-8 | B-4 | B-12 |
| 2-985 | C-8 | B-5 | B-5 |
| 2-986 | C-8 | B-5 | B-6 |
| 2-987 | C-8 | B-5 | B-7 |
| 2-988 | C-8 | B-5 | B-8 |
| 2-989 | C-8 | B-5 | B-9 |
| 2-990 | C-8 | B-5 | B-10 |
| 2-991 | C-8 | B-5 | B-11 |
| 2-992 | C-8 | B-5 | B-12 |
| 2-993 | C-8 | B-6 | B-6 |
| 2-994 | C-8 | B-6 | B-7 |
| 2-995 | C-8 | B-6 | B-8 |
| 2-996 | C-8 | B-6 | B-9 |
| 2-997 | C-8 | B-6 | B-10 |
| 2-998 | C-8 | B-6 | B-11 |
| 2-999 | C-8 | B-6 | B-12 |
| 2-1000 | C-8 | B-7 | B-7 |
| 2-1001 | C-8 | B-7 | B-8 |
| 2-1002 | C-8 | B-7 | B-9 |
| 2-1003 | C-8 | B-7 | B-10 |
| 2-1004 | C-8 | B-7 | B-11 |
| 2-1005 | C-8 | B-7 | B-12 |
| 2-1006 | C-8 | B-8 | B-8 |
| 2-1007 | C-8 | B-8 | B-9 |
| 2-1008 | C-8 | B-8 | B-10 |
| 2-1009 | C-8 | B-8 | B-11 |
| 2-1010 | C-8 | B-8 | B-12 |
| 2-1011 | C-8 | B-9 | B-9 |
| 2-1012 | C-8 | B-9 | B-10 |
| 2-1013 | C-8 | B-9 | B-11 |
| 2-1014 | C-8 | B-9 | B-12 |
| 2-1015 | C-8 | B-10 | B-10 |
| 2-1016 | C-8 | B-10 | B-11 |
| 2-1017 | C-8 | B-10 | B-12 |
| 2-1018 | C-8 | B-11 | B-11 |
| 2-1019 | C-8 | B-11 | B-12 |
| 2-1020 | C-8 | B-12 | B-12 |
| 2-1021 | C-9 | B-1 | B-1 |
| 2-1022 | C-9 | B-1 | B-2 |
| 2-1023 | C-9 | B-1 | B-3 |
| 2-1024 | C-9 | B-1 | B-4 |
| 2-1025 | C-9 | B-1 | B-5 |
| 2-1026 | C-9 | B-1 | B-6 |
| 2-1027 | C-9 | B-1 | B-7 |
| 2-1028 | C-9 | B-1 | B-8 |
| 2-1029 | C-9 | B-1 | B-9 |
| 2-1030 | C-9 | B-1 | B-10 |
| 2-1031 | C-9 | B-1 | B-11 |
| 2-1032 | C-9 | B-1 | B-12 |
| 2-1033 | C-9 | B-2 | B-1 |
| 2-1034 | C-9 | B-2 | B-2 |
| 2-1035 | C-9 | B-2 | B-3 |
| 2-1036 | C-9 | B-2 | B-4 |
| 2-1037 | C-9 | B-2 | B-5 |
| 2-1038 | C-9 | B-2 | B-6 |
| 2-1039 | C-9 | B-2 | B-7 |
| 2-1040 | C-9 | B-2 | B-8 |
| 2-1041 | C-9 | B-2 | B-9 |
| 2-1042 | C-9 | B-2 | B-10 |
| 2-1043 | C-9 | B-2 | B-11 |
| 2-1044 | C-9 | B-2 | B-12 |
| 2-1045 | C-9 | B-3 | B-1 |
| 2-1046 | C-9 | B-3 | B-2 |
| 2-1047 | C-9 | B-3 | B-3 |
| 2-1048 | C-9 | B-3 | B-4 |
| 2-1049 | C-9 | B-3 | B-5 |
| 2-1050 | C-9 | B-3 | B-6 |
| 2-1051 | C-9 | B-3 | B-7 |
| 2-1052 | C-9 | B-3 | B-8 |
| 2-1053 | C-9 | B-3 | B-9 |
| 2-1054 | C-9 | B-3 | B-10 |
| 2-1055 | C-9 | B-3 | B-11 |
| 2-1056 | C-9 | B-3 | B-12 |

TABLE 20

| Cmpd No. | Grp 5 | *—Y³—Ar² | *—Y⁴—Ar³ |
|---|---|---|---|
| 2-1057 | C-9 | B-4 | B-1 |
| 2-1058 | C-9 | B-4 | B-2 |
| 2-1059 | C-9 | B-4 | B-3 |
| 2-1060 | C-9 | B-4 | B-4 |
| 2-1061 | C-9 | B-4 | B-5 |
| 2-1062 | C-9 | B-4 | B-6 |
| 2-1063 | C-9 | B-4 | B-7 |
| 2-1064 | C-9 | B-4 | B-8 |
| 2-1065 | C-9 | B-4 | B-9 |
| 2-1066 | C-9 | B-4 | B-10 |
| 2-1067 | C-9 | B-4 | B-11 |
| 2-1068 | C-9 | B-4 | B-12 |
| 2-1069 | C-9 | B-5 | B-1 |
| 2-1070 | C-9 | B-5 | B-2 |
| 2-1071 | C-9 | B-5 | B-3 |
| 2-1072 | C-9 | B-5 | B-4 |
| 2-1073 | C-9 | B-5 | B-5 |
| 2-1074 | C-9 | B-5 | B-6 |
| 2-1075 | C-9 | B-5 | B-7 |
| 2-1076 | C-9 | B-5 | B-8 |
| 2-1077 | C-9 | B-5 | B-9 |
| 2-1078 | C-9 | B-5 | B-10 |
| 2-1079 | C-9 | B-5 | B-11 |
| 2-1080 | C-9 | B-5 | B-12 |
| 2-1081 | C-9 | B-6 | B-1 |
| 2-1082 | C-9 | B-6 | B-2 |
| 2-1083 | C-9 | B-6 | B-3 |
| 2-1084 | C-9 | B-6 | B-4 |
| 2-1085 | C-9 | B-6 | B-5 |
| 2-1086 | C-9 | B-6 | B-6 |
| 2-1087 | C-9 | B-6 | B-7 |
| 2-1088 | C-9 | B-6 | B-8 |
| 2-1089 | C-9 | B-6 | B-9 |
| 2-1090 | C-9 | B-6 | B-10 |
| 2-1091 | C-9 | B-6 | B-11 |
| 2-1092 | C-9 | B-6 | B-12 |
| 2-1093 | C-9 | B-7 | B-1 |
| 2-1094 | C-9 | B-7 | B-2 |
| 2-1095 | C-9 | B-7 | B-3 |
| 2-1096 | C-9 | B-7 | B-4 |
| 2-1097 | C-9 | B-7 | B-5 |
| 2-1098 | C-9 | B-7 | B-6 |
| 2-1099 | C-9 | B-7 | B-7 |
| 2-1100 | C-9 | B-7 | B-8 |
| 2-1101 | C-9 | B-7 | B-9 |
| 2-1102 | C-9 | B-7 | B-10 |
| 2-1103 | C-9 | B-7 | B-11 |
| 2-1104 | C-9 | B-7 | B-12 |
| 2-1105 | C-9 | B-8 | B-1 |
| 2-1106 | C-9 | B-8 | B-2 |
| 2-1107 | C-9 | B-8 | B-3 |
| 2-1108 | C-9 | B-8 | B-4 |
| 2-1109 | C-9 | B-8 | B-5 |
| 2-1110 | C-9 | B-8 | B-6 |
| 2-1111 | C-9 | B-8 | B-7 |
| 2-1112 | C-9 | B-8 | B-8 |
| 2-1113 | C-9 | B-8 | B-9 |
| 2-1114 | C-9 | B-8 | B-10 |
| 2-1115 | C-9 | B-8 | B-11 |
| 2-1116 | C-9 | B-8 | B-12 |
| 2-1117 | C-9 | B-9 | B-1 |
| 2-1118 | C-9 | B-9 | B-2 |
| 2-1119 | C-9 | B-9 | B-3 |
| 2-1120 | C-9 | B-9 | B-4 |
| 2-1121 | C-9 | B-9 | B-5 |
| 2-1122 | C-9 | B-9 | B-6 |

TABLE 20-continued

| Cmpd No. | Grp 5 | *—Y³—Ar² | *—Y⁴—Ar³ |
|---|---|---|---|
| 2-1123 | C-9 | B-9 | B-7 |
| 2-1124 | C-9 | B-9 | B-8 |
| 2-1125 | C-9 | B-9 | B-9 |
| 2-1126 | C-9 | B-9 | B-10 |
| 2-1127 | C-9 | B-9 | B-11 |
| 2-1128 | C-9 | B-9 | B-12 |
| 2-1129 | C-9 | B-10 | B-1 |
| 2-1130 | C-9 | B-10 | B-2 |
| 2-1131 | C-9 | B-10 | B-3 |
| 2-1132 | C-9 | B-10 | B-4 |
| 2-1133 | C-9 | B-10 | B-5 |
| 2-1134 | C-9 | B-10 | B-6 |
| 2-1135 | C-9 | B-10 | B-7 |
| 2-1136 | C-9 | B-10 | B-8 |
| 2-1137 | C-9 | B-10 | B-9 |
| 2-1138 | C-9 | B-10 | B-10 |
| 2-1139 | C-9 | B-10 | B-11 |
| 2-1140 | C-9 | B-10 | B-12 |
| 2-1141 | C-9 | B-11 | B-1 |
| 2-1142 | C-9 | B-11 | B-2 |
| 2-1143 | C-9 | B-11 | B-3 |
| 2-1144 | C-9 | B-11 | B-4 |
| 2-1145 | C-9 | B-11 | B-5 |
| 2-1146 | C-9 | B-11 | B-6 |
| 2-1147 | C-9 | B-11 | B-7 |
| 2-1148 | C-9 | B-11 | B-8 |
| 2-1149 | C-9 | B-11 | B-9 |
| 2-1150 | C-9 | B-11 | B-10 |
| 2-1151 | C-9 | B-11 | B-11 |
| 2-1152 | C-9 | B-11 | B-12 |
| 2-1153 | C-9 | B-12 | B-1 |
| 2-1154 | C-9 | B-12 | B-2 |
| 2-1155 | C-9 | B-12 | B-3 |
| 2-1156 | C-9 | B-12 | B-4 |
| 2-1157 | C-9 | B-12 | B-5 |
| 2-1158 | C-9 | B-12 | B-6 |
| 2-1159 | C-9 | B-12 | B-7 |
| 2-1160 | C-9 | B-12 | B-8 |
| 2-1161 | C-9 | B-12 | B-9 |
| 2-1162 | C-9 | B-12 | B-10 |
| 2-1163 | C-9 | B-12 | B-11 |
| 2-1164 | C-9 | B-12 | B-12 |
| 2-1165 | C-10 | B-1 | B-1 |
| 2-1166 | C-10 | B-1 | B-2 |
| 2-1167 | C-10 | B-1 | B-3 |
| 2-1168 | C-10 | B-1 | B-4 |
| 2-1169 | C-10 | B-1 | B-5 |
| 2-1170 | C-10 | B-1 | B-6 |
| 2-1171 | C-10 | B-1 | B-7 |
| 2-1172 | C-10 | B-1 | B-8 |
| 2-1173 | C-10 | B-1 | B-9 |
| 2-1174 | C-10 | B-1 | B-10 |
| 2-1175 | C-10 | B-1 | B-11 |
| 2-1176 | C-10 | B-1 | B-12 |
| 2-1177 | C-10 | B-2 | B-2 |
| 2-1178 | C-10 | B-2 | B-3 |
| 2-1179 | C-10 | B-2 | B-4 |
| 2-1180 | C-10 | B-2 | B-5 |
| 2-1181 | C-10 | B-2 | B-6 |
| 2-1182 | C-10 | B-2 | B-7 |
| 2-1183 | C-10 | B-2 | B-8 |
| 2-1184 | C-10 | B-2 | B-9 |
| 2-1185 | C-10 | B-2 | B-10 |
| 2-1186 | C-10 | B-2 | B-11 |
| 2-1187 | C-10 | B-2 | B-12 |
| 2-1188 | C-10 | B-3 | B-3 |

TABLE 21

| Cmpd No. | Grp 5 | *—Y³—Ar² | *—Y⁴—Ar³ |
|---|---|---|---|
| 2-1189 | C-10 | B-3 | B-4 |
| 2-1190 | C-10 | B-3 | B-5 |
| 2-1191 | C-10 | B-3 | B-6 |
| 2-1192 | C-10 | B-3 | B-7 |
| 2-1193 | C-10 | B-3 | B-8 |
| 2-1194 | C-10 | B-3 | B-9 |
| 2-1195 | C-10 | B-3 | B-10 |
| 2-1196 | C-10 | B-3 | B-11 |
| 2-1197 | C-10 | B-3 | B-12 |
| 2-1198 | C-10 | B-4 | B-4 |
| 2-1199 | C-10 | B-4 | B-5 |
| 2-1200 | C-10 | B-4 | B-6 |
| 2-1201 | C-10 | B-4 | B-7 |
| 2-1202 | C-10 | B-4 | B-8 |
| 2-1203 | C-10 | B-4 | B-9 |
| 2-1204 | C-10 | B-4 | B-10 |
| 2-1205 | C-10 | B-4 | B-11 |
| 2-1206 | C-10 | B-4 | B-12 |
| 2-1207 | C-10 | B-5 | B-5 |
| 2-1208 | C-10 | B-5 | B-6 |
| 2-1209 | C-10 | B-5 | B-7 |
| 2-1210 | C-10 | B-5 | B-8 |
| 2-1211 | C-10 | B-5 | B-9 |
| 2-1212 | C-10 | B-5 | B-10 |
| 2-1213 | C-10 | B-5 | B-11 |
| 2-1214 | C-10 | B-5 | B-12 |
| 2-1215 | C-10 | B-6 | B-6 |
| 2-1216 | C-10 | B-6 | B-7 |
| 2-1217 | C-10 | B-6 | B-8 |
| 2-1218 | C-10 | B-6 | B-9 |
| 2-1219 | C-10 | B-6 | B-10 |
| 2-1220 | C-10 | B-6 | B-11 |
| 2-1221 | C-10 | B-6 | B-12 |
| 2-1222 | C-10 | B-7 | B-7 |
| 2-1223 | C-10 | B-7 | B-8 |
| 2-1224 | C-10 | B-7 | B-9 |
| 2-1225 | C-10 | B-7 | B-10 |
| 2-1226 | C-10 | B-7 | B-11 |
| 2-1227 | C-10 | B-7 | B-12 |
| 2-1228 | C-10 | B-8 | B-8 |
| 2-1229 | C-10 | B-8 | B-9 |
| 2-1230 | C-10 | B-8 | B-10 |
| 2-1231 | C-10 | B-8 | B-11 |
| 2-1232 | C-10 | B-8 | B-12 |
| 2-1233 | C-10 | B-9 | B-9 |
| 2-1234 | C-10 | B-9 | B-10 |
| 2-1235 | C-10 | B-9 | B-11 |
| 2-1236 | C-10 | B-9 | B-12 |
| 2-1237 | C-10 | B-10 | B-10 |
| 2-1238 | C-10 | B-10 | B-11 |
| 2-1239 | C-10 | B-10 | B-12 |
| 2-1240 | C-10 | B-11 | B-11 |
| 2-1241 | C-10 | B-11 | B-12 |
| 2-1242 | C-10 | B-12 | B-12 |

According to an example embodiment, the second host compound may be represented by the Chemical Formula 5,

[Chemical Formula 5]

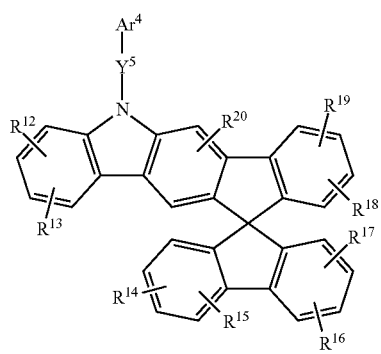

According to the present example embodiment, in the Chemical Formula 5, $Ar^4$ is a substituted or unsubstituted C6 to C30 aryl group, a substituted or unsubstituted C2 to C30 heteroaryl group, or a combination thereof, $Y^5$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, and $R^{12}$ to $R^{20}$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

According to an example embodiment, in the Chemical Formula 5, $Ar^4$ may be a substituent having hole characteristics, for example, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, or a combination thereof.

According to an example embodiment, the second host compound represented by the Chemical Formula 5 may be one of compounds listed in the following Group 6,

[Group 6]

3-1

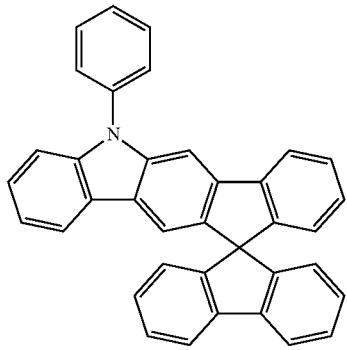

3-2

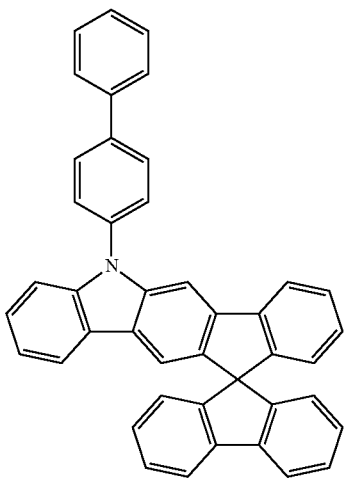

3-3

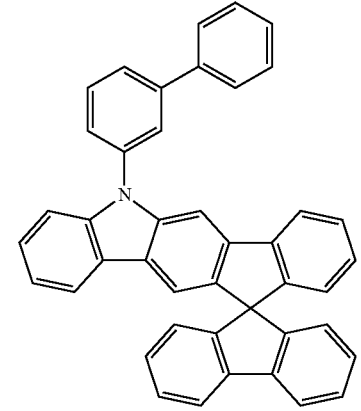

3-4

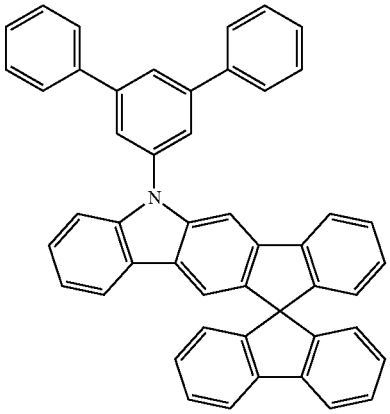

3-5

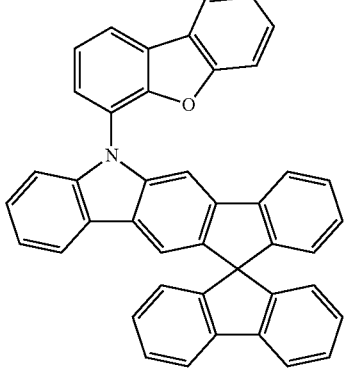

-continued
3-6
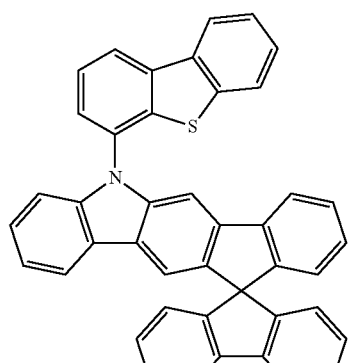
3-7
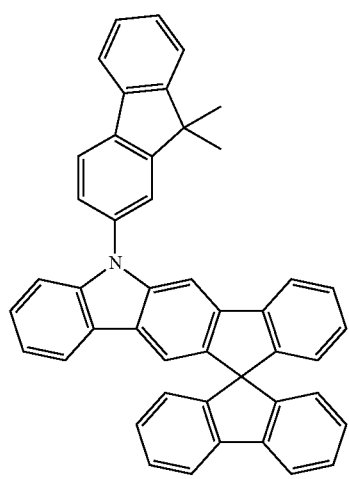
3-8
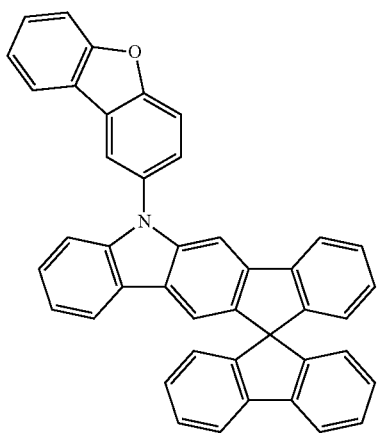
-continued
3-9
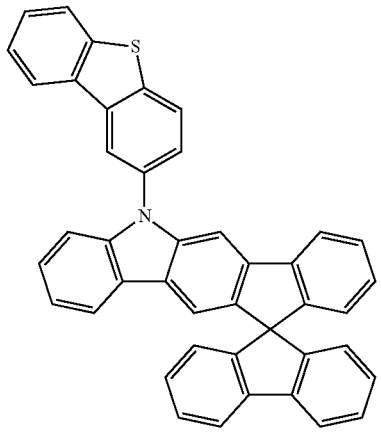
3-10
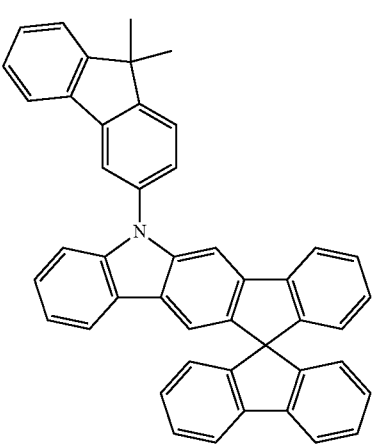
3-11
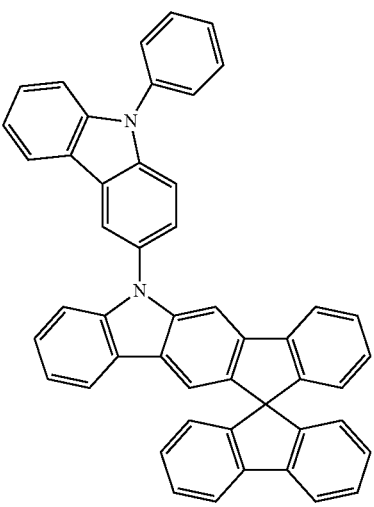

3-12

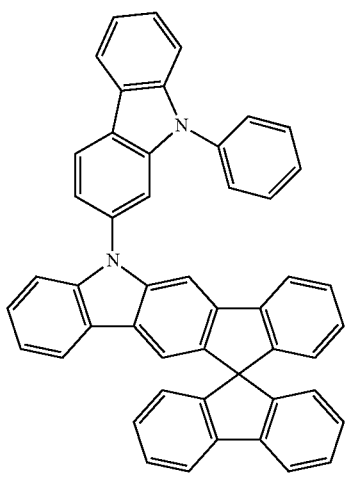

3-13

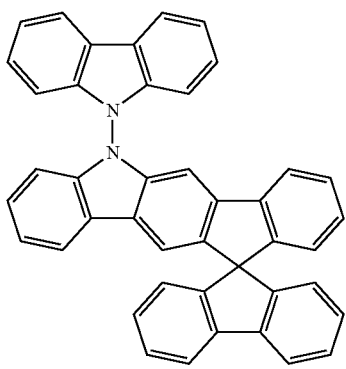

3-14

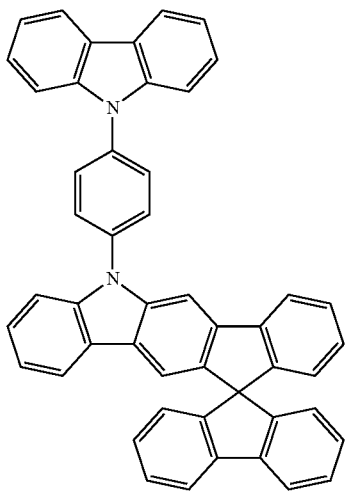

According to an example embodiment, the second host compound may be represented by the Chemical Formula 6 and 7,

[Chemical Formula 6]

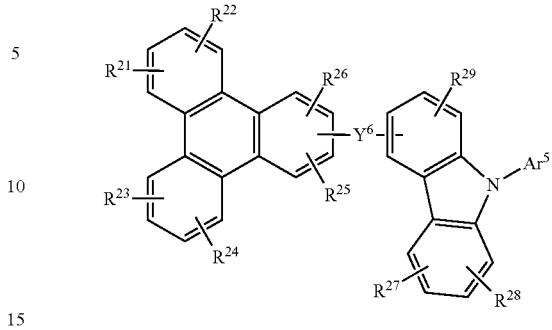

[Chemical Formula 7]

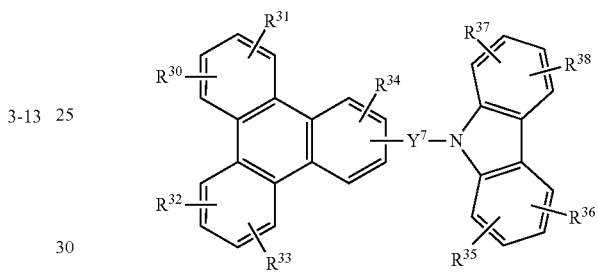

According to the present example embodiment, in the Chemical Formula 6 and 7, $Ar^5$ is a substituted or unsubstituted C6 to C30 aryl group, a substituted or unsubstituted C2 to C30 heteroaryl group, or a combination thereof, $Y^6$ and $Y^7$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, and $R^{21}$ to $R^{38}$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

According to an example embodiment, in the Chemical Formula 6, $Ar^5$ may be a substituent having hole characteristics, for example, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, or a combination thereof.

According to an example embodiment, the second host compound represented by the Chemical Formula 6 and 7 may be one of compounds listed in the following Group 7,

[Group 7]
4-1
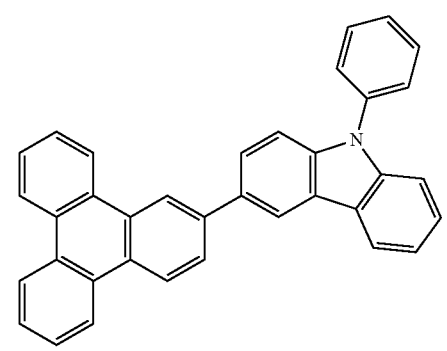
4-2
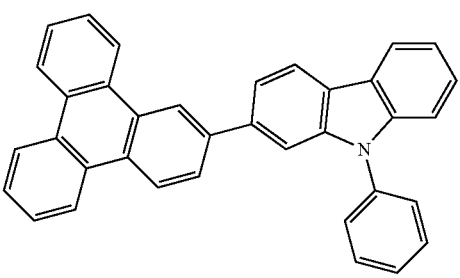
4-3
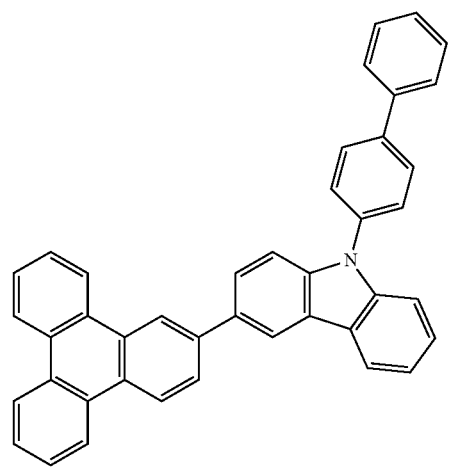
4-4
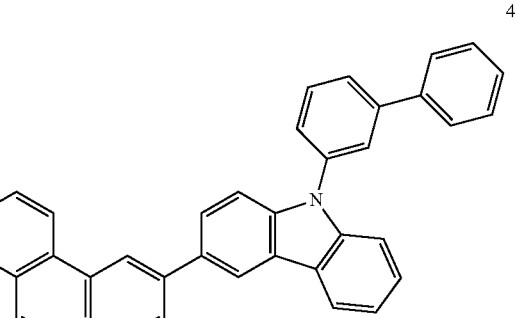
4-5
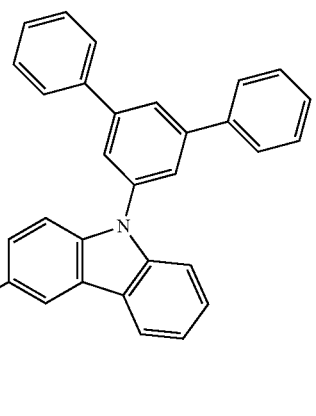
4-6
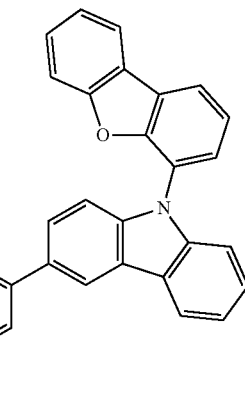
4-7
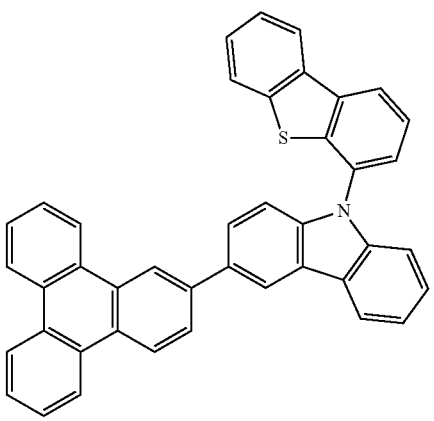

-continued
4-8
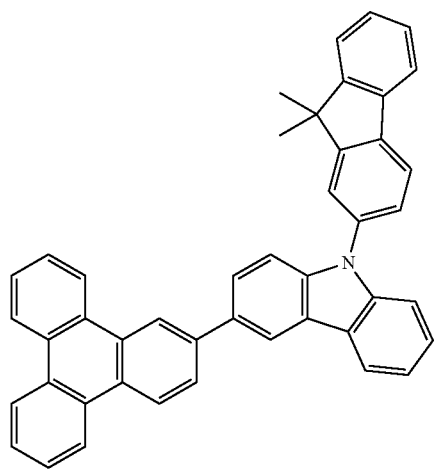
4-9
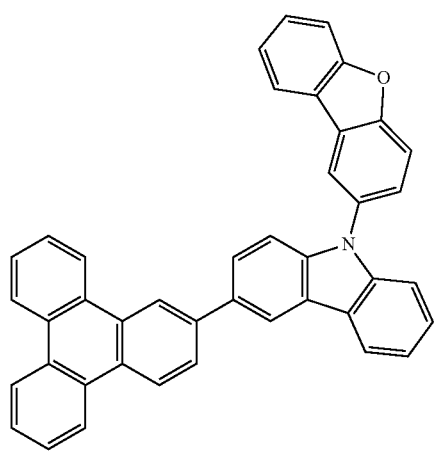
4-10
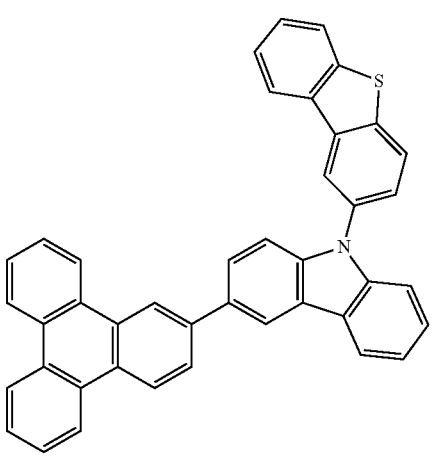
-continued
4-11
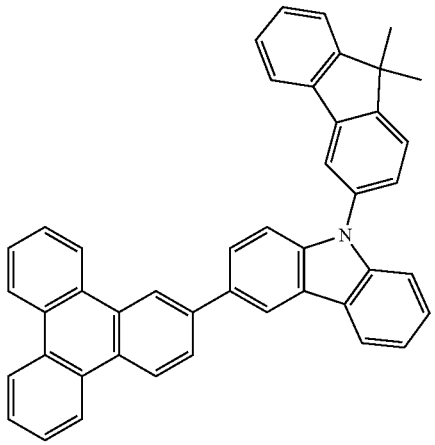
4-12
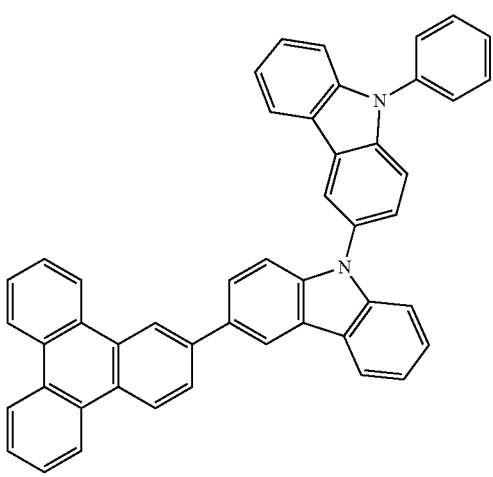
4-13
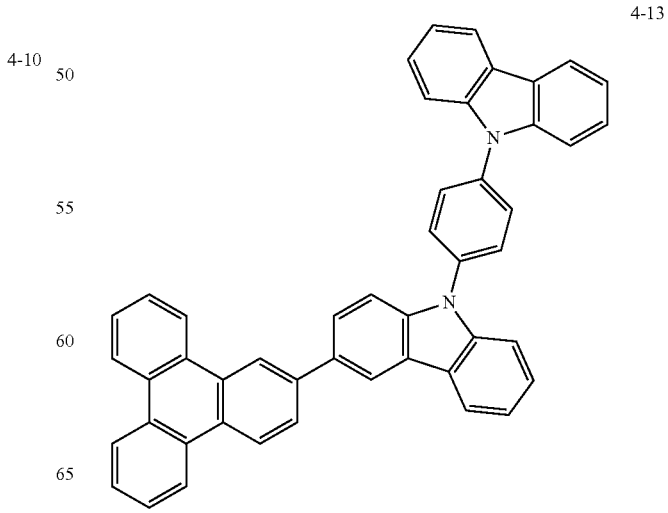

-continued 4-14
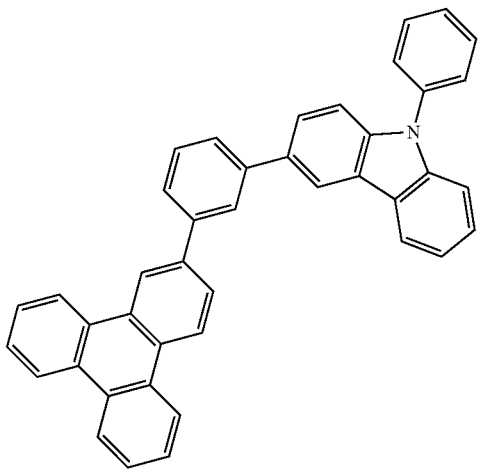

4-15
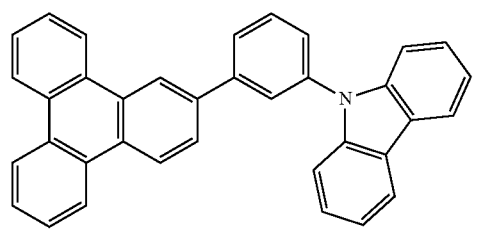

4-16
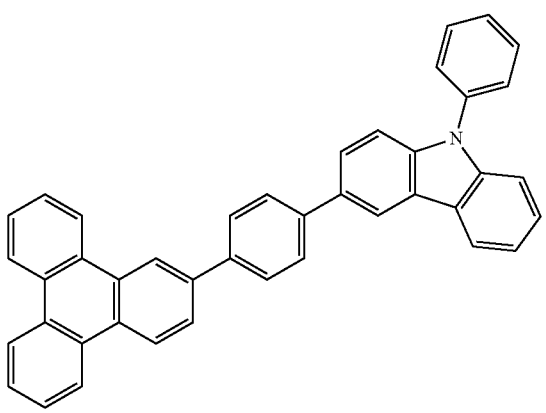

4-17
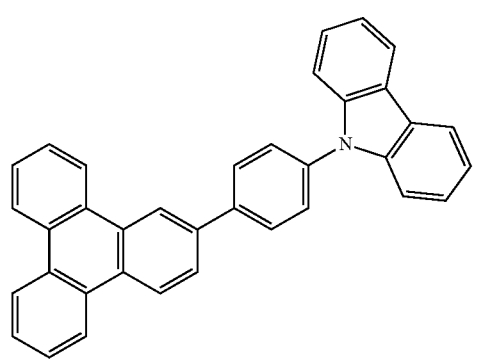

-continued 4-18
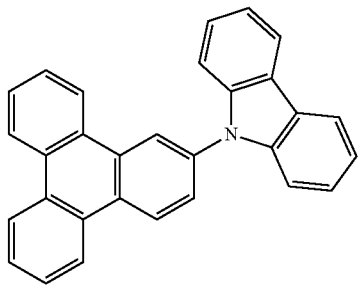

4-19
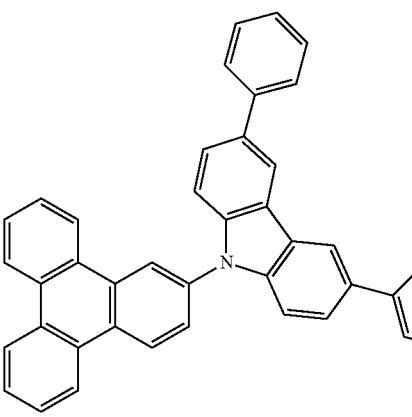

According to an example embodiment, the first host compound is a compound having electron characteristics and the second host compound is a compound having hole characteristics, and these two may realize bipolar characteristics.

According to an example embodiment, the composition is applied to an emission layer of an organic optoelectric device, and thus good interface characteristics and hole and electron transport capability may be improved.

The first host compound and the second host compound may be included in a weight ratio of, for example, about 1:10 to about 10:1.

Within the range, when an emission layer is formed in an appropriate weight ratio using electron transport capability of the first host compound and hole transport capability of the second host compound, bipolar characteristics may be realized and efficiency and life-span may be improved.

The composition may further include at least one host compound besides the first host compound and the second host compound.

The composition may further include a dopant.

The dopant may be, for example, a red, green, or blue dopant, for example, a phosphorescent dopant.

The dopant may be mixed with the first host compound and the second host compound in a small amount to cause light emission, and may be generally a material such as a metal complex that emits light by multiple excitation into a triplet or more.

The dopant may be, for example, an inorganic, organic, or organic/inorganic compound, and one or more kinds thereof may be used.

Examples of the phosphorescent dopant may be an organic metal compound including Ir, Pt, Os, Ti, Zr, Hf, Eu, Tb, Tm, Fe, Co, Ni, Ru, Rh, Pd, or a combination thereof.

The phosphorescent dopant may be, for example, one of compounds represented by the following Chemical Formulae A to C, etc.

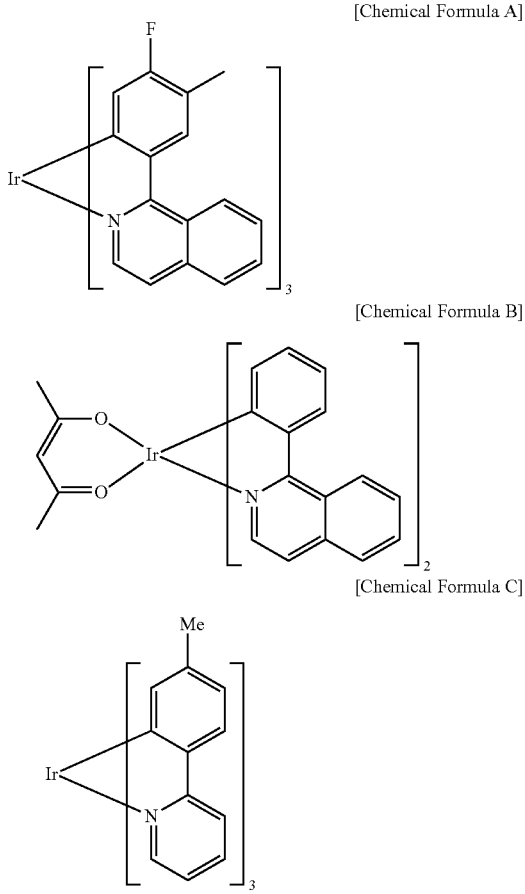

[Chemical Formula A]

[Chemical Formula B]

[Chemical Formula C]

According to an example embodiment, the composition may form a film using a dry film-forming method such as chemical vapor deposition.

Hereinafter, an organic optoelectric device to which the composition according to an embodiment is applied is described.

The organic optoelectric device may be a device to convert electrical energy into photoenergy or vice versa, and may be, for example, an organic photoelectric device, an organic light emitting diode, an organic solar cell, an organic photo-conductor drum, etc.

An organic light emitting diode as one example of an organic optoelectric device according to an embodiment will now be described referring to drawings.

FIGS. 1 and 2 illustrate cross-sectional views of organic light emitting diodes according to example embodiments.

Referring to FIG. 1, an organic optoelectric device 100 according to an example embodiment includes an anode 120 and a cathode 110 facing each other, and an organic layer 105 interposed between the anode 120 and cathode 110.

The anode 120 may be made of a conductor having a large work function to help hole injection, and may be, for example, metal, metal oxide, and/or a conductive polymer.

The anode 120 may be, for example, a metal nickel, platinum, vanadium, chromium, copper, zinc, gold, and the like, or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, etc.

The cathode 110 may be made of a conductor having a small work function to help electron injection, and may be, for example, metal, metal oxide and/or a conductive polymer.

The cathode 110 may be, for example, a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al and BaF$_2$/Ca, etc.

The organic layer 105 may include an emission layer 130 including the composition according to an embodiment. The emission layer 130 may include, for example, the above composition.

Referring to FIG. 2, an organic light emitting diode 200 further includes a hole auxiliary layer 140 as well as an emission layer 130.

The hole auxiliary layer 140 may further increase hole injection and/or hole mobility between the anode 120 and emission layer 130, and block electrons.

The hole auxiliary layer 140 may be, for example, a hole transport layer (HTL), a hole injection layer (HIL), and/or an electron blocking layer, and may include at least one layer.

In an example embodiment, an organic light emitting diode may further include an electron transport layer (ETL), an electron injection layer (EIL), a hole injection layer (HIL), and the like, as an organic thin layer 105 in FIG. 1 or FIG. 2.

The organic light emitting diodes 100 and 200 may be manufactured by, for example, forming an anode or a cathode on a substrate, forming an organic layer in accordance with a dry coating method such as evaporation, sputtering, plasma plating, and ion plating; and forming a cathode or an anode thereon.

The organic light emitting diode may be applied to an organic light emitting diode (OLED) display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Organic Compound

Example 1: Synthesis of First Host Compound

A compound 1-705 as a specific example of the first compound was synthesized through two steps according to the following Reaction Scheme 1.

[Reaction Scheme 1]

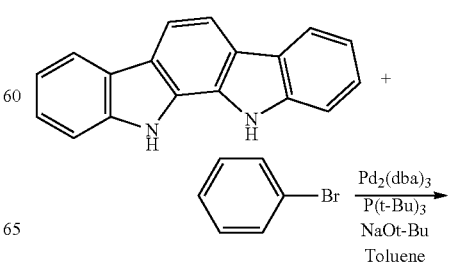

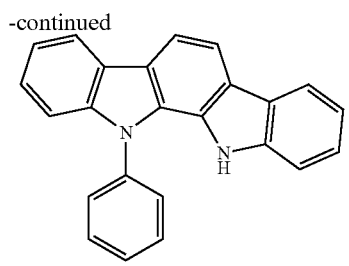

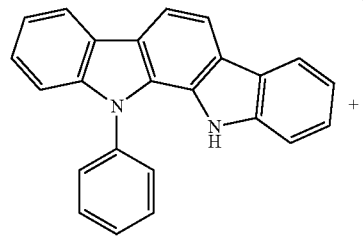

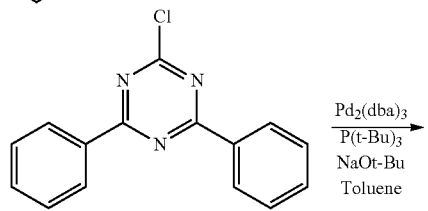

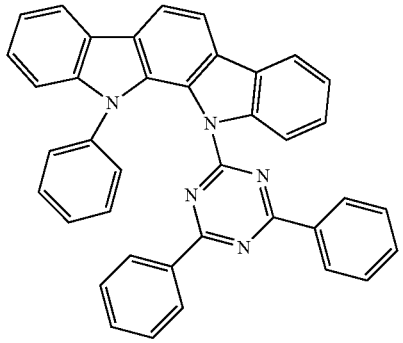

1-705

First Step: Synthesis of 11-phenyl-11,12-dihydroindolo[2,3-a]carbazole 78.35 g (305.69 mmol) of 11,12-dihydroindolo[2,3-a]carbazole, 26.8 mL (254.74 mmol) of bromobenzene, 26.93 g (280.22 mmol) of NaOt-Bu, and 7 g (7.64 mmol) of Pd$_2$(dba)$_3$ were suspended in 1400 mL of toluene, 3.64 mL (15.28 mmol) of P(t-Bu)$_3$ was added thereto, and the mixture was refluxed and agitated for 12 hours.

Distilled water was added thereto for extraction, and an organic layer produced therein was filtered with silica gel.

After removing an organic solution therefrom, a solid product was recrystallized with dichloromethane and n-hexane, obtaining 46.2 g of 11-phenyl-11,12-dihydroindolo[2,3-a]carbazole (yield: 55%, LC Mass M+H$^+$=333.13).

Second Step: Synthesis of Compound 1-705

46.2 g (138.99 mmol) of 11-phenyl-11,12-dihydroindolo[2,3-a]carbazole and 37.2 g (138.99 mmol) of 2-chloro-4,6-diphenyl-1,3,5-triazine, 16.03 g (166.79 mmol) of NaOt-Bu, and 7.63 g (8.34 mmol) of Pd$_2$(dba)$_3$ were suspended in 500 mL of toluene, 12.2 mL (25.02 mmol) of P(t-Bu)$_3$ was added thereto, and the mixture was refluxed and agitated for 12 hours.

Subsequently, distilled water was added thereto for extraction, and an organic layer produced therein was filtered with silica gel.

After removing an organic solution therefrom, a solid product was dissolved in a small amount of dichloromethane, the solution was dropped in methanol for precipitation, and dichloromethane and n-hexane were used for recrystallization, obtaining 27.5 g of a compound 1-705 (a yield: 35%, LC Mass M+H$^+$=564.22).

Examples 2 to 6: Preparation of Compound

A compound was synthesized according to the same method as Example 1 except for using two starting materials provided in the following Table instead of the starting material (corresponding to a starting material 1 in the following Table 22) and A-1 (corresponding to a starting material 2 in the following Table 22) in Example 1,

TABLE 22

| Examples | Starting material 1 | Starting material 2 | Product | Yield (%) LC-Mass (M + H$^+$) |
|---|---|---|---|---|
| 2 | | | 1-707 | 52% 563.22 |

TABLE 22-continued
| Examples | Starting material 1 | Starting material 2 | Product | Yield (%) LC-Mass (M + H+) |
|---|---|---|---|---|
| 3 | 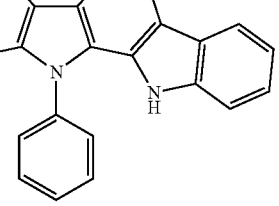 | 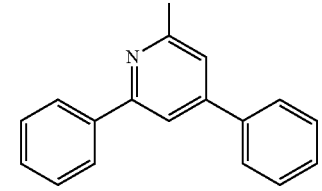 | 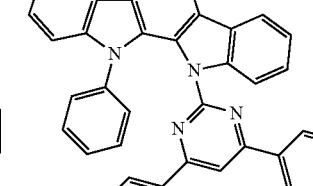<br>1-708 | 48%<br>562.23 |
| 4 | 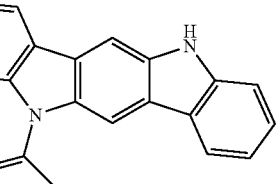 | 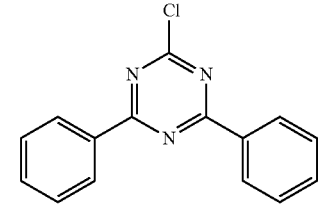 [SMILES: Clc1nc(-c2ccccc2)nc(-c2ccccc2)n1] | 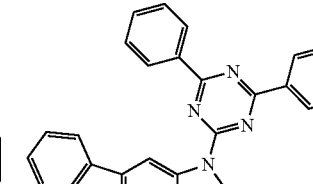<br>1-529 | 65%<br>564.21 |
| 5 | 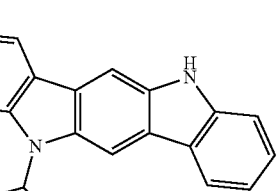 | 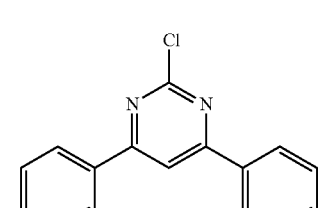 | 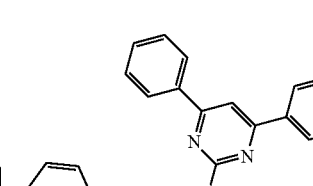<br>1-531 | 61%<br>563.22 |
| 6 | 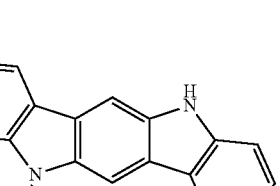 | 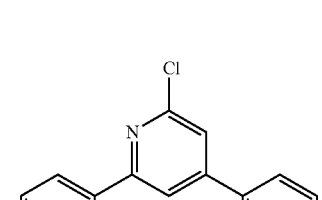 | 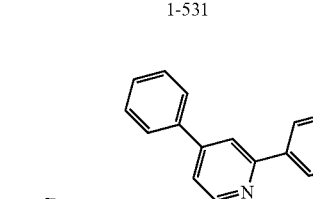<br>1-532 | 59%<br>562.22 |

Example 7: Synthesis of Second Host Compound [Chemical Formula 4]

A synthesis method is the same as the following Reaction Scheme 2.

[Reaction Scheme 2]

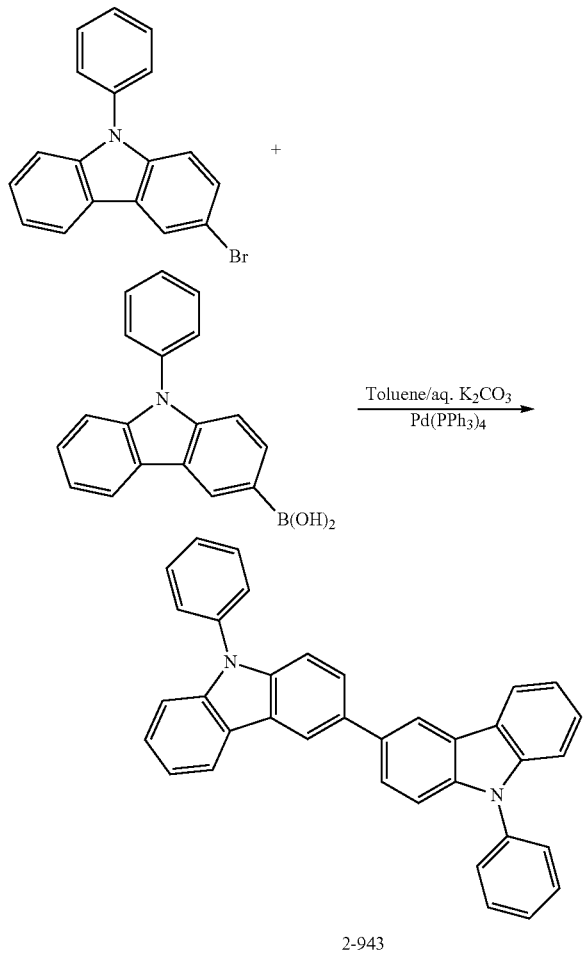

2-943

First Step: Synthesis of Compound 2-943

9.97 g (30.95 mmol) of phenylcarbazolylbromide, 9.78 g (34.05 mmol) of phenylcarbazolylboronic acid, and 12.83 g (92.86 mmol) of potassium carbonate, and 1.07 g (0.93 mmol) of tetrakis-(triphenylphosphine)palladium (0) were suspended in 120 mL of toluene and 50 mL of distilled water, and the suspended solution was refluxed and agitated for 12 hours.

Dichloromethane and distilled water were used for extraction, and an organic layer produced therein was filtered with silica gel.

After removing an organic solution therefrom, a solid product was recrystallized with dichloromethane and n-hexane, obtaining 13.8 g of a compound represented by Chemical Formula 2-943 (yield: 92%, LC Mass M+H$^+$= 485.20).

Examples 8 to 14: Preparation of Compound

The following compounds 2-944, 2-946, 2-949, 2-655, 2-658, 2-511, and 2-514 were synthesized according to the same method as Example 7 except for using starting materials provided in the following Table instead of the phenylcarbazolylbromide (corresponding to a starting material 1 in the following Table 23) and the phenylcarbazolylboronic acid (corresponding to a starting material 2 in the following Table 23) in Example 7,

TABLE 23

| Examples | Starting material 1 | Starting material 2 | Product | Yield (%) LC-Mass (M + H$^+$) |
|---|---|---|---|---|
| 8 | (structure) | (structure) | 2-944 | 90% 561.23 |

TABLE 23-continued
| Examples | Starting material 1 | Starting material 2 | Product | Yield (%) LC-Mass (M + H+) |
|---|---|---|---|---|
| 9 | 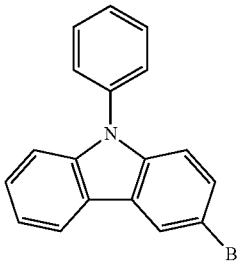 | 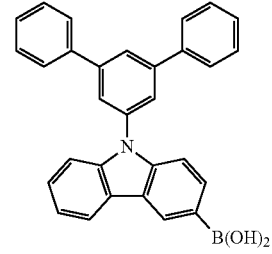 [SMILES: OB(O)c1ccc2c(c1)c1ccccc1n2-c1cc(-c2ccccc2)cc(-c2ccccc2)c1] | 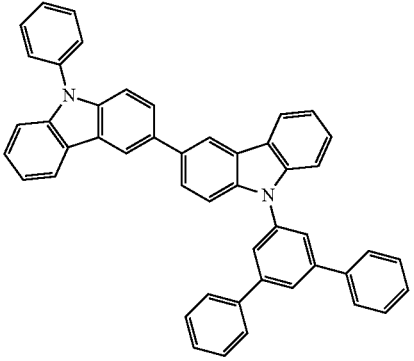<br>2-946 | 85%<br>637.27 |
| 10 | 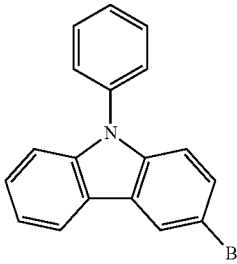 | 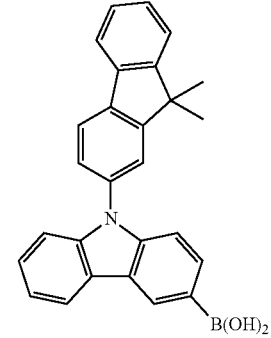 [SMILES: CC1(C)c2ccccc2-c2ccc(-n3c4ccccc4c4cc(B(O)O)ccc43)cc21] | 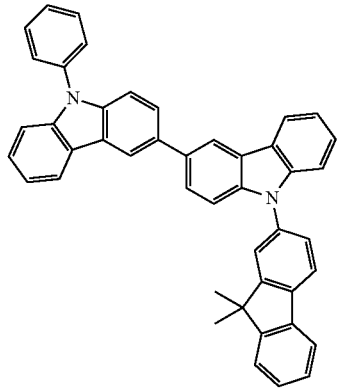<br>2-949 | 82%<br>601.26 |
| 11 | 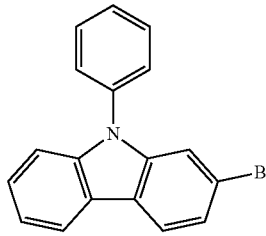 | 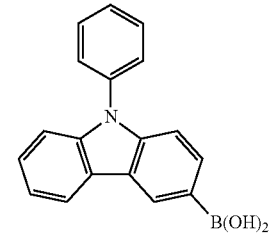 [SMILES: OB(O)c1ccc2c(c1)c1ccccc1n2-c1ccccc1] | 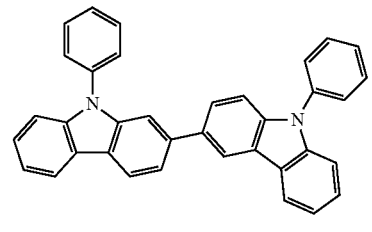<br>2-655 | 84%<br>485.19 |
| 12 | 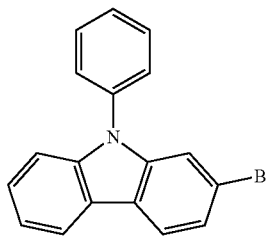 | 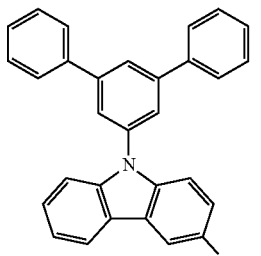 | 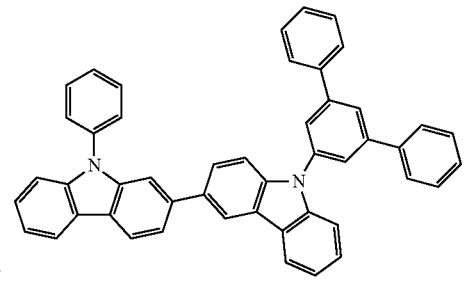<br>2-658 | 80%<br>637.28 |

TABLE 23-continued

| Examples | Starting material 1 | Starting material 2 | Product | Yield (%) LC-Mass (M + H+) |
|---|---|---|---|---|
| 13 | | | 2-511 | 82% 485.19 |
| 14 | | | 2-514 | 83% 637.27 |

Example 15: Synthesis of Second Host Compound [Chemical Formula 5]

An intermediate product was synthesized through two steps as shown in the following Reaction Scheme 3 referring to KR 1247626 (Cheil Industries, Inc., Registered Patent).

[Reaction Scheme 3]

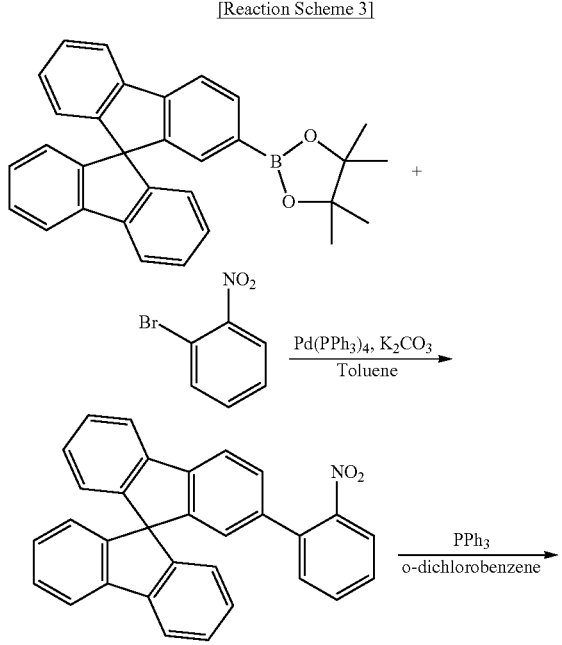

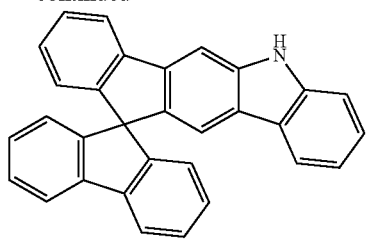

-continued

A compound 3-1 represented by Chemical Formula 5 as a specific example of a second host compound was synthesized according to the following Reaction Scheme 4.

[Reaction Scheme 4]

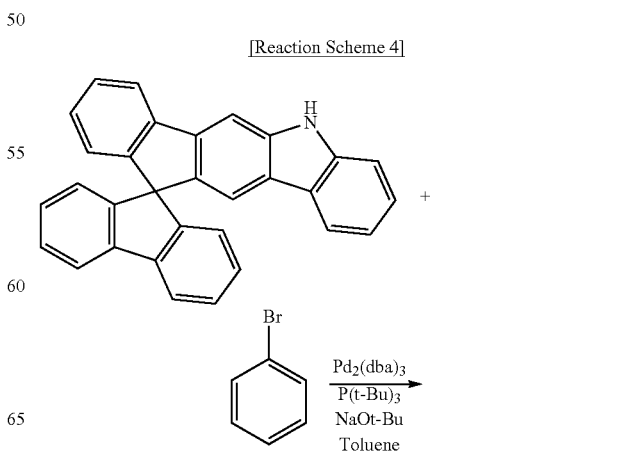

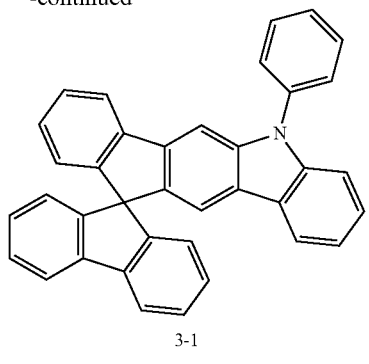

3-1

First Step: Synthesis of Compound 3-1

10 g (24.66 mmol) of spirofluorenoindenocarbazole, 2.59 mL (27.13 mmol) of bromobenzene, 4.74 g (49.32 mmol) of NaOt-Bu, and 0.23 g (0.25 mmol) of $Pd_2(dba)_3$ were suspended in 100 mL of toluene, 0.6 mL (2.47 mmol) of $P(t-Bu)_3$ was added thereto, and the mixture was refluxed and agitated for 12 hours.

Dichloromethane and distilled water were used for extraction, and an organic layer produced therein was filtered with silica gel.

After removing an organic solution therein and performing silica gel column with hexane:dichloromethane=8:2 (v/v), a solid product was recrystallized with dichloromethane and n-hexane, obtaining 10.9 g of a compound 3-1 (yield: 92%, LC Mass $M+H^+$=482.20).

Example 16 to 20: Preparation of Compound

The following compounds 3-2, 3-5, 3-7, 3-11, and 3-14 were obtained according to the same method as Example 15 except for using each starting material provided in the following Table instead of the spirofluorenoindenocarbazole (corresponding to a starting material 1 in the following Table 24) and bromobenzene (corresponding to a starting material 2 in the following Table 24) in Example 15,

TABLE 24

| Examples | Starting material 1 | Starting material 2 | Product | Yield (%) LC-Mass (M + H⁺) |
|---|---|---|---|---|
| 16 | | | | 90% 558.21 |
| 17 | | | | 85% 572.20 |

TABLE 24-continued
| Examples | Starting material 1 | Starting material 2 | Product | Yield (%) LC-Mass (M + H+) |
|---|---|---|---|---|
| 18 | 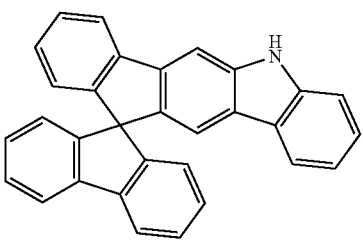 [SMILES: c1ccc2c(c1)-c1ccccc1C21c2ccccc2-c2cc3[nH]c4ccccc4c3cc21] | 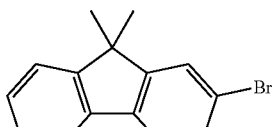 | 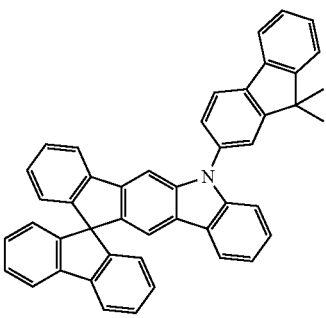<br>3-7 | 87%<br>598.25 |
| 19 | 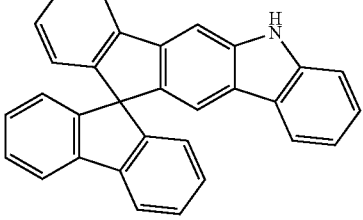 | 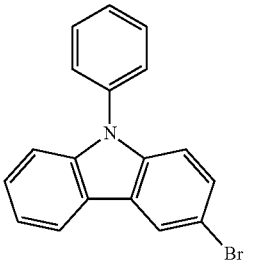 [SMILES: Brc1ccc2c(c1)c1ccccc1n2-c1ccccc1] | 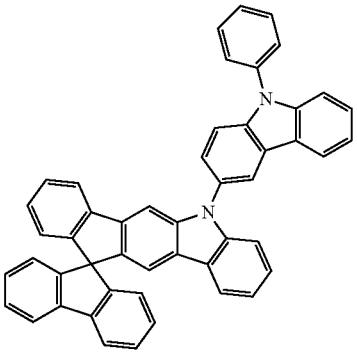<br>3-11 | 85%<br>647.25 |
| 20 | 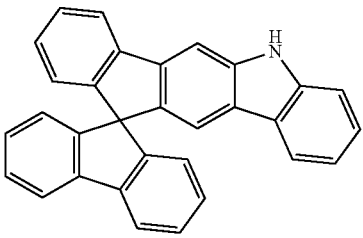 [SMILES: c1ccc2c(c1)-c1ccccc1C21c2ccccc2-c2cc3[nH]c4ccccc4c3cc21] | 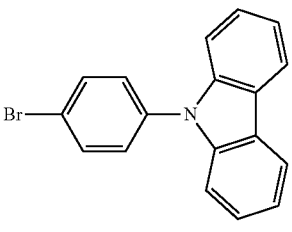 [SMILES: Brc1ccc(-n2c3ccccc3c3ccccc32)cc1] | 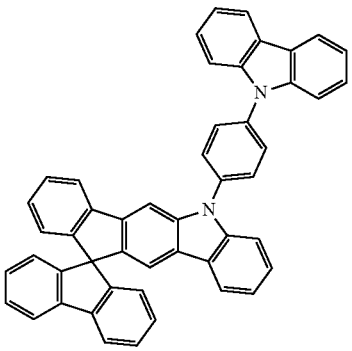<br>3-14 | 84%<br>647.24 |

Example 21: Synthesis of Second Host Compound
[Chemical Formulas 6 to 7]

A compound 4-1 represented by the following Reaction Scheme 5 as a specific example of a second host compound was synthesized as follows.

[Reaction Scheme 5]

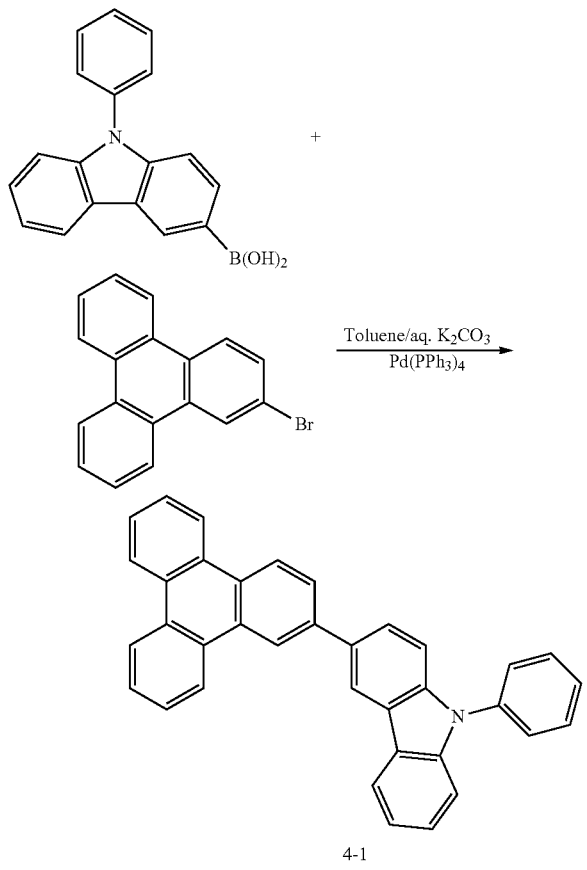

4-1

First Step: Synthesis of Compound 4-1

10 g (34.83 mmol) of phenylcarbazolylboronic acid, 11.77 g (38.31 mmol) of 2-bromotriphenylene, 14.44 g (104.49 mmol) of potassium carbonate, and 0.80 g (0.7 mmol) of tetrakis-(triphenylphosphine)palladium (0) were suspended in 140 mL of toluene and 50 mL of distilled water, and the suspended solution was refluxed and agitated for 12 hours.

Dichloromethane and distilled water were used for extraction, and an organic layer produced therein was filtered with silica gel.

After removing an organic solution therefrom and performing silica gel column with hexane:dichloromethane=7:3 (v/v), a solid product was recrystallized with dichloromethane and n-hexane, obtaining a compound 4-1 14.4 g (yield: 88%, LC Mass M+H$^+$=470.19).

Examples 22 to 25: Preparation of Compound

Compounds 4-2, 4-5, 4-8, and 4-15 were synthesized according to the same method as Example 21 except for using starting materials provided in the following Table instead of the phenylcarbazolylboronic acid (corresponding to a starting material 1 in the following Table 25) and the 2-bromotriphenylene (corresponding to a starting material 2 in the following Table 25) in Example 21.

TABLE 25

| Examples | Starting material 1 | Starting material 2 | Product | Yield (%) LC-Mass (M + H$^+$) |
|---|---|---|---|---|
| 22 | | | | 89% 470.18 |

4-2

TABLE 25-continued

| Examples | Starting material 1 | Starting material 2 | Product | Yield (%) LC-Mass (M + H+) |
|---|---|---|---|---|
| 23 | | | 4-5 | 87% 622.25 |
| 24 | | | 4-8 | 85% 586.25 |
| 25 | | | 4-15 | 85 470.19 |

Example 26: Manufacture of Organic Light Emitting Diode

A 1000 Å-thick ITO was used as an anode, and a 1000 Å-thick aluminum (Al) was used as a cathode.

Specifically, an organic light emitting diode was manufactured by manufacturing the anode by cutting an ITO glass substrate having 15 Ω/cm² of sheet resistance into a size of 50 mm×50 mm×0.7 mm and cleaning with a ultrasonic wave in acetone, isopropyl alcohol, and pure water respectively for 5 minutes, and with UV ozone for 30 minutes.

On the substrate upper, a 800 Å-thick hole transport layer (HTL) was formed by depositing N4,N4'-di(naphthalen-1-yl)-N4,N4'-diphenylbiphenyl-4,4'-diamine (NPB) (80 nm) with a vacuum degree of 650×10⁻⁷ Pa at a deposition speed ranging from 0.1 to 0.3 nm/s.

Subsequently, a 300 Å-thick emission layer was formed by vacuum-depositing the compound 1-705 obtained under the same vacuum deposition condition in Example 1 and the compound 2-943 according to Example 7 in a weight ratio of 1:1 and, simultaneously, doping the host with Ir(ppy)₃ as a phosphorescent dopant.

Herein, 10 wt % of the phosphorescent dopant was deposited by adjusting a speed of depositing the phosphorescent dopant based on 100 wt % of the total amount of the emission layer.

On the emission layer, a 50 Å-thick hole-blocking layer was formed by using bis(2-methyl-8-quinolinolate)-4-(phenylphenolato)aluminum (BAlq) under the same deposition condition.

Subsequently, a 250 Å-thick electron transport layer (ETL) was formed by depositing Alq3 under the same vacuum deposition condition.

LiF and Al were sequentially deposited to form a cathode on the electron transport layer (ETL), manufacturing an organic photoelectric device.

The organic photoelectric device has a structure of ITO/NPB (80 nm)/EML (a compound 1-705 (45 wt %)+a compound 2-943 (45 wt %)+Ir(PPy)3 (10 wt %), 30 nm)/Balq (5 nm)/Alq3 (25 nm)/LiF (1 nm)/Al (100 nm).

Example 27

An organic light emitting diode was manufactured according to the same method as Example 26 except for depositing a compound 1-705 and a compound 2-943 in a weight ratio of 4:1 instead of the compound 1-705 and the compound 2-943 in a weight ratio of 1:1 in Example 26.

Example 28

An organic light emitting diode was manufactured according to the same method as Example 26 except for using a compound 1-705 and a compound 2-943 in a weight ratio of 1:4 instead of the compound 1-705 and the compound 2-943 in a weight ratio of 1:1 in Example 26.

Example 29

An organic light emitting diode was manufactured according to the same method as Example 26 except for using a compound 1-705 and a compound 3-1 in a weight ratio of 1:1 instead of the compound 1-705 and the compound 2-943 in a weight ratio of 1:1 in Example 26.

Example 30

An organic light emitting diode was manufactured according to the same method as Example 26 except for using a compound 1-705 and a compound 4-1 in a weight ratio of 1:1 instead of the compound 1-705 and the compound 2-943 in a weight ratio of 1:1 in Example 26.

Example 31

An organic light emitting diode was manufactured according to the same method as Example 30 except for using a compound 1-705 and a compound 4-1 in a weight ratio of 4:1 instead of the compound 1-705 and the compound 4-1 in a weight ratio of 1:1 in Example 30.

Example 32

An organic light emitting diode was manufactured according to the same method as Example 30 except for using a compound 1-705 and a compound 4-1 in a weight ratio of 1:4 instead of the compound 1-705 and the compound 4-1 in a weight ratio of 1:1 in Example 30.

Example 33

An organic light emitting diode was manufactured according to the same method as Example 30 except for using a compound 1-705 and a compound 4-15 in a weight ratio of 1:1 instead of the compound 1-705 and the compound 4-1 in a weight ratio of 1:1 in Example 30.

Comparative Example 1

An organic light emitting diode was manufactured according to the same method as Example 26 except for only depositing a compound 1-705 as a host instead of the compound 1-705 and the compound 2-943 in a weight ratio of 1:1 in Example 26.

Comparative Example 2

An organic light emitting diode was manufactured according to the same method as Example 26 except for only depositing a compound 2-943 as a host instead of the compound 1-705 and the compound 2-943 in a weight ratio of 1:1 in Example 26.

Comparative Example 3

An organic light emitting diode was manufactured according to the same method as Example 29 except for only depositing a compound 3-1 as a host instead of the compound 1-705 and the compound 3-1 in a weight ratio of 1:1 in Example 29.

Comparative Example 4

An organic light emitting diode was manufactured according to the same method as Example 30 except for only depositing a compound 4-1 as a host instead of the compound 1-705 and the compound 4-1 in a weight ratio of 1:1 in Example 30.

Comparative Example 5

An organic light emitting diode was manufactured according to the same method as Example 26 except for depositing a compound 1-705 and a comparative compound having the following structure formula, HOST-1, in a weight ratio of 1:1 instead of the compound 1-705 and the compound 2-943 in a weight ratio of 1:1 in Example 26.

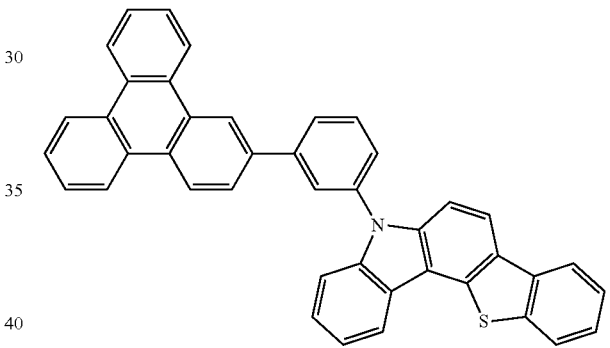

HOST-1

Evaluation

Current density and luminance changes depending on a voltage and luminous efficiency of each organic light emitting diode according to Examples 1 to 8 and Comparative Examples 1 to 5 were measured.

The measurements were specifically performed in the following method, and the results were provided in the following Table 26.

(1) Measurement of Current Density Change Depending on Voltage Change

Current values flowing in the unit device of the manufactured organic light emitting diodes were measured for, while increasing the voltage from 0 V to 10 V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm$^2$) were calculated by using the luminance, current density, and voltages (V) from the items 1) current density change depending on voltage change and 2) luminance change depending on voltage change.

(4) Measurement of Life-Span

Luminance (cd/m²) was maintained at 5000 cd/m² and a time at current efficiency (cd/A) decreases to 95% was measured.

TABLE 26

| | Compound used in emission layer | Driving voltage (V) | Color (EL color) | Efficiency (cd/A) | 95% life-span (h) @ 5000 cd/m² |
|---|---|---|---|---|---|
| Example 26 | 1-705 + 2-943 1:1 | 3.8 | Green | 52.9 | 260 |
| Example 27 | 1-705 + 2-943 4:1 | 3.9 | Green | 37.1 | 330 |
| Example 28 | 1-705 + 2-943 1:4 | 5.3 | Green | 24.5 | 40 |
| Example 29 | 1-705 + 3-1 1:1 | 5.5 | Green | 25.2 | 70 |
| Example 30 | 1-705 + 4-1 1:1 | 4.3 | Green | 26.3 | 340 |
| Example 31 | 1-705 + 4-1 4:1 | 4.3 | Green | 36.8 | 360 |
| Example 32 | 1-705 + 4-1 1:4 | 5.1 | Green | 45.3 | 300 |
| Example 33 | 1-705 + 4-15 1:1 | 4.8 | Green | 24.1 | 230 |
| Comparative Example 1 | 1-705 | 4.3 | Green | 24.2 | 240 |
| Comparative Example 2 | 2-943 | 7.1 | Green | 1.7 | — |
| Comparative Example 3 | 3-1 | 8.5 | Green | 25.6 | — |
| Comparative Example 4 | 4-1 | 7.9 | Green | 16.5 | 22 |
| Comparative Example 5 | 1-705 + HOST-1 1:1 | 5.0 | Green | 22.9 | 200 |

From the Table 26, the organic light emitting diodes according to Examples 26 to 33 showed remarkably improved luminous efficiency and life-span compared with the organic light emitting diodes according to Comparative Examples 1 to 3.

Specifically, the organic light emitting diodes according to Example 30 to Example 32 showed improved efficiency and superbly improved life-span compared with each comparative example, Comparative Examples 1 and 4.

By way of summation and review, examples of an organic optoelectric device may include an organic photoelectric device, an organic light emitting diode, an organic solar cell, and an organic photo-conductor drum, and the like. Among them, the organic light emitting diode (OLED) has recently drawn attention due to an increase in demand for flat panel displays. The organic light emitting diode converts electrical energy into light by applying current to an organic light emitting material, and has a structure in which an organic layer is interposed between an anode and a cathode. The organic layer may include an emission layer and an auxiliary layer, and the auxiliary layer may include at least one selected from, for example, a hole injection layer, a hole transport layer, an electron blocking layer, an electron transport layer, an electron injection layer, and a hole blocking layer, which may help improve efficiency and stability of an organic light emitting diode.

Performance of an organic light emitting diode may be affected by characteristics of the organic layer, and among them, may be mainly affected by characteristics of an organic material of the organic layer.

Increasing hole and electron mobility, and simultaneously increasing electrochemical stability of an organic material may be useful for application of the organic light emitting diode to a large-size flat panel display.

As described above, an embodiment provides a composition that may help realize an organic optoelectric device having high efficiency and long life-span. Efficiency and life-span may be improved due to bipolar characteristics of the hole transportable host and the electron transportable host.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition, comprising:
    a first host compound including moieties represented by the following Chemical Formulae 1 to 3 that are sequentially bonded with each other, and
    a second host compound represented by the following Chemical Formula 4,

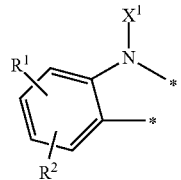

[Chemical Formula 1]

[Chemical Formula 2]

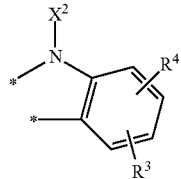

[Chemical Formula 3]

wherein, in the Chemical Formulae 1 to 3,
    $X^1$ is *—$Y^1$-ET,
    $X^2$ is *—$Y^2$—$Ar^1$,
    ET is a substituent for accepting an electron when an electric field is applied,
    $Ar^1$ is a substituted or unsubstituted C6 to C30 aryl group, a substituted or unsubstituted C2 to C30 heteroaryl group, or a combination thereof,
    $Y^1$ and $Y^2$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof,
    L is a substituted or unsubstituted C2 or C3 alkenylene group or a substituted or unsubstituted C6 to C20 arylene group, and $R^1$ to $R^4$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof,

[Chemical Formula 4]

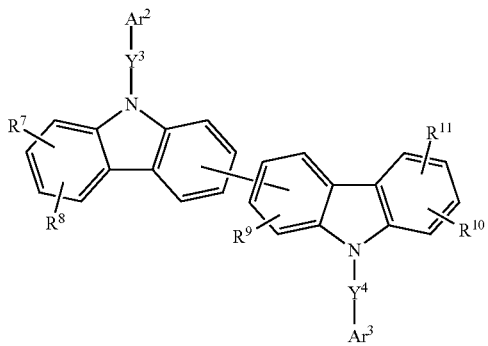

wherein, in the Chemical Formula 4,
$Ar^2$ and $Ar^3$ are each independently an unsubstituted C6 to C30 aryl group, a substituted or unsubstituted carbazolyl group, a substituted or unsubstituted fluorenyl group, or a combination thereof, provided that, when $Ar^2$ or $Ar^3$ is a substituted group, the substituted group has hole characteristics, $Y^3$ and $Y^4$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, and $R^7$ to $R^{11}$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

2. The composition as claimed in claim 1, wherein the ET is represented by the Chemical Formula 1a:

[Chemical Formula 1a]

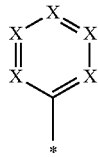

wherein, in the Chemical Formula 1a,
each X is independently N or $CR^a$,
at least one of X is N, and
$R^a$ is hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

3. The composition as claimed in claim 1, wherein the ET is one of the substituents listed in the following Group 1:

[Group 1]

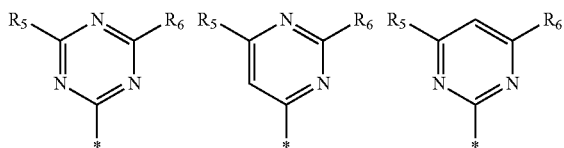

-continued

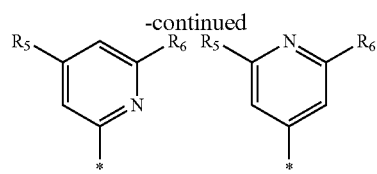

wherein, in the Group 1,
$R^5$ and $R^6$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof.

4. The composition as claimed in claim 1, wherein the $X^1$ is one of the substituents listed in the following Group 2:

[Group 2]

A-1

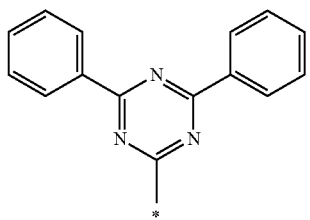

A-2

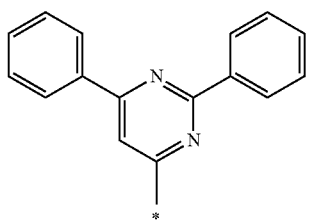

A-3

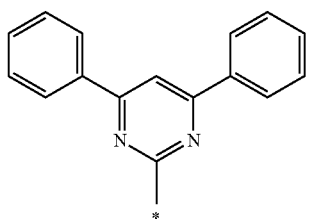

A-4

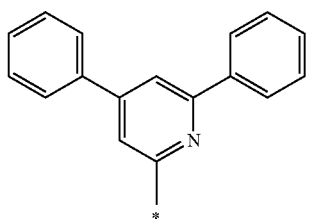

A-5

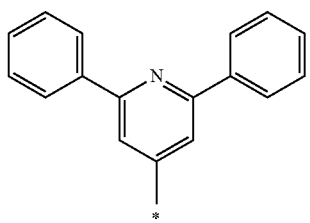

A-6 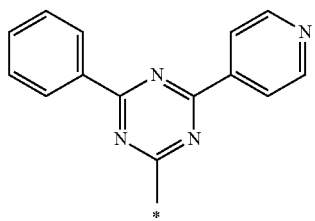
A-7 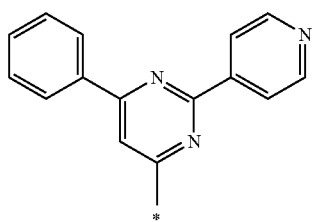
A-8 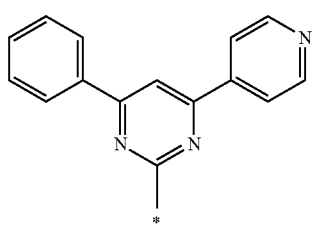
A-9 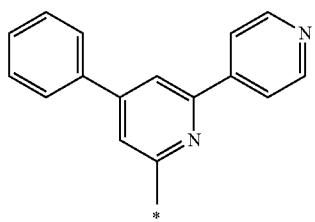
A-10 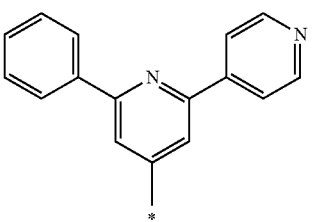
A-11 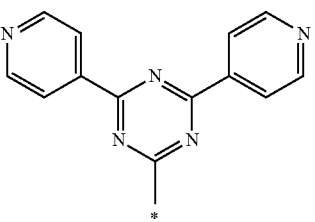
A-12 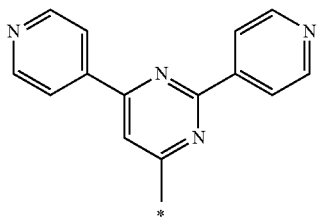
A-13 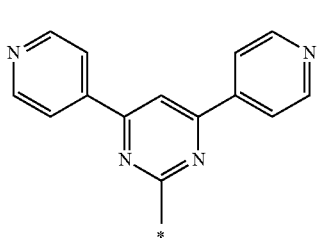
A-14 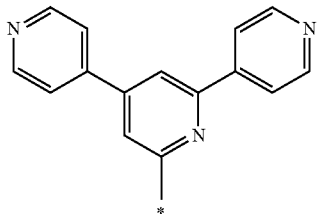
A-15 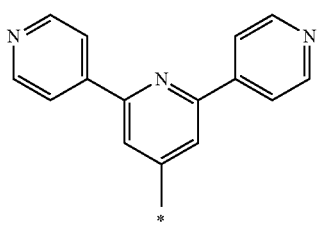
A-16 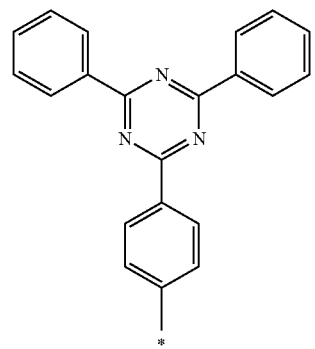

A-17
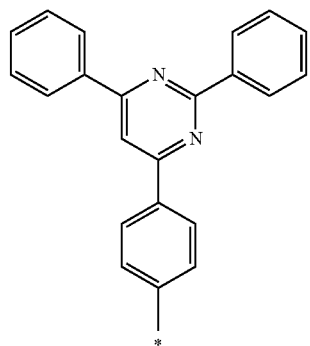
A-18
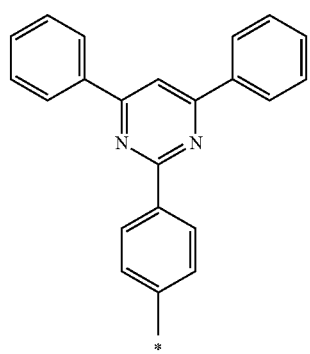
A-19
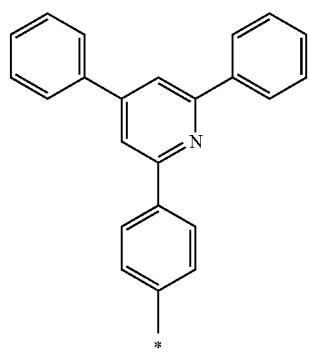
A-20
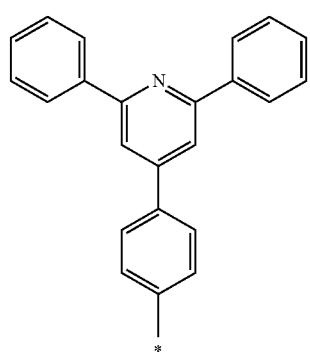
A-21
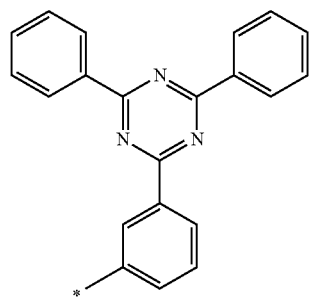
A-22
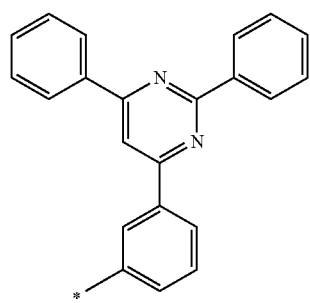
A-23
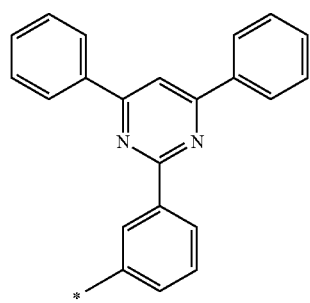
A-24
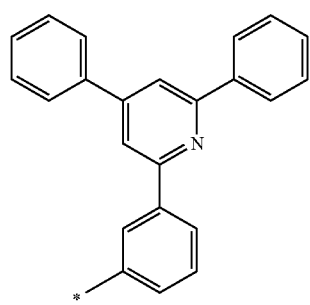
A-25
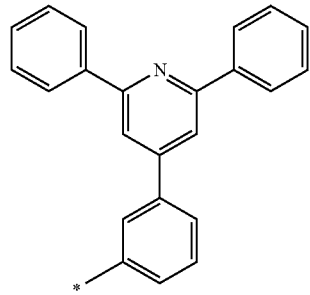

A-26
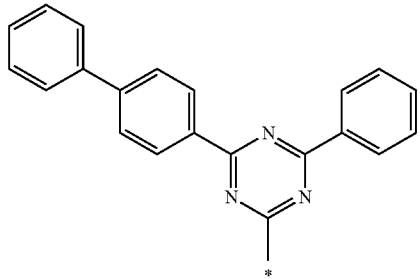
A-27
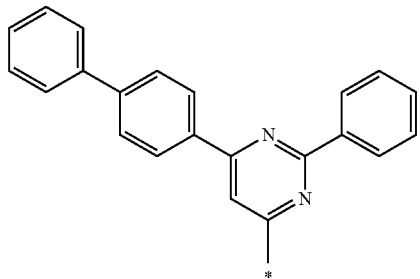
A-28
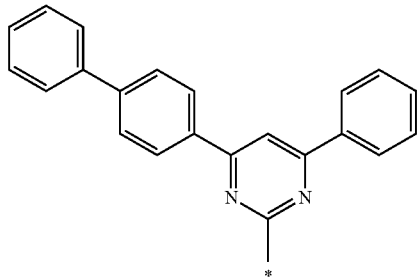
A-29
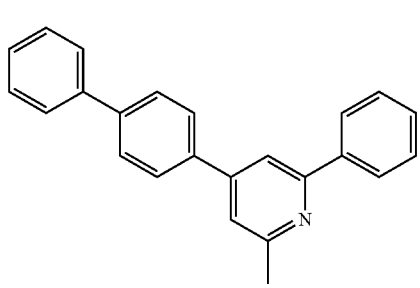
A-30
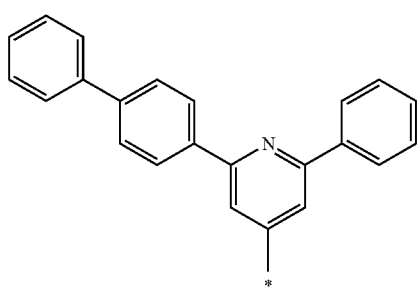
A-31
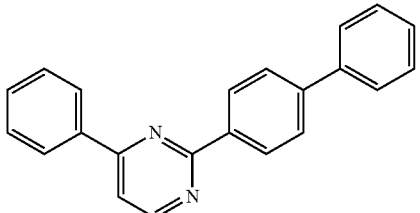
A-32
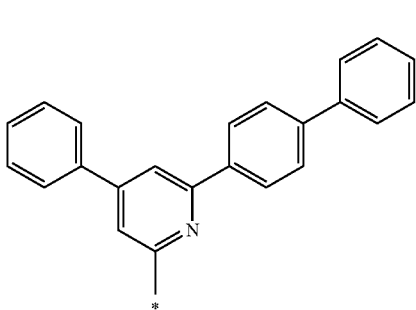
A-33
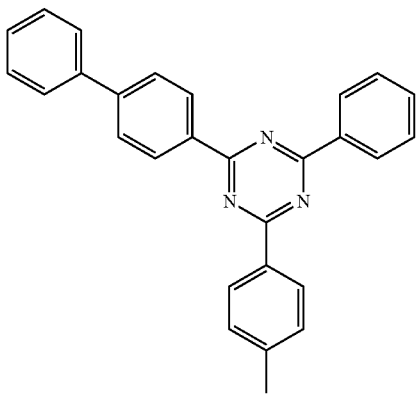
A-34
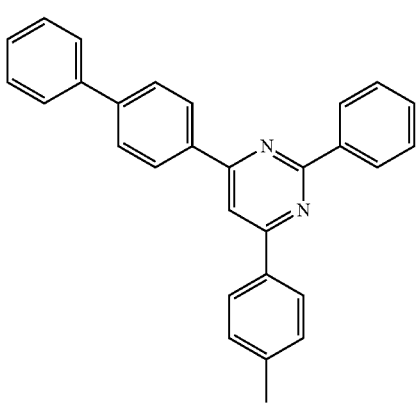

A-35
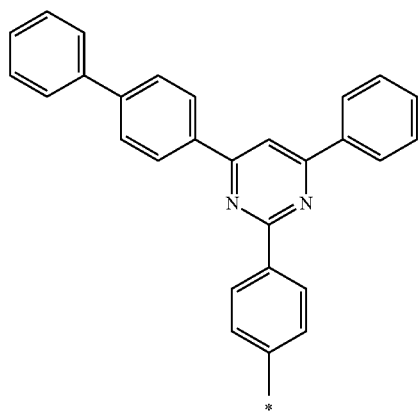
A-36
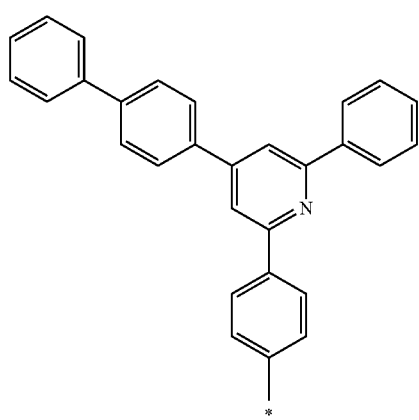
A-37
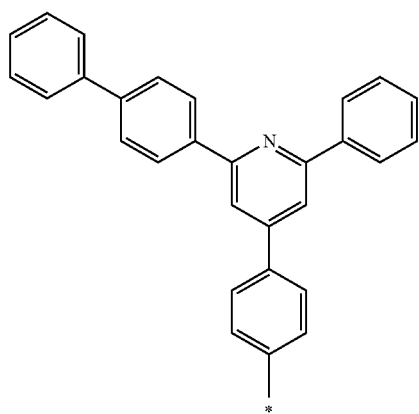
A-38
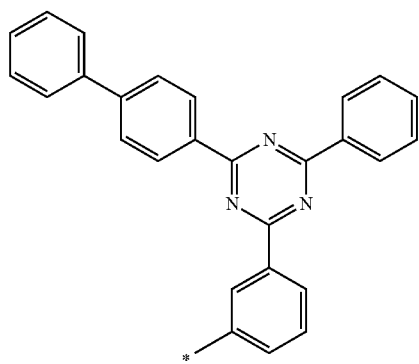
A-39
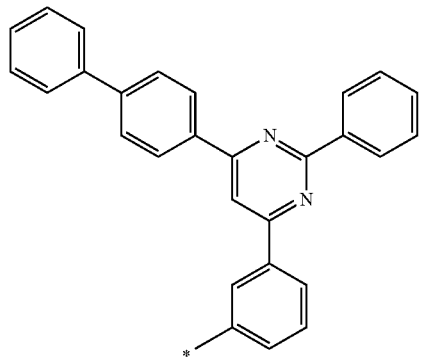
A-40
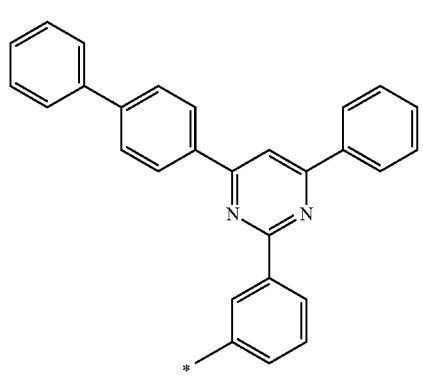
A-41
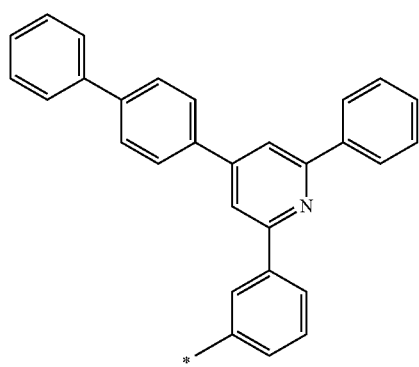
A-42
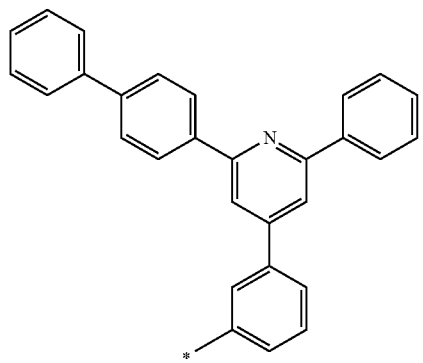

A-43

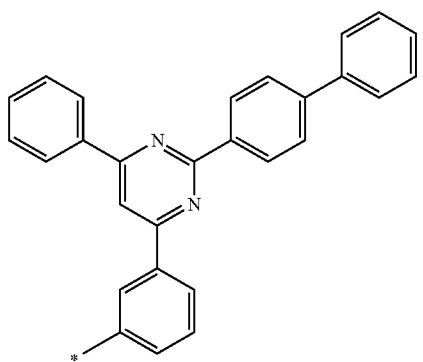

A-44

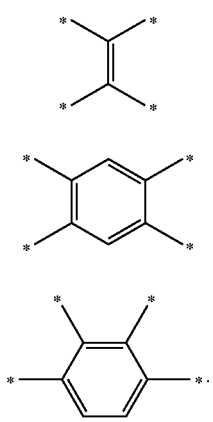

5. The composition as claimed in claim 1, wherein the moiety represented by the Chemical Formula 2 is represented by one of the following Chemical Formulae 2-1 to 2-3:

[Chemical Formula 2-1]

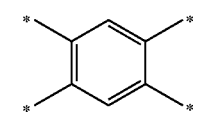

[Chemical Formula 2-2]

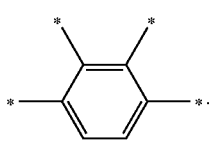

[Chemical Formula 2-3]

6. The composition as claimed in claim 1, wherein the $Ar^1$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, or a combination thereof.

7. The composition as claimed in claim 1, wherein the $X^2$ is one of the substituents listed in the following Group 3:

[Group 3]

B-1

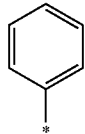

B-2

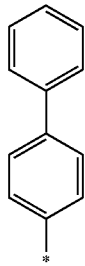

B-3

B-4

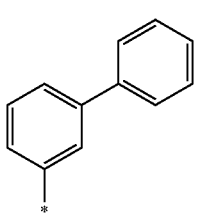

B-5

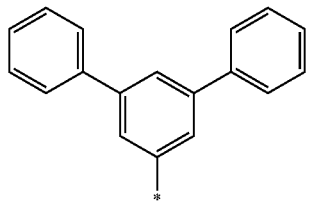

B-6

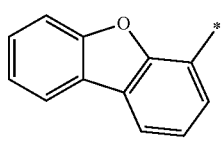

B-7

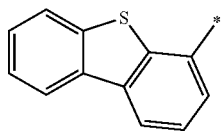

B-8

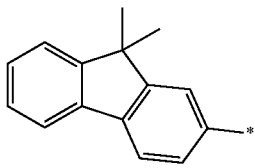

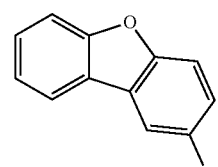

-continued

B-9
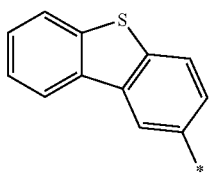

B-10
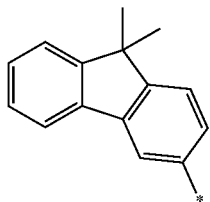

B-11
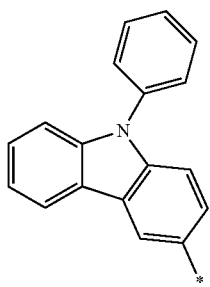

B-12
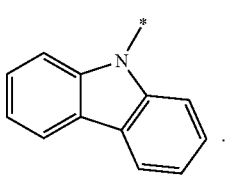

8. The composition as claimed in claim 1, wherein the first host compound is one of compounds listed in the following Group 4:

[Group 4]

[5a-1]
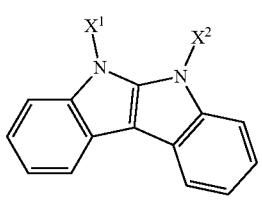

[5a-2]
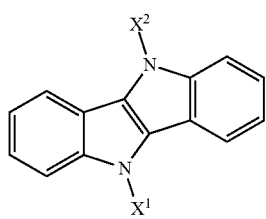

-continued

[5b-1]
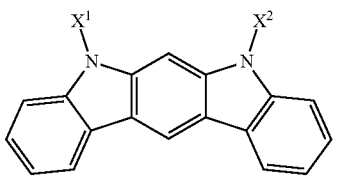

[5b-2]
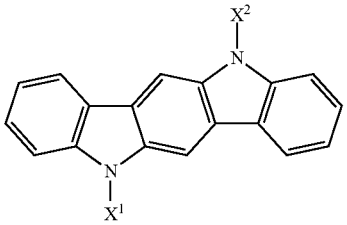

[5c-1]
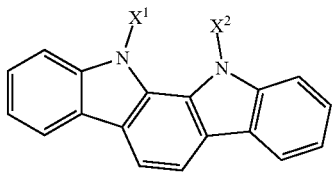

[5c-2]
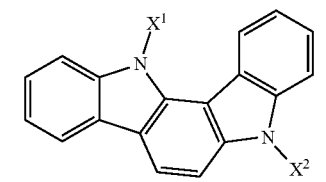

[5c-3]
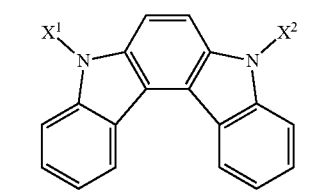

[5c-4]
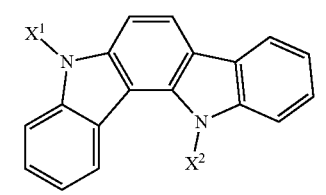

wherein, in the Group 4,
$X^1$ is *—$Y^1$-ET,
$X^2$ is *—$Y^2$—Ar,
ET is a substituent for accepting an electron when an electric field is applied,
$Ar^1$ is a substituted or unsubstituted C6 to C30 aryl group, a substituted or unsubstituted C2 to C30 heteroaryl group, or a combination thereof, and
$Y^1$ and $Y^2$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof.

9. The composition as claimed in claim 1, wherein $Ar^2$ and $Ar^3$ are each independently an unsubstituted phenyl group, an unsubstituted biphenyl group, an unsubstituted terphenyl group, an unsubstituted naphthyl group, an unsubstituted anthracenyl A group, a substituted or unsubstituted carbazolyl group, a substituted or unsubstituted fluorenyl group, or a combination thereof.

10. The composition as claimed in claim 1, wherein:
Chemical Formula 4 is one of structures listed in the following Group 5, and
the *—Y³—Ar² and *—Y⁴—Ar³ in Chemical Formula 4 are each independently one of substituents listed in the following Group 3,

[Group 5]

C-1
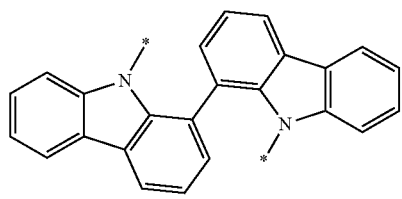

C-2
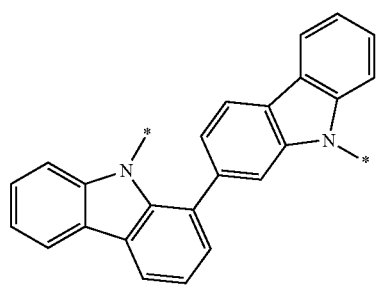

C-3
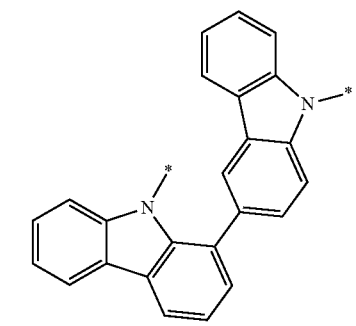

C-4
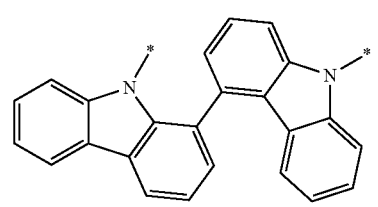

C-5
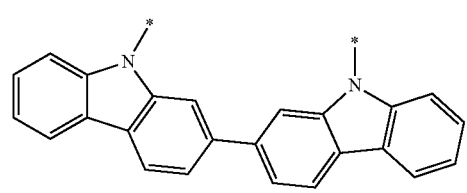

C-6
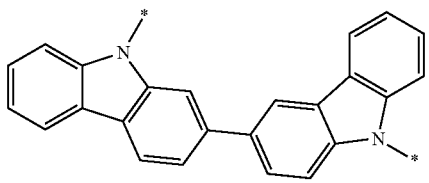

C-7
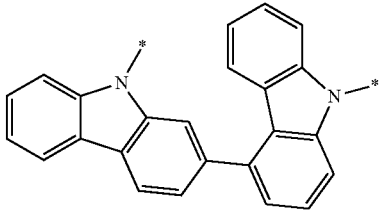

C-8
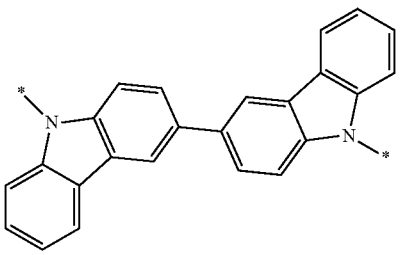

C-9
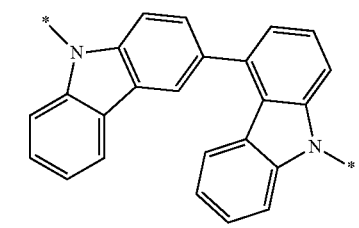

C-10
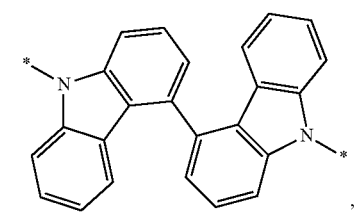

,

[Group 3]

B-1
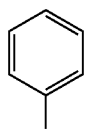

B-2
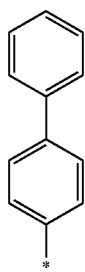

-continued

B-3
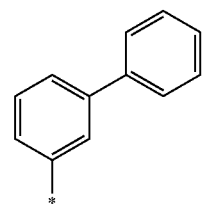

B-4
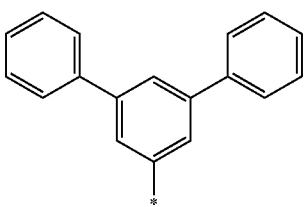

B-7
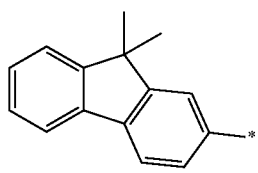

B-10
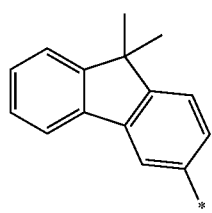

B-11
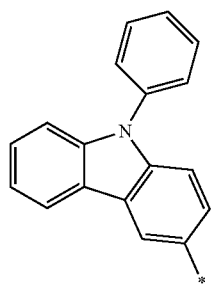

B-12
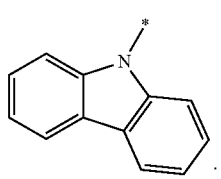

[Group 5]

C-1
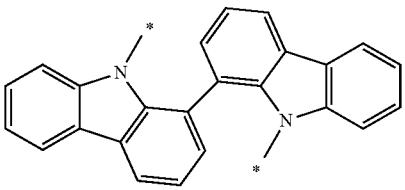

C-2
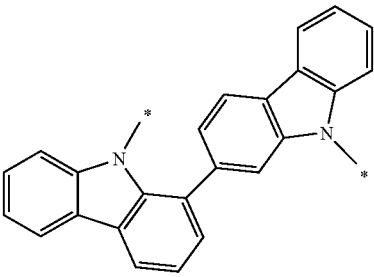

C-3
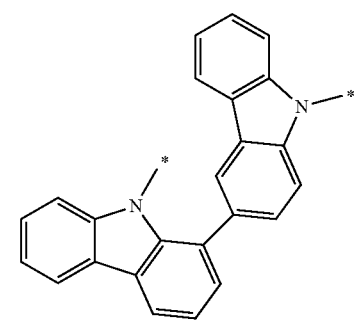

C-4
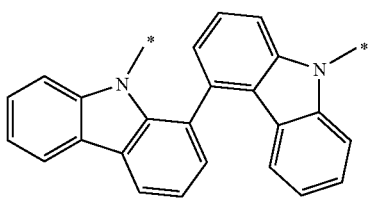

C-5
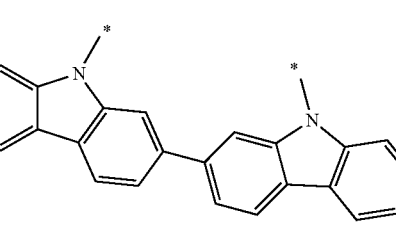

C-6
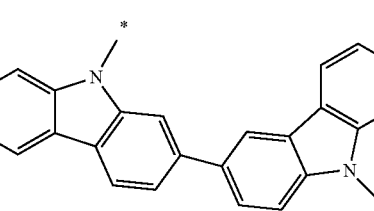

11. The composition as claimed in claim 1, wherein the second host compound represented by Chemical Formula 4 is one of the compounds listed in the following Tables 12 to 21, wherein, in the Tables, "Grp 5" is one of structures listed in the following Group 5, and the "*—$Y^3$—$Ar^2$" and "*—$Y^4$—$Ar^3$" are each independently one of substituents listed in the following Group 3, C-7
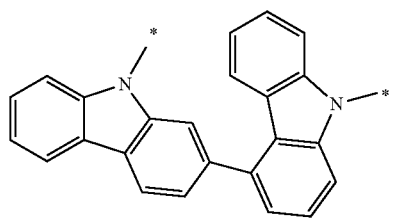
C-8
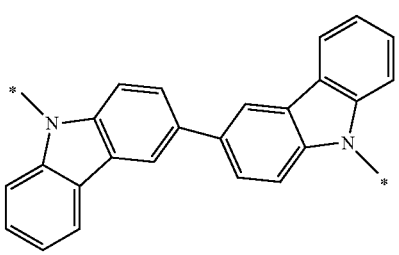
C-9
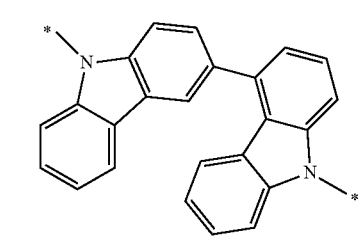
C-10
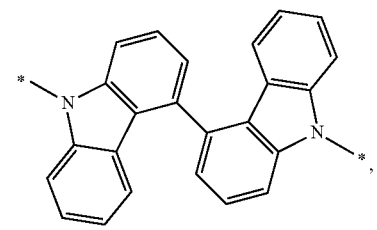
[Group 3]
B-1
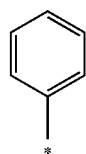
B-2
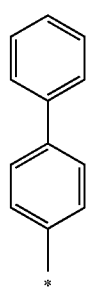
B-3
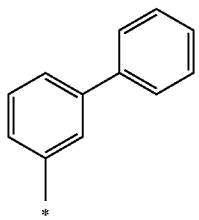
B-4
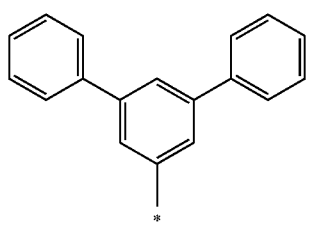
B-5
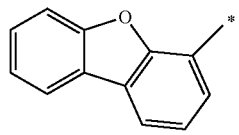
B-6
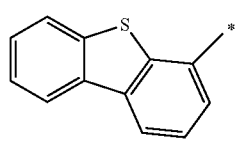
B-7
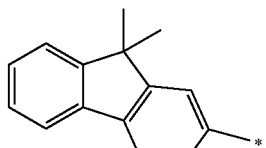
B-8
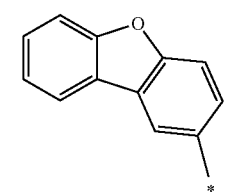
B-9
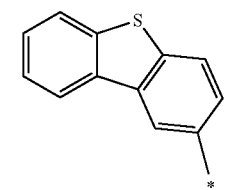
B-10
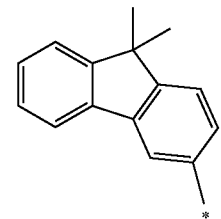

-continued

B-11

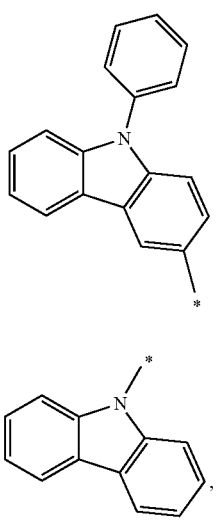

B-12

TABLE 12-continued

| Cmpd No. | Grp 5 | *—Y³—Ar² | *—Y⁴—Ar³ |
|---|---|---|---|
| 2-97 | C-2 | B-2 | B-7 |
| 2-100 | C-2 | B-2 | B-10 |
| 2-101 | C-2 | B-2 | B-11 |
| 2-102 | C-2 | B-2 | B-12 |
| 2-103 | C-2 | B-3 | B-1 |
| 2-104 | C-2 | B-3 | B-2 |
| 2-105 | C-2 | B-3 | B-3 |
| 2-106 | C-2 | B-3 | B-4 |
| 2-109 | C-2 | B-3 | B-7 |
| 2-112 | C-2 | B-3 | B-10 |
| 2-113 | C-2 | B-3 | B-11 |
| 2-114 | C-2 | B-3 | B-12 |
| 2-115 | C-2 | B-4 | B-1 |
| 2-116 | C-2 | B-4 | B-2 |
| 2-117 | C-2 | B-4 | B-3 |
| 2-118 | C-2 | B-4 | B-4 |
| 2-121 | C-2 | B-4 | B-7 |
| 2-124 | C-2 | B-4 | B-10 |
| 2-125 | C-2 | B-4 | B-11 |
| 2-126 | C-2 | B-4 | B-12 |

TABLE 12

| Cmpd No. | Grp 5 | *—Y³—Ar² | *—Y⁴—Ar³ |
|---|---|---|---|
| 2-1 | C-1 | B-1 | B-1 |
| 2-2 | C-1 | B-1 | B-2 |
| 2-3 | C-1 | B-1 | B-3 |
| 2-4 | C-1 | B-1 | B-4 |
| 2-7 | C-1 | B-1 | B-7 |
| 2-10 | C-1 | B-1 | B-10 |
| 2-11 | C-1 | B-1 | B-11 |
| 2-12 | C-1 | B-1 | B-12 |
| 2-13 | C-1 | B-2 | B-2 |
| 2-14 | C-1 | B-2 | B-3 |
| 2-15 | C-1 | B-2 | B-4 |
| 2-18 | C-1 | B-2 | B-7 |
| 2-21 | C-1 | B-2 | B-10 |
| 2-22 | C-1 | B-2 | B-11 |
| 2-23 | C-1 | B-2 | B-12 |
| 2-24 | C-1 | B-3 | B-3 |
| 2-25 | C-1 | B-3 | B-4 |
| 2-28 | C-1 | B-3 | B-7 |
| 2-31 | C-1 | B-3 | B-10 |
| 2-32 | C-1 | B-3 | B-11 |
| 2-33 | C-1 | B-3 | B-12 |
| 2-34 | C-1 | B-4 | B-4 |
| 2-37 | C-1 | B-4 | B-7 |
| 2-40 | C-1 | B-4 | B-10 |
| 2-41 | C-1 | B-4 | B-11 |
| 2-42 | C-1 | B-4 | B-12 |
| 2-58 | C-1 | B-7 | B-7 |
| 2-61 | C-1 | B-7 | B-10 |
| 2-62 | C-1 | B-7 | B-11 |
| 2-63 | C-1 | B-7 | B-12 |
| 2-73 | C-1 | B-10 | B-10 |
| 2-74 | C-1 | B-10 | B-11 |
| 2-75 | C-1 | B-10 | B-12 |
| 2-76 | C-1 | B-11 | B-11 |
| 2-77 | C-1 | B-11 | B-12 |
| 2-78 | C-1 | B-12 | B-12 |
| 2-79 | C-2 | B-1 | B-1 |
| 2-80 | C-2 | B-1 | B-2 |
| 2-81 | C-2 | B-1 | B-3 |
| 2-82 | C-2 | B-1 | B-4 |
| 2-85 | C-2 | B-1 | B-7 |
| 2-88 | C-2 | B-1 | B-10 |
| 2-89 | C-2 | B-1 | B-11 |
| 2-90 | C-2 | B-1 | B-12 |
| 2-91 | C-2 | B-2 | B-1 |
| 2-92 | C-2 | B-2 | B-2 |
| 2-93 | C-2 | B-2 | B-3 |
| 2-94 | C-2 | B-2 | B-4 |

TABLE 13

| Cmpd No. | Grp 5 | *—Y³—Ar² | *—Y⁴—Ar³ |
|---|---|---|---|
| 2-151 | C-2 | B-7 | B-1 |
| 2-152 | C-2 | B-7 | B-2 |
| 2-153 | C-2 | B-7 | B-3 |
| 2-154 | C-2 | B-7 | B-4 |
| 2-157 | C-2 | B-7 | B-7 |
| 2-160 | C-2 | B-7 | B-10 |
| 2-161 | C-2 | B-7 | B-11 |
| 2-162 | C-2 | B-7 | B-12 |
| 2-187 | C-2 | B-10 | B-1 |
| 2-188 | C-2 | B-10 | B-2 |
| 2-189 | C-2 | B-10 | B-3 |
| 2-190 | C-2 | B-10 | B-4 |
| 2-193 | C-2 | B-10 | B-7 |
| 2-196 | C-2 | B-10 | B-10 |
| 2-197 | C-2 | B-10 | B-11 |
| 2-198 | C-2 | B-10 | B-12 |
| 2-199 | C-2 | B-11 | B-1 |
| 2-200 | C-2 | B-11 | B-2 |
| 2-201 | C-2 | B-11 | B-3 |
| 2-202 | C-2 | B-11 | B-4 |
| 2-205 | C-2 | B-11 | B-7 |
| 2-208 | C-2 | B-11 | B-10 |
| 2-209 | C-2 | B-11 | B-11 |
| 2-210 | C-2 | B-11 | B-12 |
| 2-211 | C-2 | B-12 | B-1 |
| 2-212 | C-2 | B-12 | B-2 |
| 2-213 | C-2 | B-12 | B-3 |
| 2-214 | C-2 | B-12 | B-4 |
| 2-217 | C-2 | B-12 | B-7 |
| 2-220 | C-2 | B-12 | B-10 |
| 2-221 | C-2 | B-12 | B-11 |
| 2-222 | C-2 | B-12 | B-12 |
| 2-223 | C-3 | B-1 | B-1 |
| 2-224 | C-3 | B-1 | B-2 |
| 2-225 | C-3 | B-1 | B-3 |
| 2-226 | C-3 | B-1 | B-4 |
| 2-229 | C-3 | B-1 | B-7 |
| 2-232 | C-3 | B-1 | B-10 |
| 2-233 | C-3 | B-1 | B-11 |
| 2-234 | C-3 | B-1 | B-12 |
| 2-235 | C-3 | B-2 | B-1 |
| 2-236 | C-3 | B-2 | B-2 |
| 2-237 | C-3 | B-2 | B-3 |
| 2-238 | C-3 | B-2 | B-4 |
| 2-241 | C-3 | B-2 | B-7 |
| 2-244 | C-3 | B-2 | B-10 |
| 2-245 | C-3 | B-2 | B-11 |
| 2-246 | C-3 | B-2 | B-12 |

TABLE 13-continued

| Cmpd No. | Grp 5 | *—Y³—Ar² | *—Y⁴—Ar³ |
| --- | --- | --- | --- |
| 2-247 | C-3 | B-3 | B-1 |
| 2-248 | C-3 | B-3 | B-2 |
| 2-249 | C-3 | B-3 | B-3 |
| 2-250 | C-3 | B-3 | B-4 |
| 2-253 | C-3 | B-3 | B-7 |
| 2-256 | C-3 | B-3 | B-10 |
| 2-257 | C-3 | B-3 | B-11 |
| 2-258 | C-3 | B-3 | B-12 |
| 2-259 | C-3 | B-4 | B-1 |
| 2-260 | C-3 | B-4 | B-2 |
| 2-261 | C-3 | B-4 | B-3 |
| 2-262 | C-3 | B-4 | B-4 |

TABLE 14

| Cmpd No. | Grp 5 | *—Y³—Ar² | *—Y⁴—Ar³ |
| --- | --- | --- | --- |
| 2-265 | C-3 | B-4 | B-7 |
| 2-268 | C-3 | B-4 | B-10 |
| 2-269 | C-3 | B-4 | B-11 |
| 2-270 | C-3 | B-4 | B-12 |
| 2-295 | C-3 | B-7 | B-1 |
| 2-296 | C-3 | B-7 | B-2 |
| 2-297 | C-3 | B-7 | B-3 |
| 2-298 | C-3 | B-7 | B-4 |
| 2-301 | C-3 | B-7 | B-7 |
| 2-304 | C-3 | B-7 | B-10 |
| 2-305 | C-3 | B-7 | B-11 |
| 2-306 | C-3 | B-7 | B-12 |
| 2-331 | C-3 | B-10 | B-1 |
| 2-332 | C-3 | B-10 | B-2 |
| 2-333 | C-3 | B-10 | B-3 |
| 2-334 | C-3 | B-10 | B-4 |
| 2-337 | C-3 | B-10 | B-7 |
| 2-340 | C-3 | B-10 | B-10 |
| 2-341 | C-3 | B-10 | B-11 |
| 2-342 | C-3 | B-10 | B-12 |
| 2-343 | C-3 | B-11 | B-1 |
| 2-344 | C-3 | B-11 | B-2 |
| 2-345 | C-3 | B-11 | B-3 |
| 2-346 | C-3 | B-11 | B-4 |
| 2-349 | C-3 | B-11 | B-7 |
| 2-352 | C-3 | B-11 | B-10 |
| 2-353 | C-3 | B-11 | B-11 |
| 2-354 | C-3 | B-11 | B-12 |
| 2-355 | C-3 | B-12 | B-1 |
| 2-356 | C-3 | B-12 | B-2 |
| 2-357 | C-3 | B-12 | B-3 |
| 2-358 | C-3 | B-12 | B-4 |
| 2-361 | C-3 | B-12 | B-7 |
| 2-364 | C-3 | B-12 | B-10 |
| 2-365 | C-3 | B-12 | B-11 |
| 2-366 | C-3 | B-12 | B-12 |
| 2-367 | C-4 | B-1 | B-1 |
| 2-368 | C-4 | B-1 | B-2 |
| 2-369 | C-4 | B-1 | B-3 |
| 2-370 | C-4 | B-1 | B-4 |
| 2-373 | C-4 | B-1 | B-7 |
| 2-376 | C-4 | B-1 | B-10 |
| 2-377 | C-4 | B-1 | B-11 |
| 2-378 | C-4 | B-1 | B-12 |
| 2-379 | C-4 | B-2 | B-1 |
| 2-380 | C-4 | B-2 | B-2 |
| 2-381 | C-4 | B-2 | B-3 |
| 2-382 | C-4 | B-2 | B-4 |
| 2-385 | C-4 | B-2 | B-7 |
| 2-388 | C-4 | B-2 | B-10 |
| 2-389 | C-4 | B-2 | B-11 |
| 2-390 | C-4 | B-2 | B-12 |
| 2-391 | C-4 | B-3 | B-1 |
| 2-392 | C-4 | B-3 | B-2 |
| 2-393 | C-4 | B-3 | B-3 |
| 2-394 | C-4 | B-3 | B-4 |

TABLE 15

| Cmpd No. | Grp 5 | *—Y³—Ar² | *—Y⁴—Ar³ |
| --- | --- | --- | --- |
| 2-397 | C-4 | B-3 | B-7 |
| 2-400 | C-4 | B-3 | B-10 |
| 2-401 | C-4 | B-3 | B-11 |
| 2-402 | C-4 | B-3 | B-12 |
| 2-403 | C-4 | B-4 | B-1 |
| 2-404 | C-4 | B-4 | B-2 |
| 2-405 | C-4 | B-4 | B-3 |
| 2-406 | C-4 | B-4 | B-4 |
| 2-409 | C-4 | B-4 | B-7 |
| 2-412 | C-4 | B-4 | B-10 |
| 2-413 | C-4 | B-4 | B-11 |
| 2-414 | C-4 | B-4 | B-12 |
| 2-439 | C-4 | B-7 | B-1 |
| 2-440 | C-4 | B-7 | B-2 |
| 2-441 | C-4 | B-7 | B-3 |
| 2-442 | C-4 | B-7 | B-4 |
| 2-445 | C-4 | B-7 | B-7 |
| 2-448 | C-4 | B-7 | B-10 |
| 2-449 | C-4 | B-7 | B-11 |
| 2-450 | C-4 | B-7 | B-12 |
| 2-475 | C-4 | B-10 | B-1 |
| 2-476 | C-4 | B-10 | B-2 |
| 2-477 | C-4 | B-10 | B-3 |
| 2-478 | C-4 | B-10 | B-4 |
| 2-481 | C-4 | B-10 | B-7 |
| 2-484 | C-4 | B-10 | B-10 |
| 2-485 | C-4 | B-10 | B-11 |
| 2-486 | C-4 | B-10 | B-12 |
| 2-487 | C-4 | B-11 | B-1 |
| 2-488 | C-4 | B-11 | B-2 |
| 2-489 | C-4 | B-11 | B-3 |
| 2-490 | C-4 | B-11 | B-4 |
| 2-493 | C-4 | B-11 | B-7 |
| 2-496 | C-4 | B-11 | B-10 |
| 2-497 | C-4 | B-11 | B-11 |
| 2-498 | C-4 | B-11 | B-12 |
| 2-499 | C-4 | B-12 | B-1 |
| 2-500 | C-4 | B-12 | B-2 |
| 2-501 | C-4 | B-12 | B-3 |
| 2-502 | C-4 | B-12 | B-4 |
| 2-505 | C-4 | B-12 | B-7 |
| 2-508 | C-4 | B-12 | B-10 |
| 2-509 | C-4 | B-12 | B-11 |
| 2-510 | C-4 | B-12 | B-12 |
| 2-511 | C-5 | B-1 | B-1 |
| 2-512 | C-5 | B-1 | B-2 |
| 2-513 | C-5 | B-1 | B-3 |
| 2-514 | C-5 | B-1 | B-4 |
| 2-517 | C-5 | B-1 | B-7 |
| 2-520 | C-5 | B-1 | B-10 |
| 2-521 | C-5 | B-1 | B-11 |
| 2-522 | C-5 | B-1 | B-12 |
| 2-523 | C-5 | B-2 | B-1 |
| 2-524 | C-5 | B-2 | B-2 |
| 2-525 | C-5 | B-2 | B-3 |
| 2-526 | C-5 | B-2 | B-4 |

TABLE 16

| Cmpd No. | Grp 5 | *—Y³—Ar² | *—Y⁴—Ar³ |
| --- | --- | --- | --- |
| 2-529 | C-5 | B-2 | B-7 |
| 2-532 | C-5 | B-2 | B-10 |
| 2-533 | C-5 | B-2 | B-11 |
| 2-534 | C-5 | B-2 | B-12 |

TABLE 16-continued

| Cmpd No. | Grp 5 | *—Y³—Ar² | *—Y⁴—Ar³ |
|---|---|---|---|
| 2-535 | C-5 | B-3 | B-1 |
| 2-536 | C-5 | B-3 | B-2 |
| 2-537 | C-5 | B-3 | B-3 |
| 2-538 | C-5 | B-3 | B-4 |
| 2-541 | C-5 | B-3 | B-7 |
| 2-544 | C-5 | B-3 | B-10 |
| 2-545 | C-5 | B-3 | B-11 |
| 2-546 | C-5 | B-3 | B-12 |
| 2-547 | C-5 | B-4 | B-1 |
| 2-548 | C-5 | B-4 | B-2 |
| 2-549 | C-5 | B-4 | B-3 |
| 2-550 | C-5 | B-4 | B-4 |
| 2-553 | C-5 | B-4 | B-7 |
| 2-556 | C-5 | B-4 | B-10 |
| 2-557 | C-5 | B-4 | B-11 |
| 2-558 | C-5 | B-4 | B-12 |
| 2-583 | C-5 | B-7 | B-1 |
| 2-584 | C-5 | B-7 | B-2 |
| 2-585 | C-5 | B-7 | B-3 |
| 2-586 | C-5 | B-7 | B-4 |
| 2-589 | C-5 | B-7 | B-7 |
| 2-592 | C-5 | B-7 | B-10 |
| 2-593 | C-5 | B-7 | B-11 |
| 2-594 | C-5 | B-7 | B-12 |
| 2-619 | C-5 | B-10 | B-1 |
| 2-620 | C-5 | B-10 | B-2 |
| 2-621 | C-5 | B-10 | B-3 |
| 2-622 | C-5 | B-10 | B-4 |
| 2-625 | C-5 | B-10 | B-7 |
| 2-628 | C-5 | B-10 | B-10 |
| 2-629 | C-5 | B-10 | B-11 |
| 2-630 | C-5 | B-10 | B-12 |
| 2-631 | C-5 | B-11 | B-1 |
| 2-632 | C-5 | B-11 | B-2 |
| 2-633 | C-5 | B-11 | B-3 |
| 2-634 | C-5 | B-11 | B-4 |
| 2-637 | C-5 | B-11 | B-7 |
| 2-640 | C-5 | B-11 | B-10 |
| 2-641 | C-5 | B-11 | B-11 |
| 2-642 | C-5 | B-11 | B-12 |
| 2-643 | C-5 | B-12 | B-1 |
| 2-644 | C-5 | B-12 | B-2 |
| 2-645 | C-5 | B-12 | B-3 |
| 2-646 | C-5 | B-12 | B-4 |
| 2-649 | C-5 | B-12 | B-7 |
| 2-652 | C-5 | B-12 | B-10 |
| 2-653 | C-5 | B-12 | B-11 |
| 2-654 | C-5 | B-12 | B-12 |
| 2-655 | C-6 | B-1 | B-1 |
| 2-656 | C-6 | B-1 | B-2 |
| 2-657 | C-6 | B-1 | B-3 |
| 2-658 | C-6 | B-1 | B-4 |

TABLE 17

| Cmpd No. | Grp 5 | *—Y³—Ar² | *—Y⁴—Ar³ |
|---|---|---|---|
| 2-661 | C-6 | B-1 | B-7 |
| 2-664 | C-6 | B-1 | B-10 |
| 2-665 | C-6 | B-1 | B-11 |
| 2-666 | C-6 | B-1 | B-12 |
| 2-667 | C-6 | B-2 | B-1 |
| 2-668 | C-6 | B-2 | B-2 |
| 2-669 | C-6 | B-2 | B-3 |
| 2-670 | C-6 | B-2 | B-4 |
| 2-673 | C-6 | B-2 | B-7 |
| 2-676 | C-6 | B-2 | B-10 |
| 2-677 | C-6 | B-2 | B-11 |
| 2-678 | C-6 | B-2 | B-12 |
| 2-679 | C-6 | B-3 | B-1 |
| 2-680 | C-6 | B-3 | B-2 |
| 2-681 | C-6 | B-3 | B-3 |
| 2-682 | C-6 | B-3 | B-4 |

TABLE 17-continued

| Cmpd No. | Grp 5 | *—Y³—Ar² | *—Y⁴—Ar³ |
|---|---|---|---|
| 2-685 | C-6 | B-3 | B-7 |
| 2-688 | C-6 | B-3 | B-10 |
| 2-689 | C-6 | B-3 | B-11 |
| 2-690 | C-6 | B-3 | B-12 |
| 2-691 | C-6 | B-4 | B-1 |
| 2-692 | C-6 | B-4 | B-2 |
| 2-693 | C-6 | B-4 | B-3 |
| 2-694 | C-6 | B-4 | B-4 |
| 2-697 | C-6 | B-4 | B-7 |
| 2-700 | C-6 | B-4 | B-10 |
| 2-701 | C-6 | B-4 | B-11 |
| 2-702 | C-6 | B-4 | B-12 |
| 2-727 | C-6 | B-7 | B-1 |
| 2-728 | C-6 | B-7 | B-2 |
| 2-729 | C-6 | B-7 | B-3 |
| 2-730 | C-6 | B-7 | B-4 |
| 2-733 | C-6 | B-7 | B-7 |
| 2-736 | C-6 | B-7 | B-10 |
| 2-737 | C-6 | B-7 | B-11 |
| 2-738 | C-6 | B-7 | B-12 |
| 2-763 | C-6 | B-10 | B-1 |
| 2-764 | C-6 | B-10 | B-2 |
| 2-765 | C-6 | B-10 | B-3 |
| 2-766 | C-6 | B-10 | B-4 |
| 2-769 | C-6 | B-10 | B-7 |
| 2-772 | C-6 | B-10 | B-10 |
| 2-773 | C-6 | B-10 | B-11 |
| 2-774 | C-6 | B-10 | B-12 |
| 2-775 | C-6 | B-11 | B-1 |
| 2-776 | C-6 | B-11 | B-2 |
| 2-777 | C-6 | B-11 | B-3 |
| 2-778 | C-6 | B-11 | B-4 |
| 2-781 | C-6 | B-11 | B-7 |
| 2-784 | C-6 | B-11 | B-10 |
| 2-785 | C-6 | B-11 | B-11 |
| 2-786 | C-6 | B-11 | B-12 |
| 2-787 | C-6 | B-12 | B-1 |
| 2-788 | C-6 | B-12 | B-2 |
| 2-789 | C-6 | B-12 | B-3 |
| 2-790 | C-6 | B-12 | B-4 |

TABLE 18

| Cmpd No. | Grp 5 | *—Y³—Ar² | *—Y⁴—Ar³ |
|---|---|---|---|
| 2-793 | C-6 | B-12 | B-7 |
| 2-796 | C-6 | B-12 | B-10 |
| 2-797 | C-6 | B-12 | B-11 |
| 2-798 | C-6 | B-12 | B-12 |
| 2-799 | C-7 | B-1 | B-1 |
| 2-800 | C-7 | B-1 | B-2 |
| 2-801 | C-7 | B-1 | B-3 |
| 2-802 | C-7 | B-1 | B-4 |
| 2-805 | C-7 | B-1 | B-7 |
| 2-808 | C-7 | B-1 | B-10 |
| 2-809 | C-7 | B-1 | B-11 |
| 2-810 | C-7 | B-1 | B-12 |
| 2-811 | C-7 | B-2 | B-1 |
| 2-812 | C-7 | B-2 | B-2 |
| 2-813 | C-7 | B-2 | B-3 |
| 2-814 | C-7 | B-2 | B-4 |
| 2-817 | C-7 | B-2 | B-7 |
| 2-820 | C-7 | B-2 | B-10 |
| 2-821 | C-7 | B-2 | B-11 |
| 2-822 | C-7 | B-2 | B-12 |
| 2-823 | C-7 | B-3 | B-1 |
| 2-824 | C-7 | B-3 | B-2 |
| 2-825 | C-7 | B-3 | B-3 |
| 2-826 | C-7 | B-3 | B-4 |
| 2-829 | C-7 | B-3 | B-7 |
| 2-832 | C-7 | B-3 | B-10 |
| 2-833 | C-7 | B-3 | B-11 |
| 2-834 | C-7 | B-3 | B-12 |

TABLE 18-continued

| Cmpd No. | Grp 5 | *—Y³—Ar² | *—Y⁴—Ar³ |
|---|---|---|---|
| 2-835 | C-7 | B-4 | B-1 |
| 2-836 | C-7 | B-4 | B-2 |
| 2-837 | C-7 | B-4 | B-3 |
| 2-838 | C-7 | B-4 | B-4 |
| 2-841 | C-7 | B-4 | B-7 |
| 2-844 | C-7 | B-4 | B-10 |
| 2-845 | C-7 | B-4 | B-11 |
| 2-846 | C-7 | B-4 | B-12 |
| 2-871 | C-7 | B-7 | B-1 |
| 2-872 | C-7 | B-7 | B-2 |
| 2-873 | C-7 | B-7 | B-3 |
| 2-874 | C-7 | B-7 | B-4 |
| 2-877 | C-7 | B-7 | B-7 |
| 2-880 | C-7 | B-7 | B-10 |
| 2-881 | C-7 | B-7 | B-11 |
| 2-882 | C-7 | B-7 | B-12 |
| 2-907 | C-7 | B-10 | B-1 |
| 2-908 | C-7 | B-10 | B-2 |
| 2-909 | C-7 | B-10 | B-3 |
| 2-910 | C-7 | B-10 | B-4 |
| 2-913 | C-7 | B-10 | B-7 |
| 2-916 | C-7 | B-10 | B-10 |
| 2-917 | C-7 | B-10 | B-11 |
| 2-918 | C-7 | B-10 | B-12 |
| 2-919 | C-7 | B-11 | B-1 |
| 2-920 | C-7 | B-11 | B-2 |
| 2-921 | C-7 | B-11 | B-3 |
| 2-922 | C-7 | B-11 | B-4 |

TABLE 19

| Cmpd No. | Grp 5 | *—Y³—Ar² | *—Y⁴—Ar³ |
|---|---|---|---|
| 2-925 | C-7 | B-11 | B-7 |
| 2-928 | C-7 | B-11 | B-10 |
| 2-929 | C-7 | B-11 | B-11 |
| 2-930 | C-7 | B-11 | B-12 |
| 2-931 | C-7 | B-12 | B-1 |
| 2-932 | C-7 | B-12 | B-2 |
| 2-933 | C-7 | B-12 | B-3 |
| 2-934 | C-7 | B-12 | B-4 |
| 2-937 | C-7 | B-12 | B-7 |
| 2-940 | C-7 | B-12 | B-10 |
| 2-941 | C-7 | B-12 | B-11 |
| 2-942 | C-7 | B-12 | B-12 |
| 2-943 | C-8 | B-1 | B-1 |
| 2-944 | C-8 | B-1 | B-2 |
| 2-945 | C-8 | B-1 | B-3 |
| 2-946 | C-8 | B-1 | B-4 |
| 2-949 | C-8 | B-1 | B-7 |
| 2-952 | C-8 | B-1 | B-10 |
| 2-953 | C-8 | B-1 | B-11 |
| 2-954 | C-8 | B-1 | B-12 |
| 2-955 | C-8 | B-2 | B-2 |
| 2-956 | C-8 | B-2 | B-3 |
| 2-957 | C-8 | B-2 | B-4 |
| 2-960 | C-8 | B-2 | B-7 |
| 2-963 | C-8 | B-2 | B-10 |
| 2-964 | C-8 | B-2 | B-11 |
| 2-965 | C-8 | B-2 | B-12 |
| 2-966 | C-8 | B-3 | B-3 |
| 2-967 | C-8 | B-3 | B-4 |
| 2-970 | C-8 | B-3 | B-7 |
| 2-973 | C-8 | B-3 | B-10 |
| 2-974 | C-8 | B-3 | B-11 |
| 2-975 | C-8 | B-3 | B-12 |
| 2-976 | C-8 | B-4 | B-4 |
| 2-979 | C-8 | B-4 | B-7 |
| 2-982 | C-8 | B-4 | B-10 |
| 2-983 | C-8 | B-4 | B-11 |
| 2-984 | C-8 | B-4 | B-12 |
| 2-1000 | C-8 | B-7 | B-7 |
| 2-1003 | C-8 | B-7 | B-10 |

TABLE 19-continued

| Cmpd No. | Grp 5 | *—Y³—Ar² | *—Y⁴—Ar³ |
|---|---|---|---|
| 2-1004 | C-8 | B-7 | B-11 |
| 2-1005 | C-8 | B-7 | B-12 |
| 2-1015 | C-8 | B-10 | B-10 |
| 2-1016 | C-8 | B-10 | B-11 |
| 2-1017 | C-8 | B-10 | B-12 |
| 2-1018 | C-8 | B-11 | B-11 |
| 2-1019 | C-8 | B-11 | B-12 |
| 2-1020 | C-8 | B-12 | B-12 |
| 2-1021 | C-9 | B-1 | B-1 |
| 2-1022 | C-9 | B-1 | B-2 |
| 2-1023 | C-9 | B-1 | B-3 |
| 2-1024 | C-9 | B-1 | B-4 |
| 2-1027 | C-9 | B-1 | B-7 |
| 2-1030 | C-9 | B-1 | B-10 |
| 2-1031 | C-9 | B-1 | B-11 |
| 2-1032 | C-9 | B-1 | B-12 |
| 2-1033 | C-9 | B-2 | B-1 |
| 2-1034 | C-9 | B-2 | B-2 |
| 2-1035 | C-9 | B-2 | B-3 |
| 2-1036 | C-9 | B-2 | B-4 |
| 2-1039 | C-9 | B-2 | B-7 |
| 2-1042 | C-9 | B-2 | B-10 |
| 2-1043 | C-9 | B-2 | B-11 |
| 2-1044 | C-9 | B-2 | B-12 |
| 2-1045 | C-9 | B-3 | B-1 |
| 2-1046 | C-9 | B-3 | B-2 |
| 2-1047 | C-9 | B-3 | B-3 |
| 2-1048 | C-9 | B-3 | B-4 |
| 2-1051 | C-9 | B-3 | B-7 |
| 2-1054 | C-9 | B-3 | B-10 |
| 2-1055 | C-9 | B-3 | B-11 |
| 2-1056 | C-9 | B-3 | B-12 |

TABLE 20

| Cmpd No. | Grp 5 | *—Y³—Ar² | *—Y⁴—Ar³ |
|---|---|---|---|
| 2-1057 | C-9 | B-4 | B-1 |
| 2-1058 | C-9 | B-4 | B-2 |
| 2-1059 | C-9 | B-4 | B-3 |
| 2-1060 | C-9 | B-4 | B-4 |
| 2-1063 | C-9 | B-4 | B-7 |
| 2-1066 | C-9 | B-4 | B-10 |
| 2-1067 | C-9 | B-4 | B-11 |
| 2-1068 | C-9 | B-4 | B-12 |
| 2-1094 | C-9 | B-7 | B-2 |
| 2-1095 | C-9 | B-7 | B-3 |
| 2-1096 | C-9 | B-7 | B-4 |
| 2-1099 | C-9 | B-7 | B-7 |
| 2-1102 | C-9 | B-7 | B-10 |
| 2-1103 | C-9 | B-7 | B-11 |
| 2-1104 | C-9 | B-7 | B-12 |
| 2-1129 | C-9 | B-10 | B-1 |
| 2-1130 | C-9 | B-10 | B-2 |
| 2-1131 | C-9 | B-10 | B-3 |
| 2-1132 | C-9 | B-10 | B-4 |
| 2-1135 | C-9 | B-10 | B-7 |
| 2-1138 | C-9 | B-10 | B-10 |
| 2-1139 | C-9 | B-10 | B-11 |
| 2-1140 | C-9 | B-10 | B-12 |
| 2-1141 | C-9 | B-11 | B-1 |
| 2-1142 | C-9 | B-11 | B-2 |
| 2-1143 | C-9 | B-11 | B-3 |
| 2-1144 | C-9 | B-11 | B-4 |
| 2-1147 | C-9 | B-11 | B-7 |
| 2-1150 | C-9 | B-11 | B-10 |
| 2-1151 | C-9 | B-11 | B-11 |
| 2-1152 | C-9 | B-11 | B-12 |
| 2-1153 | C-9 | B-12 | B-1 |
| 2-1154 | C-9 | B-12 | B-2 |
| 2-1155 | C-9 | B-12 | B-3 |
| 2-1156 | C-9 | B-12 | B-4 |
| 2-1159 | C-9 | B-12 | B-7 |

TABLE 20-continued

| Cmpd No. | Grp 5 | *—Y³—Ar² | *—Y⁴—Ar³ |
|---|---|---|---|
| 2-1162 | C-9 | B-12 | B-10 |
| 2-1163 | C-9 | B-12 | B-11 |
| 2-1164 | C-9 | B-12 | B-12 |
| 2-1165 | C-10 | B-1 | B-1 |
| 2-1166 | C-10 | B-1 | B-2 |
| 2-1167 | C-10 | B-1 | B-3 |
| 2-1168 | C-10 | B-1 | B-4 |
| 2-1171 | C-10 | B-1 | B-7 |
| 2-1174 | C-10 | B-1 | B-10 |
| 2-1175 | C-10 | B-1 | B-11 |
| 2-1176 | C-10 | B-1 | B-12 |
| 2-1177 | C-10 | B-2 | B-2 |
| 2-1178 | C-10 | B-2 | B-3 |
| 2-1179 | C-10 | B-2 | B-4 |
| 2-1182 | C-10 | B-2 | B-7 |
| 2-1185 | C-10 | B-2 | B-10 |
| 2-1186 | C-10 | B-2 | B-11 |
| 2-1187 | C-10 | B-2 | B-12 |
| 2-1188 | C-10 | B-3 | B-3 |

TABLE 21

| Cmpd No. | Grp 5 | *—Y³—Ar² | *—Y⁴—Ar³ |
|---|---|---|---|
| 2-1189 | C-10 | B-3 | B-4 |
| 2-1192 | C-10 | B-3 | B-7 |
| 2-1195 | C-10 | B-3 | B-10 |
| 2-1196 | C-10 | B-3 | B-11 |
| 2-1197 | C-10 | B-3 | B-12 |
| 2-1198 | C-10 | B-4 | B-4 |
| 2-1201 | C-10 | B-4 | B-7 |
| 2-1204 | C-10 | B-4 | B-10 |
| 2-1205 | C-10 | B-4 | B-11 |
| 2-1206 | C-10 | B-4 | B-12 |

TABLE 21-continued

| Cmpd No. | Grp 5 | *—Y³—Ar² | *—Y⁴—Ar³ |
|---|---|---|---|
| 2-1225 | C-10 | B-7 | B-10 |
| 2-1226 | C-10 | B-7 | B-11 |
| 2-1227 | C-10 | B-7 | B-12 |
| 2-1237 | C-10 | B-10 | B-10 |
| 2-1238 | C-10 | B-10 | B-11 |
| 2-1239 | C-10 | B-10 | B-12 |
| 2-1240 | C-10 | B-11 | B-11 |
| 2-1241 | C-10 | B-11 | B-12 |
| 2-1242 | C-10 | B-12 | B-12. |

12. The composition as claimed in claim 1, wherein the first host compound and the second host compound are included in a weight ratio of about 1:10 to about 10:1.

13. The composition as claimed in claim 1, further comprising a dopant.

14. The composition as claimed in claim 1, wherein the composition is capable of forming a film using a dry film-forming method.

15. An organic optoelectric device, comprising:
an anode and a cathode facing each other, and
at least one organic layer interposed between the anode and the cathode, the organic layer including the composition as claimed in claim 1.

16. The organic optoelectric device as claimed in claim 15, wherein
the organic layer includes an emission layer, and
the emission layer includes the composition.

17. The organic optoelectric device as claimed in claim 16, wherein the composition is included in the emission layer as a host, the emission layer further including a dopant.

18. A display device comprising the organic optoelectric device as claimed in claim 15.

* * * * *